(12) United States Patent
Shimizu et al.

(10) Patent No.: US 6,268,381 B1
(45) Date of Patent: Jul. 31, 2001

(54) TAXANE DERIVATIVES

(75) Inventors: Hideaki Shimizu; Atsuhiro Abe; Takanori Ogawa; Hiroshi Nagata; Seigo Sawada, all of Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 09/581,908

(22) PCT Filed: Dec. 16, 1998

(86) PCT No.: PCT/JP98/05681

§ 371 Date: Jun. 19, 2000

§ 102(e) Date: Jun. 19, 2000

(87) PCT Pub. No.: WO99/32473

PCT Pub. Date: Jul. 1, 1999

(30) Foreign Application Priority Data

Dec. 19, 1997 (JP) .................................................. 9-350733

(51) Int. Cl.[7] ...................... A61K 31/445; A61K 31/495; A61K 31/335; C07F 7/02; C07D 305/00

(52) U.S. Cl. ...................... 514/320; 514/254.1; 514/449; 546/14; 546/187; 544/379; 549/510

(58) Field of Search ...................... 546/14, 187; 544/379; 549/510; 514/320, 254.1, 449

(56) References Cited

U.S. PATENT DOCUMENTS

| | | |
|---|---|---|
| 6,025,385 | 2/2000 | Shimizu et al. . |
| 6,136,808 * | 10/2000 | Abe et al. ........................ 514/255 |
| 6,136,990 * | 10/2000 | Mandai et al. ................... 549/510 |
| 6,160,135 * | 12/2000 | Bouchard et al. ............... 549/510 |

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

The present invention relates to taxane derivatives each represented by the following formula (1):

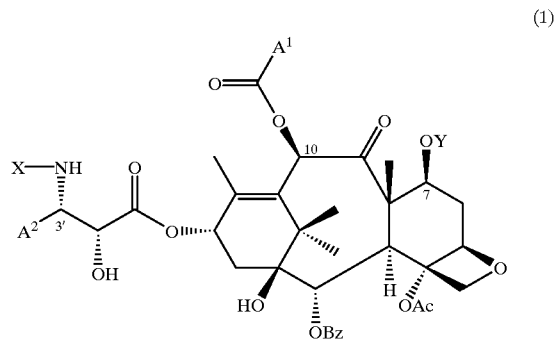

(1)

[wherein, $A^1$ represents a group

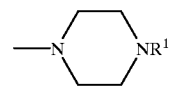

(in which $R^1$ represents H or a (substituted) alkyl group) or a group

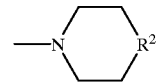

(in which $R^2$ represents an amino group, a mono- or di-alkylamino group, a piperidino group, a pyrrolidino group or a morpholino group), X represents H, an alkoxycarbonyl group or a benzoyl group, Y represents H or a trialkylsilyl group, $A^2$ represents a furyl group, an alkylfuryl group, an alkyl group or a fluorophenyl group, Ac represents an acetyl group, and Bz represents a benzoyl group] or salts thereof; and drugs containing the same as an active ingredient.

These compounds have excellent water solubility and anti-tumor activity.

6 Claims, No Drawings

TAXANE DERIVATIVES

This appln is a 371 of PCT/JP98/05681 Dec. 16, 1998.

TECHNICAL FIELD

This invention relates to taxane derivatives having excellent solubility in water, drugs containing the same and intermediates for the synthesis of the taxane derivatives.

Background Art

Taxol (registered trademark) (i) represented by the following formula (i):

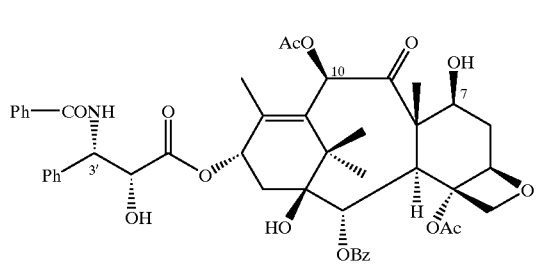

is a diterpenoid available by extraction from the bark of the Pacific yew tree, *Taxus brevifolia,* and was isolated and determined in structure for the first time in 1971 by Wall, et al. (J. Am. Chem. Soc., 93, 2325, 1971). It has been reported to exhibit high efficacy against ovarian cancer and breast cancer (Ann. int. Med. 111, 273, 1989).

Formulation of Taxol into an injection however requires a special solvent, as it is a compound sparingly soluble in water. Taxol is therefore accompanied by problems in that the production of an injection is difficult and side effects may be induced by a solvent.

A great deal of work has therefore been conducted in recent years with a view to developing a water-soluble derivative of Taxol (Nicolaou, et al., Nature, 364, 464, 1993). Under the current circumstances, however, no derivatives have been found yet to be equipped with satisfactory properties.

Accordingly, an object of the present invention is to provide a novel Taxol derivative having improved water solubility and high antimalignant tumor activities.

Disclosure of the Invention

With the foregoing circumstances in view, the present inventors have proceeded with extensive research. As a result, it has been found that a derivative of taxane (general name of the Taxol skeleton) represented by the below-described formula has water solubility and antimalignant tumor activities, each extremely higher than Taxol and is hence useful as a drug, leading to the completion of the present invention.

The present invention therefore provides a taxane derivative represented by the following formula (1):

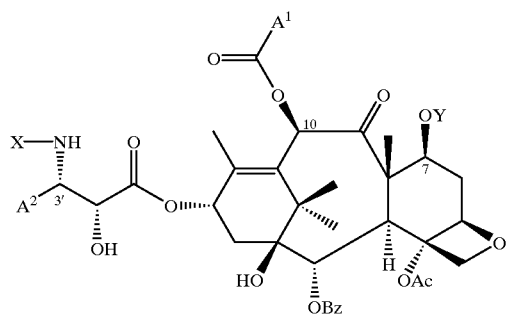

[wherein, $A^1$ represents a group

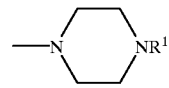

(in which $R^1$ represents a hydrogen atom, or a substituted or unsubstituted alkyl group) or a group

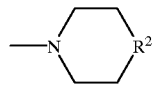

(in which $R^2$ represents an amino group, a mono- or di-alkylamino group, a piperidino group, a pyrrolidino group or a morpholino group), X represents a hydrogen atom, an alkoxycarbonyl group, an alkanoyl group which may be substituted with a fluorine atom, an alkenoyl group, a thienylcarbonyl group, to a furoyl group or a benzoyl group, Y represents a hydrogen atom or a trialkylsilyl group, $A^2$ represents a furyl group, an alkylfuryl group, an alkyl group or a fluorophenyl group, Ac stands for an acetyl group, and Bz stands for a benzoyl group] or a salt thereof.

Further, the present invention also provides a drug comprising the taxane derivative represented by the formula (1) or the salt thereof as an active ingredient.

Still further, the present invention also provides an antitumor agent comprising the taxane derivative represented by the formula (1) or the salt thereof as an active ingredient.

Still further, the present invention also provides a drug composition comprising the taxane derivative represented by the formula (1) or the salt thereof and a pharmaceutically acceptable carrier.

Still further, the present invention also provides use of the taxane derivative represented by the formula (1) or the salt thereof as a drug.

Still further, the present invention also provides use of the taxane derivative represented by the formula (1) or the salt thereof as an antitumor agent.

Still further, the present invention also provides a method for the treatment of a tumor, which comprises administering an effective amount of the taxane derivative represented by the formula (1) or the salt thereof.

BEST MODES FOR CARRYING OUT THE INVENTION

The taxane derivative according to the present invention is represented by the formula (1). In the formula (1), the alkyl group represented by $R^1$ as a substituent on the piperazino group among the groups represented by $A^1$ may be an alkyl group having 1 to 10 carbon atoms, examples of which can include methyl, ethyl, n-propyl, i-propyl, n-butyl, i-butyl, sec-butyl, tert-butyl, n-pentyl, n-hexyl, n-heptyl, n-nonyl and n-decyl groups. Of these alkyl groups, those having 1 to 6 carbon atoms, especially those having 1 to 4 carbon atoms are preferred, with methyl, ethyl and n-propyl groups being more preferred. Illustrative of substituent or substituents of the alkyl group are monoalkylaminocarbonyl groups and dialkylaminocarbonyl groups. $C_{1-6}$ alkylaminocarbonyl groups can be mentioned as more preferred monoalkylaminocarbonyl groups, and di-($C_{1-6}$ alkyl) aminocarbonyl groups can be mentioned as more preferred dialkylaminocarbonyl groups. As examples of the alkyl moiety of the mono- or di-alkylamino group represented by $R^2$ as a substituent on the piperidino group, alkyl groups similar to the above-exemplified alkyl groups represented by $R^1$ can be mentioned, with methyl, ethyl, n-propyl and i-propyl groups being preferred.

The group represented by X in the formula (1) is a hydrogen atom or an alkoxycarbonyl, alkanoyl, alkenoyl, thienylcarbonyl, furoyl or benzoyl group, of which a $C_{1-6}$ alkoxycarbonyl group is preferred with a t-butoxycarbonyl group being particularly preferred. Examples of the alkanoyl group which may be substituted with a fluorine atom include linear $C_{1-6}$ alkanoyl groups, branched $C_{1-6}$ alkanoyl groups and cyclic $C_{3-6}$ alkanoyl groups, and fluorine-substituted ones thereof. As the fluorine-substituted alkanoyl group, a trifluoroacetyl group can be mentioned. The alkyl moiety of the alkoxycarbonyl group may any be any one of linear, branched and cyclic. The group represented by Y is a hydrogen atom or a trialkylsilyl group. As the trialkylsilyl group, tri ($C_{1-6}$ alkyl)silyl groups can be mentioned. A hydrogen atom is however preferred as Y. As the alkyl moiety of the alkylfuryl group represented by $A^2$, groups similar to the above-described alkyl groups represented by $R^1$ can be mentioned, with a methyl group being particularly preferred.

Examples of the alkyl group represented by $A^2$ include linear $C_{1-6}$ alkyl groups, cyclic alkyl groups and branched alkyl groups, more specifically, ethyl, propyl, butyl, cyclic propyl, cyclic propylmethyl, t-butyl and isobutyl groups.

Illustrative of the salt of the taxane derivative (1) according to the present invention are pharmaceutically acceptable salts, for example, anion salts such as hydrochloride, bromide, iodate, tartrate, acetate, methanesulfonate, maleate, succinate and glutarate and salts with an amino acid such as arginine, lysine or alanine. Further, the taxane derivative or the salt thereof according to the present invention may exist in the form of a hydrate. The hydrate is also embraced in the present invention.

The taxane-derivative of the present invention can be prepared, for example, in accordance with the following reaction scheme.

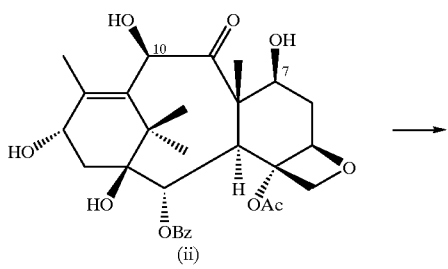

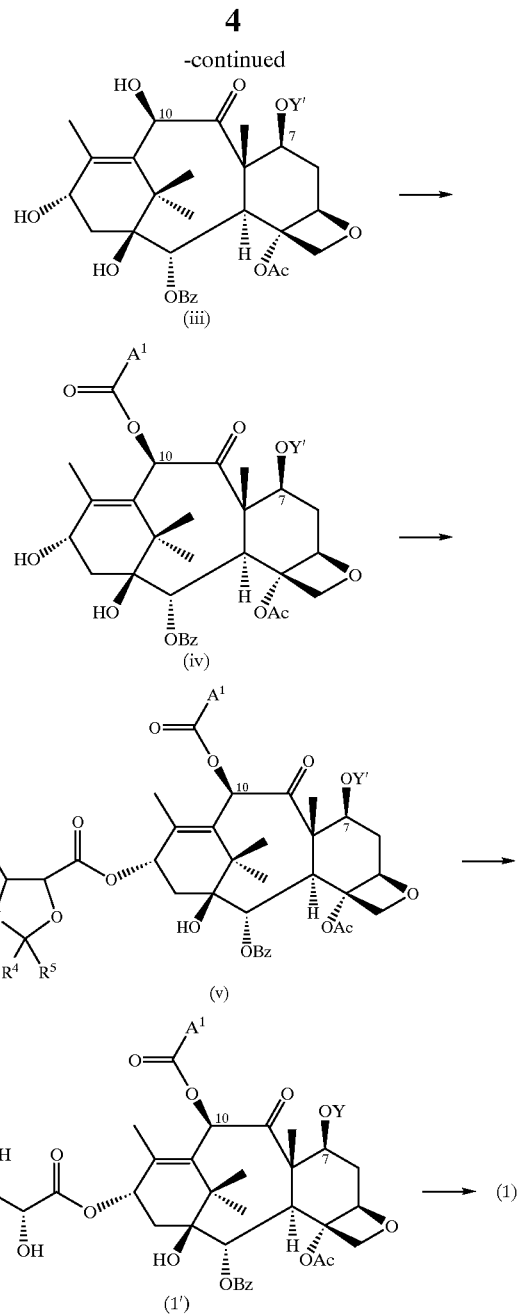

[wherein, $A^1$, $A^2$, X, Y, Ac and Bz have the same meanings as described above; X' represents a hydrogen atom or an alkoxycarbonyl group; Y' represents a trialkylsilyl group; $R^3$ represents a hydrogen atom, an alkoxycarbonyl group, an allyloxycarbonyl group or a benzyloxycarbonyl group; and $R^4$ and $R^5$ each represents a hydrogen atom, an alkyl group or an alkoxyphenyl group with the proviso that $R^4$ and $R^5$ do not represent a hydrogen atom at the same time or when either one of $R^4$ or $R^5$ represents an alkoxyphenyl group, the other one is a hydrogen atom].

Described specifically, the target taxane derivative (1) is available by providing 10-deacetylbaccatin III (ii), a known compound, as a raw material, protecting its 7-hydroxyl group with a trialkylsilyl group, introducing, into the resulting compound (iii), an A-group, which acylates (carbamoylates) it, thereby imparting it with water solubility, in order to introduce the water-solubility-imparting A-group, oxazolidinylating the 13-hydroxyl group of the resulting compound (iv), ring opening the oxazolidine ring of the resulting compound (v) and, if desired, introducing a group X into its amino group.

The protection of the 7-hydroxyl group of 10-deacetylbaccatin III can be carried out in a known manner, more specifically, by treating with a trialkylsilyl chloride in pyridine. The protecting group is a trialkylsilyl group, with a tri($C_{1-6}$ alkyl)silyl group being more preferred and a triethylsilyl group being particularly preferred.

The 10-hydroxyl group of Compound (iii) is then acylated (carbamoylated) and the side chain ($A^1$-) having a function to impart water solubility is introduced.

Examples of the acylating (carbamoylating) method can include a method making use of the above-exemplified acid derivative in the presence of a suitable base and a method making use of a condensing agent.

Illustrative of the acylating (carbamoylating) reagent usable here are acid chlorides, acid anhydrides and acid esters, and derivatives equivalent to these reagents.

As a specific method for introducing the group ($A^1$-), 4-dimethylaminopiperidinocarbonylation, for example, can be achieved by conducting treatment with 4-dimethylaminopiperidinocarbonyl chloride in the presence of a suitable base (for example, n-butyl lithium) while using a solvent such as THF.

The 13-hydroxyl group is then oxazolidinylated to obtain the compound (v). The oxazolidinylation may be conducted, for example, by reacting a derivative of oxazolidinecarboxylic acid, e.g., N-benzyloxycarbonyl (Cbz)-2,2-dimethyl-4-$A^2$-oxazolidinecarboxylic acid, N-allyloxycarbonyl-2,2-dimethyl-4-$A^2$-oxazolidinecarboxylic acid, N-alkoxycarbonyl-2-alkoxyphenyl)-4-$A^2$-oxazolidinecarboxylic acid or the like with the compound (iv) in the presence of a condensing agent such as DCC.

Next, the opening of the oxazolidine ring can be achieved by treating the resulting compound (v) with an acid in a solvent such as ethanol, thereby removing the protecting group (removing TES), and then conducting catalytic reduction in the presence of palladium-carbon, whereby the compound (1') can be obtained. Alternatively, the ring opening reaction of the oxazolidine ring can be conducted using tetra(triphenylphosphine)palladium. Deprotection may be carried out after this ring opening reaction. When an N-alkoxycarbonyl-2-(alkoxyphenyl)-4-Ar-oxazolidinecarboxylic acid is employed for the oxazolidinylation, the resulting oxazolidine ring can be opened by treating with an acid such as paratoluenesulfonic acid. In this case, the compound (1') having an alkoxycarbonyl group as $X^1$ is available.

When $X^1$ represents a hydrogen atom in the compound (1'), the invention compound (1) can be obtained by subjecting its amino group to alkoxycarbonylation, alkanoylation, alkenoylation, thienylcarbonylation or benzoylation. Here, preferred as the alkoxycarbonylation is $C_{1-6}$ alkoxycarbonylation, with t-butoxycarbonylation being particularly preferred. The t-butoxycarbonylation can be achieved, for example, by treating with t-butoxycarbonyl-4,6-dimethyl-2-mercaptopyrimidine and triethylamlne, while the alkanoylation, alkenoylation, thienylcarbonylation or benzoylation can be achieved by reacting with an acid anhydride or acid halide.

The compound which is used in the preparation process of the invention compound (1) and is represented by the following formula (2):

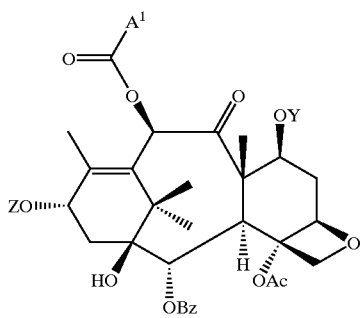

(2)

[wherein, $A^1$, Y, Ac and Bz have the same meanings as described above, Z represents a hydrogen atom or the following group:

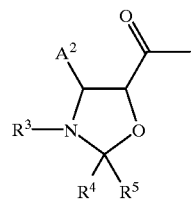

(in which $A^2_1$, $R^3$, $R^4$ and $R^5$ have the same meanings as described above)] is a novel compound and is useful as an intermediate for the synthesis of the compound (1).

Examples of the alkyl group represented by $R^4$ or $R^5$ include $C_{1-10}$, particularly, $C_{1-6}$ alkyl groups, with a methyl group being more preferred. As the alkoxyphenyl group, 4-($C_{1-6}$ alkoxy)phenyl groups are preferred, with a 4-methoxyphenyl group being particularly preferred.

The taxane derivative (1) according to the present invention was confirmed to have excellent antitumor activities in a test (Test 2) which was conducted by using, as an index, growth inhibitory effects against a cell strain KB.

As the taxane derivative and the salt thereof according to the present invention have very high solubility in water (1,000-fold or higher compared with Taxol), they can be used as drug preparations (drug compositions) such as injections without using any special solvent. As drug preparations, injections such as intravenous injections or intramuscular injections are preferred. In addition to such injections, they can also be formulated into liquid preparations such as inhalations, syrups or emulsions; solid preparations such as tablets, capsules or granules; or external preparations such as ointments or suppositories.

These preparations may generally contain pharmaceutically acceptable carriers, such as dissolution aids, stabilizers, humectants, emulsifiers, absorption enhancers and surfactants, as needed. Illustrative of the other carriers are injection-grade distilled water, Ringer's injection, glucose, sucrose syrup, gelatin, edible oil, cacao butter, magnesium stearate, and talc.

The amount of the taxane derivative (1) contained in each of the above-described respective drug preparation varies depending on the conditions of a patient to whom the drug preparation is administered, its preparation form and the like. In general, however, its amount per unit dosage form may desirably range from about 0.5 to 100 mg in the case of injections, from about 5 to 1,000 mg in the case of oral preparations and from about 5 to 1,000 mg in the case of suppositories. Further, the daily dosage of the drug having the above-described dosage forms varies depending on the condition, body weight, age, sex and the like of each patient and cannot be determined in a wholesale manner. Nonetheless, the daily dosage may generally be about 0.1 to 50 mg/kg, preferably about 1 to 20 mg/kg per adult. It is preferred to administer this dosage as a single dose or in divided dosage forms, two to four times a day.

EXAMPLES

The present invention will next be described in further detail by Examples. It should however be borne in mind that the present invention is not limited to or by them.

Example 1

10—O—(4-Piperidinopiperidinocarbonyl)-13-0-[3-(tert-butoxycarbonyl)-4-(3-furyl)-2-(4-methoxyphenyl)-5-oxazolidinecarbonyl]-7-0-triethylsilyl-10-deacetylbaccatin III (Compound 2-1)

In toluene (20 mL) was dissolved 10—O—(4-piperidinopiperidinocarbonyl)-7—O—triethylsilyl-10-deacetylbaccatin III (100 mg, 0.117 mmol) and 3-(tert-butoxycarbonyl)-4-(3-furyl)-2-(4-methoxyphenyl)-5-oxazolidinecarboxylic acid (228 mg, 0.59 mmol), followed by the addition of DCC (133 mg, 0.64 mmol) and dimethylaminopyridine (10 mg). The resulting mixture was stirred at room temperature for 3 hours in an argon gas atmosphere. From the reaction mixture, the precipitate was removed by filtration. A saturated sodium bicarbonate solution was added to the filtrate and the resulting mixture was extracted with ethyl acetate. The organic layer was washed with a saturated sodium chloride solution, dried over anhydrous sodium sulfate, and concentrated to dryness under reduced pressure. The residue was purified by chromatography on a silica gel column [chloroform-methanol mixture [98:2]). Fractions providing a TLC single spot thus eluted were combined, followed by concentration to dryness under reduced pressure, whereby the title compound (120 mg, 90%) was obtained.

$^1$H—NMR(CDCl$_3$) δ: 0.58–0.65(6H,m,Si—CH$_2$×3), 0.93 (9H,t,J=7 Hz,-Me ×3), 1.23(6H,s,C$_{16}$-Me and C$_{17}$-Me), 1.32 (9H,s,t-Bu), 1.41–1.74(8H,m), 1.69(3H,s,C$_{19}$-Me), 1.80–1.95(1H,m), 1.89(1H,m,C$_6$—H), 2.11(3H,s,C$_{18}$-Me), 2.17(3H,s,C$_4$—OAc), 2.27(2H,m,C$_{14}$—H), 2.49–3.05(8H, m), 2.53(1H,m,C$_6$—H), 3.83(3H,s,OMe), 3.86(1H,d,J=7 Hz,C$_3$—H), 4.10–4.53(2H,m), 4.15(1H,d,J=8 Hz,C$_{20}$—H), 4.28(1H,d,J=8 Hz,C$_{20}$—H), 4.49(1H,dd,J=6 Hz,10 Hz,C$_7$—H), 4.84(1H,s), 4.92(1H,d,J=8 Hz,C$_5$—H), 5.36(1H,s), 5.66 (1H,d,J=7 Hz,C$_2$—H), 6.32(1H,t,J=8 Hz,C$_{13}$—H), 6.40(3H, m,C$_{10}$—H,furyl—H,oxazolidine—H) 6.88–6.91(2H,m, ArH), 7.32–7.64(5H,m,ArH), 8.06–8.08(2H,m,ArH).

SIMS m/z: 1224(M+H)$^+$

Example 2

13-0-[3-(tert-Butoxycarbonylamino)-3-(3-furyl)-2-hydroxypropionyl]-10-0-(4-piperidinopiperidinocarbonyl)-10-deacetylbaccatin III (Compound 1-1)

Compound (2-1) (60 mg, 0.049 mmol) obtained in Example 1 was dissolved in methanol (9 mL), followed by the addition of p-toluenesulfonic acid (25 mg, 0.146 mmol). The resulting mxiture was stirred at room temperature for 12 hours. After a saturated sodium bicarbonate solution was added to the reaction mixture, the resulting mixture was extracted with chloroform. The organic layer was dried over anhydrous sodium sulfate and then concentrated to dryness under reduced pressure. The residue was purified by chromatography on a silica gel column (chloroform-methanol= 95:5) and then, purified further by reverse-phase high-performance liquid chromatography (eluent: 10 mM potassium dihydrogenphosphate—acetonitrile (1:1)], whereby the title compound (22 mg, 46%) was obtained as a colorless solid.

$^1$H—NMR(CDCl$_3$) δ: 1.14(3H,s,C$_{17}$ or C$_{16}$,-Me), 1.26 (3H,s,C$_{17}$ or C$_{16}$-Me), 1.34(9H,s,t-Bu), 1.48–1.96(9H,m), 1.67(3H,s,C$_{19}$-Me), 1.89(3H,s), 2.35(3H,s,C$_4$—OAc), 2.35 (1H,m ,C$_{14}$—H), 2.50–2.58(1H,m,C$_6$—H), 2.52–3.47(8H, m), 3.81(1H,d,J=6 Hz,C$_3$—H), 4.17–4.32(2H,m), 4.18(1H, d,J=8 Hz,C$_{20}$—H), 4.31(1H,d,J=8 Hz,C$_{20}$—H), 4.44(1H,m, C$_7$—H), 4.54(1H,s,C$_2$,—H), 4.97(1H,d,J=8 Hz,C$_5$—H), 5.10–5.12(1H,m), 5.20(1H,d,J=10 Hz,C$_3$,—H), 5.67(1H,d, J=7 Hz,C$_2$—H), 6.25(1H,t,J=8 Hz,C$_{13}$—H), 6.26(1H,s, C$_{10}$—H), 6.45(1H,s,furyl H), 7.42–7.65(5H,m,ArH), 8.10–8.14(2H,m,ArH).

SIMS m/z:992(M+H)$^+$

Example 3

13-0-[3-Benzyloxycarbonyl-2,2-dimethyl-4-(3-furyl)-5-oxazolidinecarbonyl]-10-0-(4-methylpiperazinocarbonyl)-7-0-triethylsilyl-10-deacetylbaccatin III (Compound 2-2)

In a similar manner to Example 1, the reaction and after-treatment were conducted by using 10-0-(4-methylpiperazinocarbonyl)-7-0-triethylsilyl-10-deacetylbaccatin III (100 mg, 0.127 mmol) and 3-benzyloxycarbonyl-2,2-dimethyl-4-(3-furyl)-5-oxazolidinecarboxylic acid (200 mg, 0.57 mmol), whereby the title compound (60 mg, 43%) was obtained.

$^1$H—NMR(CDCl$_3$) δ: 0.56–0.62(6H,m,Si—CH$_2$×3), 0.93 (9H,t,J=8 Hz,-Me×3), 1.19(3H,s,C$_{16}$-Me or C$_{17}$-Me), 1.20 (3H,s,C$_{16}$-Me or C$_{17}$-Me), 1.66–1.72(9H,m,C$_{19}$-Me and oxazolidine Me×2), 1.80–1.94(1H,m), 2.13(6H,m,Cl$_{18}$-Me and C$_4$—OAc), 2.22(2H,m,C$_{14}$—H), 2.32(3H,s,N-Me), 2.39–2.55(5H,m), 3.38–3.90(4H,m), 3.84(1H,d,J=7 Hz,C$_3$—H), 4.14(1H,d,J=8 Hz,C$_{20}$—H), 4.29(1H,d,J=8 Hz,C$_{20}$—H), 4.47(1H,dd,J=7 Hz, 11 Hz,C$_7$—H), 4.60(1H, s), 4.93(1H,d,J=8.1 Hz,C$_5$—H), 5.38(1H,s), 5.67(1H,d,J=7 Hz,C$_2$—H), 6.22(1H,t,J=8 Hz,C$_{13}$—H), 6.39(3H,m,C$_{10}$—H, and furyl—H), 7.27–7.64(10H,m,ArH), 8.05–8.08(2H, m,ArH).

Example 4

13-0-[3-tert-Butoxycarbonylamino)-3-(3-furyl)-2-hydroxypropionyl]-10-0-(4-methylpiperazinocarbonyl)-10-deacetylbaccatin III (Compound 1-2)

Compound (2-2) (50 mg, 0.045 mmol) obtained in Example 3 was dissolved in ethanol (16 mL), followed by the addition of 0.1N-hydrochloric acid (4.5 mL). The resulting mixture was stirred at room temperature for 17 hours. The solvent was distilled off under reduced pressure and to the residue, a saturated aqueous solution of sodium bicarbonate was added. The resulting mixture was extracted with chloroform. The organic layer was dried over sodium sulfate and then concentrated to dryness under reduced pressure. Methanol (5 mL), water (0.5 mL) and 10% palladium-activated carbon (20 mg) were added to the residue, followed by stirring at normal temperature and normal pressure for 3 hours in a hydrogen gas atmosphere. The reaction mixture was filtered and the filtrate was concentrated to dryness under reduced pressure. A saturated sodium bicarbonate solution was added to the residue and the resulting mixture was extracted with ethyl acetate. The organic layer was dried over sodium sulfate and concentrated to dryness under reduced pressure, whereby a residue (28 mg) was obtained. The residue was dissolved in tetrahydrofuran (8 mL), followed by the addition of sodium bicarbonate (20 mg) and di-tert-butyl dicarbonate (9 mg, 0.04 mmol). The resulting mixture was stirred at room temperature for 20 hours. A saturated sodium bicarbonate solution was added to the reaction mixture and the resulting mixture was extracted with ethyl acetate. The organic layer was washed with a saturated sodium chloride solution, dried over sodium sulfate and concentrated to dryness under reduced pressure. The residue was purified by chromatography on a silica gel column [chloroform-methanol (95:5)] and then, purified further by reverse-phase high-performance liquid chromatography [eluent: 10 mM potassium dihydrogenphosphate—acetonitrile (3:2)], whereby the title compound (10 mg, 23%) was obtained as a colorless solid.

$^1$H—NMR(CDCl$_3$) δ: 1.15(3H,s,C$_{17}$ or C$_{16}$-Me), 1.26 (3H,s,C$_{17}$ or C$_{16}$-Me), 1.34(9H,s,t-Bu), 1.68(3H,s,C$_{19}$-Me), 1.89(1H,m), 1.90(3H,s,C$_{18}$-Me), 2.35(6H,s,C$_4$—OAc and N-Me), 2.35(2H,m,C$_{14}$—H), 2.42–2.58(5H,m), 3.40–3.75 (4H,m), 3.81(1H,d,J=7 Hz,C$_3$—H), 4.18(1H,d,J=9 Hz,C$_{20}$—H), 4.31(1H,d,J=9 Hz,C$_{20}$—H), 4.44(1H,dd,J=7 Hz,11 Hz,C$_7$—H), 4.54(1H,d,J=2 Hz,C$_2$,—H), 4.97(1H,d,J=8 Hz,C$_5$—H), 5.11(1H,d,J=10 Hz), 5.20(1H,d,J=10 Hz), 5.67(1H,d,J=7 Hz,C$_2$—H), 6.24(1H,t,J=8 Hz,C$_{13}$—H), 6.28 (1H,s,C$_{10}$—H), 6.45(1H,s,furyl H), 7.43–7.44(1H,m,ArH), 7.48–7.52(3H,m,ArH), 7.58–7.62(1H,m,ArH), 8.10–8.14 (2H,m,ArH).

SIMS m/z:924(M+H)$^+$

Example 5

13-0-[3-Benzyloxycarbonyl-2,2-dimethyl-4-(2-furyl)-5-oxazolidinecarbonyl]-10-0-(4-dipropylaminopiperidinocarbonyl)-7-0-triethylsilyl-10-deacetylbaccatin III (Compound 2-3)

The reaction and after-treatment were conducted in a similar manner to Example 1 by using 10-0-(4-dipropylaminopiperidinocarbonyl)-7-0-triethylsilyl-10-deacetylbaccatin III (100 mg, 0.127 mmol) and 3-benzyloxycarbonyl-2,2-dimethyl-4-(2-furyl)-5-oxazolidinecarboxylic acid (183 mg, 0.52 mmol), whereby the title compound (130 mg, 93%) was obtained.

$^1$H—NMR(CDCl$_3$) δ: 0.55–0.63(6H,m,Si—CH$_2$×3), 0.86 (9H,t,J=8 Hz,-Me×3), 0.87(6H,m), 1.19(3H,s,C$_{16}$-Me or C$_{17}$-Me), 1.21(3H,s,C$_{16}$-Me or C$_{17}$-Me), 1.30–1.80(8H,m), 1.67(3H,s,C$_{19}$-Me), 1.70–1.80(6H,m,oxazolidine Me×2), 1.80–1.94(1H,m), 2.13(3H,s,C$_{18}$-Me or C$_4$—OAc), 2.17 (3H,s,C$_{18}$-Me or C$_4$—OAc), 2.22(2H,m,C$_{14}$—H), 2.35–3.02(7H,m), 2.50(1H,m,C$_6$—H), 3.85(1H,d,J=7 Hz,C$_3$—H), 4.06–4.51(2H,m), 4.13(1H,d,J=8 Hz,C$_{20}$—H), 4.29(1H,d,J=8 Hz,C$_{20}$—H), 4.47(1H,dd,J=7 Hz,11 Hz,C$_7$—H), 4.78(1H,s), 4.92(1H,d,J=8 Hz,C$_5$—H), 4.93–5.20(2H,m), 5.43(1H,s), 5.67(1H,d,J=7 Hz,C$_2$—H), 6.20(1H,m,C$_{13}$—H), 6.30–6.42(2H,m,C$_{10}$—H, and furyl—H), 7.10–7.50(8H,m,ArH), 7.59–7.63(1H,m,ArH), 8.05–8.08 (2H,m,ArH).

Example 6

13-0-[3-(tert-Butoxycarbonylamino)-3-(2-furyl)-2-hydroxypropionyl]-10-0-(4-dipropylaminopiperidinocarbonyl)-10-deacetylbaccatin III (Compound 1-3)

The reaction and after-treatment were conducted as in Example 4 by using Compound (2-3) (140 mg, 0.118 mmol) obtained in Example 5, followed by purification by reverse-phase high-performance liquid chromatography [eluent: 10 mM potassium dihydrogenphosphate—acetonitrile (3:2)], whereby the title compound (34 mg, 30%) was obtained as colorless crystals.

$^1$H—NMR(CDCl$_3$) δ: 0.84–0.94(6H/m), 1.15(3H,s,C$_{17}$ or C$_{16}$-Me), 1.26(3H,s,C$_{17}$ or C$_{16}$-Me), 1.34–1.99(7H,m), 1.35(9H,s,t-Bu), 1.68(3H,s,C$_{19}$-Me), 1.89(1H,m), 1.91(3H, s,C$_{18}$-Me), 2.25–3.10(7H,m), 2.35(2H,m,C$_{14}$—H), 2.40(3H, s,C$_4$—OAc), 2.55(1H,m), 3.82(1H,d,J=7 Hz,C$_3$—H), 4.10–4.32(2H,m), 4.18(1H,d,J=9 Hz,C$_{20}$—H), 4.31(1H,d, J=9 Hz,C$_{20}$—H), 4.44(1H,m,C$_7$—H), 4.72(1H,s,C$_2$,—H), 4.98(1H,d,J=8 Hz,C$_5$—H), 5.22(1H,d,J=10 Hz), 5.35(1H,d, J=10 Hz), 5.67(1H,d,J=7 Hz,C$_2$—H), 6.25(1H,br-t,C$_{13}$—H), 6.27(1H,s,C$_{10}$—H), 6.31–6.33(1H,m,furyl H), 6.37–6.38 (1H,m,furyl H), 7.41–7.42(1H,m,ArH), 7.48–7.52(3H,m, ArH), 7.58–7.62(1H,m,ArH), 8.11–8.14(2H,m,ArH).

SIMS m/z:1008(M+H)$^+$

Example 7

13-0-[3-Benzyloxycarbonyl-2,2-dimethyl-4-(2-furyl)-5-oxazolidinecarbonyl]-10-0-(4-ethylpiperazinocarbonyl)-7-0 triethylsilyl-10-deacetylbaccatin III (Compound 2-4)

The reaction and after-treatment were conducted in a similar manner to Example 1 by using 10-0-(4-ethylpiperazinocarbonyl)-7-0-triethylsilyl-10-deacetylbaccatin III (100 mg, 0.125 mmol) and 3-benzyloxycarbonyl-2,2-dimethyl-4-(2-furyl)-5-oxazolidinecarboxylic acid (195 mg, 0.56 mmol), whereby the title compound (140 mg, 99%) was obtained.

$^1$H—NMR(CDCl$_3$) δ: 0.55–0.62(6H,m,Si—CH$_2$×3), 0.92 (9H,t,J=8 Hz,-Me×3), 1.11(3H,t,J=7 Hz,-Et), 1.19(3H,s,C$_{16}$-Me or C$_{17}$-Me), 1.20(3H,s,C$_{16}$-Me or C$_{17}$-Me), 1.30–1.40 (1H,m), 1.67(3H,s,C$_{19}$-Me), 1.73(6H,m,oxazolidine Me×2), 1.82–1.97(2H,m), 2.13(3H,s,C$_{18}$-Me or C$_4$—OAc), 2.17 (3H,s,C$_{18}$-Me or C$_4$—OAc), 2.22(2H,m), 2.40–2.56(4H,m), 2.45(2H,q,J=7 Hz,-Et), 3.33–3.92(4H,m), 3.85(1H,d,J=7 Hz,C$_3$—H), 4.13(1H,d,J=8 Hz,C$_{20}$—H), 4.28(1H,d,J=8 Hz,C$_{20}$—H), 4.47(1H,dd,J=7 Hz,11 Hz,C$_7$—H), 4.63(1H,s), 4.92(1H,d,J=8 Hz,C$_5$—H), 4.93–5.20(2H,m), 5.43(1H,s), 5.67(1H,d,J=7 Hz,C$_2$—H), 6.20(1H,t,J=8 Hz,C$_{13}$—H), 6.34 (2H,br-s,furyl—H), 6.39(1H,s,C$_{10}$—H), 7.10–7.42(6H,m, ArH), 7.45–7.49(2H,m,ArH), 7.59–7.63(1H,m,ArH), 8.05–8.08(2H,m,ArH).

Example 8

13-0-[3-(tert-Butoxycarbonylamino)-3-(2-furyl)-2-hydroxypropionyl]-10-0-(4-ethylpipezinocarbonyl)-10-deacetylbaccatin III (Compound 1-4)

The reaction and after-treatment were carried out in a similar manner to Example 4, by using Compound (2-4) (140 mg, 0.124 mmol) obtained in Example 7, and the compound thus obtained was purified by reverse-phase high performance liquid chromatography [eluent: 10 mM potassium dihydrogenphosphate—acetonitrile (3:2)], whereby the title compound (60 mg, 53%) was obtained as colorless crystals.

$^1$H—NMR(CDCl$_3$) δ: 1.10–1.15(6H,m,C$_{17}$ or C$_{16}$-Me and N—Et), 1.26(3H,s,C$_{17}$ or C$_{16}$-Me), 1.35(9H,s,t-Bu), 1.68(3H,s,C$_{19}$-Me), 1.89(1H,m), 1.90(3H,s,C$_{18}$-Me), 2.35 (2H,m,C$_{14}$—H), 2.38(6H,s,C$_4$—OAc), 2.45–2.62(7H,m), 3.40–3.85(4H,m), 3.82(1H,d,J=7 Hz,C$_3$—H), 4.18(1H,d, J=9 Hz,C$_{20}$—H), 4.31(1H,d,J=9 Hz,C$_{20}$—H), 4.46(1H,dd, J=7 Hz,11z,$C_7$—H), 4.72(1H,d,J=2 Hz,$C_2$,—H), 4.98(1H,d, J=8 Hz,$C_5$—H), 5.23(1H,d,J=10 Hz), 5.35(1H,d,J=10 Hz), 5.67(1H,d,J=7 Hz,$C_2$—H), 6.25(1H,t,J=8 Hz,$C_{13}$—H), 6.28 (1H,s,$C_{10}$—H), 6.32–6.33(1H,m,furyl H), 6.38–6.39(1H,m, furyl H), 7.41–7.42(1H,m,ArH), 7.48–7.52(2H,m,ArH), 7.59–7.63(1H,m,ArH), 8.11–8.12(2H,m,ArH).

SIMS m/z: 938(M+H)$^+$

Example 9

13-0-[3-Aryloxycarbonyl-2,2-dimethyl-4-(2-furyl)-5-oxazolidinecarbonyl]-10-0-(4-methylpiperazinocarbonyl)-7-0-triethylsilyl-10-deacetylbaccatin III (Compound 2-5)

In dry toluene was dissolved 10-O-(4-methylpiperazinocarbonyl)-7-O-triethylsilyl-10-deacetylbaccatin III (138 mg, 0.18 mmol), followed by the addition of 3-allyloxycarbonyl-2,2-dimethyl-4-(2-furyl)-5-oxazolidinecarboxylic acid (93 mg, 0.31 mmol), DCC (0.18 mmol) and DMAP (0.01 mmol). The resulting mixture was stirred at room temperature for 3 hours. The reaction mixture was filtered and the filtrate was concentrated. The residue was washed with a saturated aqueous solution of sodium bicarbonate and then, extracted with chloroform. The organic layer was dried over anhydrous magnesium sulfate and concentrated to dryness under reduced pressure. The residue was purified by chromatography on a silica gel column (chloroform—methanol mixture (97:3)]. Fractions providing a TLC single spot thus eluted were collected and concentrated to dryness under reduced pressure, whereby the title compound (164 mg, 88%) was obtained.

$^1$H—NMR(CDCl$_3$) δ: 0.52–0.62(6H,m), 0.90(9H,t,J=7.93 Hz), 1.16(3H,s), 1.17(3H,s), 1.64(3H,s), 1.65(3H,s), 1.72(3H,s), 1.82(3H,s), 1.83(1H,m), 2.14(3H,s), 2.30(3H,s), 2.05–2.56(7H,m), 3.32–3.65(4H,m), 8.04(2H,d,J=8. Hz), 3.81(1H,d,J=7 Hz,$C_3$—H), 4.11(1H,d,J=8 Hz,$C_{20}$—H), 4.26 (1H,d,J=8 Hz,$C_{20}$—H), 4.38–4.61(3H,m), 4.78(1H,d,J=6 Hz), 4.91(1H,d,J=9 Hz,$C_5$—H), 5.08–5.25(2H,m), 5.53(1H, d,J=6 Hz), 5.64(1H,d,J=7 Hz,$C_2$—H), 5.73(1H,m), 6.19(1H, brs,$C_{13}$—H), 6.36(1H,s,$C_{10}$—H), 6.34–6.38(2H,m), 7.38 (1H,t,J=1 Hz), 7.54(2H,t,J=8 Hz), 7.59(1H,t,J=7 Hz)

Example 10

13-0-[3-Benzoylamino-3-(2-furyl)-2-hydroxypropionyl]-10-0-(4-methylpiperazinocarbonyl)-10-deacetylbaccatin III (Compound 1-5)

The compound (2-5) (55 mg, 0.05 mmol) obtained in Example 9 was dissolved in tetrahydrofuran (2 mL), followed by the addition of Pd(PPh$_3$)$_4$ (8 mg, 0.007 mmol) and dimedone. The resulting mxiture was stirred for 12 hours at room temperature. After the solvent was distilled off under reduced pressure and the residue was dissolved in ethanol, 0.1N-hydrochloric acid (2.5 mL) was added to the resulting solution. The mixture was stirred at room temperature for 36 hours. The reaction mixture was washed with a saturated aqueous solution of sodium bicarbonate and then extracted with chloroform. The organic layer was dried over anhydrous magnesium sulfate and distilled under reduced pressure to remove the solvent. To the residue, methylene chloride (3 mL), benzoic anhydride (9 mg, 0.04 mmol) and triethylamine (4 mg, 0.04 mmol) were added, followed by stirring in ice bath for 3 hours. The solvent was distilled off under reduced pressure. The residue was then purified by chromatography on a silica gel column [a chloroform—methanol mixture (95:5)] and purified further by reverse-phase high-performance liquid chromatography [eluent: 10 mM potassium dihydrogenphosphate—acetonitrile (1:1)], whereby the title compound (40 mg, 85%) was obtained as colorless crystals.

$^1$H—NMR(CDCl$_3$) δ: 1.06(3H,s), 1.17(3H,s), 1.62(3H,s), 1.80(1H,m), 1.83(3H,s), 2.18–2.65(7H,m), 2.33(3H,s), 2.37 (3H,s), 2.98(1H,brs), 3.32–3.70(4H,m), 3.75(1H,d,J=7 Hz,$C_3$—H), 4.13(1H,d,J=9 Hz,$C_{20}$—H), 4.25(1H,d,J=8 Hz,$C_{20}$—H), 4.38(1H,m,$C_7$—H), 4.76(1H,d,J=2 Hz,$C_2$,—H), 4.90(1H,d,J=10 Hz,$C_5$—H), 5.61(1H,d,J=7 Hz,$C_2$—H), 5.83(1H,dd,J=9 Hz,2 Hz,$C_3$,—H), 6.20(1H,t,J=9 Hz,$C_{13}$—H), 6.33–6.34(2H,m), 6.21(1H,s,$C_{10}$—H), 6.80(1H,d,J=9 Hz,NH), 7.32–7.39(6H,m), 7.44(2H,t,J=8 Hz), 7.54(1H,t, J=7 Hz), 7.68(2H,d,J=7 Hz), 8.07(2H,d,J=7 Hz).

SIMS m/z 928(M+H)$^+$

Example 11

13-0-[3-(2-Furyl)-2-hydroxy-3-n-pentylcarbonylaminopropionyl]-10-0-(4-methylpiperazinocarbonyl)-10-deacetylbaccatin III (Compound 1-6)

In a similar manner to Example 10, the reaction and after-treatment were conducted by using Compound (2-5) (55 mg, 0.05 mmol) of Example 9 and n-pentylcarbonyl chloride(5 mg, 0.04 mmol), whereby the title compound (8 mg, 35%) was obtained as colorless crystals.

$^1$H—NMR(CDCl$_3$) δ: 0.77(3H,t,J=7 Hz), 1.07(3H,s), 1.19(3H,s), 1.16–1.22(4H,m), 1.49(2H,m), 1.61(3H,s), 1.79 (1H,m), 1.83(3H,s), 2.32(3H,s), 2.35(3H,s), 2.64–2.08(9H, m), 3.00(1H,s), 3.70–3.30(4H,m), 3.73(1H,d,J=7 Hz,$C_3$—H), 4.12(1H,d,J=9 Hz,$C_{20}$—H), 4.24(1H,d,J=8 Hz,$C_{20}$—H), 4.38(1H,m,$C_7$—H), 4.66(1H,d,J=2 Hz,$C_2$,—H), 4.90(1H,d, J=7 Hz,$C_5$—H), 5.58–5.63(2H,m), 6.06(1H,d,J=9 Hz,NH), 6.16(1H,t,J=9 Hz,$C_{13}$—H), 6.21(1H,s,$C_{10}$—H), 6.26(1H,d, J=3 Hz), 6.32(1H,dd,J=3 Hz,2 Hz), 7.36(1H,d,J=1 Hz), 7.44(2H,t,J=8 Hz), 7.54(1H,t,J=7 Hz), 8.05(2H,d,J=7 Hz).

MS m/z 922[M+H]$^+$

Example 12

13-0-[3-(2-Furyl)-2-hydroxy-3-(thenoylamino) propionyl]-10-0-(4-methylpiperazinocarbonyl)-10-deacetylbaccatin III (Compound 1-7)

In a similar manner to Example 10, the reaction and after-treatment were conducted by using Compound (2-5) (55 mg, 0.05 mmol) of Example 9 and 2-thenoyl chloride (6 mg, 0.04 mmol), whereby the title compound (3 mg, 12%) was obtained as colorless crystals.

$^1$H—NMR(CDCl$_3$) δ: 1.05(3H,s), 1.19(3H,s), 1.62(3H,s), 1.83(3H,s), 1.85(m,1H), 2.33(3H,s), 2.35(3H,s), 2.21–2.97 (7H,m), 3.59(1H,s), 3.37–3.98(4H,m), 3.74(1H,d,J=7 Hz,$C_3$—H), 4.13(1H,d,J=9 Hz,$C_{20}$—H), 4.24(1H,d,J=9 Hz,$C_{20}$—H), 4.38(1H,m,$C_7$—H), 4.76(1H,d,J=2 Hz,$C_2$,—H), 4.89(1H,d,J=8 Hz,$C_5$—H), 5.60(1H,d,J=7 Hz,$C_2$—H), 5.79(1H,dd,J=9 Hz,2 Hz,$C_3$, —H), 6.19(1H,t,J=9 Hz,$C_{13}$—H), 6.21(1H,s,$C_{10}$—H), 6.32–6.35(2H,m), 6.68(1H,d,J=9 Hz,NH), 7.00(1H,dd,J=5 Hz,4 Hz), 7.38–7.48(5H,m), 7.56 (1H,t,J=7 Hz), 8.07(2H,d,J=7 Hz).

MS m/z 932[M+H]$^+$

Example 13

13-0-[3-Aryloxycarbonyl-2,2-dimethyl-4-(2-furyl)-5-oxazolidinecarbonyl]-10-0-(4-morpholinopiperidinocarbonyl)-7-0-triethylsilyl-10-deacetylbaccatin III (Compound 2-6)

In a similar manner to Example 9, the title compound (85 mg, 100%) was obtained from 10-0-(4- morpholinopiperidinocarbonyl)-7-0-triethylsilyl-10-deacetylbaccatin III (64 mg, 0.075 mmol) and 3-aryloxycarbonyl-2,2-dimethyl-4-(2-furyl)-5-oxazolidinecarboxylic acid (30 mg, 0.1 mmol).

$^1$H—NMR(CDCl$_3$) δ: 0.53–0.59(6H,m), 0.90(9H,t,J=8 Hz), 1.14(3H,s), 1.17(3H,s), 1.64(3H,s), 1.65(3H,s), 1.72 (3H,s), 1.82(3H,s), 1.30–1.93(5H,m), 2.13(3H,s), 2.00–3.09 (10H,m), 3.62–3.75(4H,m), 3.80(1H,d,J=7 Hz,C$_3$—H), 4.10 (1H,d,J=8 Hz,C$_{20}$—H), 4.10–4.60(5H,m), 4.25(1H,d,J=8 Hz,C$_{20}$—H), 4.78(1H,d,J=6 Hz), 4.90(1H,d,J=10 Hz,C$_5$—H), 5.24–5.06(2H,m), 5.64(1H,d,J=7 Hz,C$_2$—H), 5.73(1H, brs), 6.17(1H,brs,C$_{13}$—H), 6.30–6.37(2H,m), 6.35(1H,s, C$_{10}$—H), 7.38(1H,d,J=1 Hz), 7.46(2H,t,J=8 Hz), 7.59(1H, t,J=7 Hz), 8.04(2H,d,J=8 Hz).

Example 14

13-0-[3-(3,3-Dimethylacryloylamino)-3-(2-furyl)-2-hydroxypropionyl]-10-0-(4-morpholinopiperidinocarbonyl)-10-deacetylbaccatin III (Compound 1-8)

In a similar manner to Example 10, the reaction and after-treatment were conducted by using Compound (2-6) (42 mg, 0.037 mmol) of Example 13 and 3,3-dimethylacryloyl chloride (S mg, 0.04 mmol), whereby the title compound (9 mg, 25%) was obtained as colorless crystals.

$^1$H—NMR(CDCl$_3$) δ: 1.07(3H.s), 1.19(3H.s), 1.32–2.00 (5H,m), 1.60(3H.s), 1.76(3H.s), 1.83(3H.s), 1.95(3H.s), 2.15–3.10(10H,m), 2.35(3H.s), 3.25–3.95(4H,m), 4.11(1H, d,J=9 Hz,C$_{20}$—H), 4.10–4.27(2H,m), 4.24(1H,d,J=8 Hz,C$_{20}$—H), 4.38(1H,m,C$_7$—H), 4.86(1H,brs,C$_2$, —H), 4.90(1H,d,J=8 Hz,C$_5$—H), 5.52(1H,s), 5.62(1H,brs,C$_3$,—H), 5.67(1H,d,J=7 Hz,C$_2$—H), 6.16(1H,brs,C$_{13}$—H), 6.20 (1H,s,C$_{10}$—H), 6.26(1H,d,J=3 Hz), 6.31(1H,dd,J=3 Hz,2 Hz), 7.36(1H,d,J=2 Hz), 7.43(2H,t,J=7 Hz), 7.54(1H,t,J=7 Hz), 8.05(2H,d,J=7 Hz).

MS m/z 976[M+H]$^+$

Example 15

13-0-[3-Benzyloxycarbonyl-2,2-dimethyl-4-(4-fluorophenyl)-5-oxazolidinecarbonyl]-10-0-(4-methylpiperazinocarbonyl)-7-0-triethylsilyl-10-deacetylbaccatin III (Compound 2-7)

In a similar manner to Example 1, the reaction and after-treatment were conducted using 10-0-(4-methylpiperazinocarbonyl)-7-0-triethylsilyl-10-deacetylbaccatin III (100 mg, 0.128 mmol) and 3-benzyloxycarbonyl-2,2-dimethyl-4-(4-fluorophenyl)-5-oxazolidinecarboxylic acid (191 mg, 0.512 mmol), whereby the title compound (118 mg, 81%) was obtained as colorless crystals.

$^1$H—NMR(CDCl$_3$) δ: 0.53–0.63(6H,m), 0.93(9H,t,J=8 Hz), 1.17(3H,s), 1.20(3H,s), 1.55–1.61(3H,m), 1.66(3H,s), 1.75(3H,s), 1.80–1.92(2H,m), 1.81(3H,s), 1.96(3H,s), 2.08 (3H,s), 2.17(2H,d,J=9 Hz), 2.48–2.66(m,5H), 3.55–3.80(m, 4H), 3.79(1H,d,J=7 Hz), 4.10(1H,d,J=9 Hz), 4.27(1H,d,J=9 Hz), 4.43–4.47(m,2H), 4.80–5.03(m,1H), 4.88–4.90(1H,m), 5.21(brs,1H), 5.65(1H,d,J=7 Hz), 6.23(1H,t,J=10 Hz), 6.39 (1H,s), 6.83(1H,brs), 7.00–7.29(m,9H), 7.49(2H,t,J=8 Hz), 7.63(1H,t,J=7 Hz), 8.04(2H,d,J=7 Hz).

SI-MS m/z: 1140[M+H]$^+$

Example 16

13-0-[3-(tert-Butoxycarbonylamino)-3-(4-fluorophenyl)-2-hydroxypropionyl]-10-0-(4-methylpiperazinocarbonyl)-10-deacetylbaccatin III (Compound 1-9)

Compound (2-7) (110 mg, 0.097 mmol) obtained in Example 15 was dissolved in ethanol (30 mL), followed by the addition of 0.1N hydrochloric acid (9.7 mL, 0.97 mmol) under ice cooling and stirring. The resulting mixture was stirred at room temperature for 3 days. The solvent was distilled off under reduced pressure and to the residue, a saturated aqueous solution of sodium bicarbonate was added. The resulting mixture was extracted with chloroform. The organic layer was washed with water and saturated saline, dried over anhydrous sodium sulfate and then distilled under reduced pressure to remove the solvent. The residue was purified by chromatography on a silica gel column [a chloroform—methanol mixture (30:1)]. Methanol (10 mL), water (1 mL) and 10%, palladium-carbon (31 mg, 0.029 mmol) were added to the residue, followed by vigorous stirring at normal temperature and normal pressure for 3 hours in a hydrogen gas atmosphere. The reaction mixture was filtered and the filtrate was concentrated to dryness under reduced pressure. A saturated sodium bicarbonate solution was added to the residue and the resulting mixture was extracted with ethyl acetate. The organic layer was washed with water and saturated saline, dried over anhydrous sodium sulfate and then concentrated to dryness under reduced pressure, whereby a colorless oil (80 mg, 88%) was obtained. The oil was dissolved in tetrahydrofuran (20 mL), followed by the addition of sodium bicarbonate (74 mg, 0.88 mmol) and di-tert-butyl dicarbonate (23 mg, 0.106 mmol). The resulting mixture was stirred at room temperature for 19 hours. A saturated sodium bicarbonate solution was added to the reaction mixture and the resulting mixture was extracted with ethyl acetate. The organic layer was washed with a saturated sodium chloride solution, dried over sodium sulfate and concentrated to dryness under reduced pressure. The residue was purified by chromatography on a silica gel column [a chloroform-methanol mixture (50:1)] and then, purified further by reverse-phase high-performance liquid chromatography [eluent: 10 mM potassium dihydrogenphosphate—acetonitrile (55:45)], whereby the title compound (15 mg, 18%) was obtained as a colorless solid.

$^1$H—NMR(CDCl$_3$) δ: 1.14(3H,s), 1.26(3H,s), 1.33(9H,s), 1.68(3H,s), 1.85–1.92(m,5H), 2.25(3H,m), 2.37(3H,s), 2.44 (3H,s), 2.50–2.63(4H,m), 3.45–3.80(m,4H), 3.80(1H,d,J=7 Hz), 4.18(1H,d,J=8 Hz), 4.31(1H,d,J=8 Hz), 4.44(1H,dd,J= 7,11 Hz), 4.60(1H,s), 4.94–4.97(1H,m), 5.24–5.26(1H,m), 5.38–5.40(1H,m), 5.66(1H,d,J=7 Hz), 6.24–6.28(1H,m), 6.28(1H,s), 7.06–7.11(2H,m), 7.36–7.39(2H,m), 7.50(2H,t, J=8 Hz), 7.59–7.63(1H,m), 8.11 (2H,d,J=7 Hz).

SI-MS m/z: 952[M+H]

Example 17

13-0-[3-Benzyloxycarbonyl-2,2-dimethyl-4-(2-furyl)-5-oxazolidinecarbonyl]-10-0-(4-methylpiperazinocarbonyl)-7-0-triethysilyl-10-deacetylbaccatin III (Compound 2-8)

In a similar manner to Example 1, the reaction and after-treatment were conducted using 10-0-(4-methylpiperazinocarbonyl)-7-0-triethysilyl-10-deacetylbaccatin III (100 mg, 0.127 mmol) and 3-benzyloxycarbonyl-2,2-dimethyl-4-(2-furyl)-5-oxazolidinecarboxylic acid (190 mg, 0.55 mmol), whereby the title compound (140 mg, 99%) was obtained.

$^1$H—NMR(CDCl$_3$) δ: 0.56–0.62(6H,m,Si—CH$_2$×3), 0.93 (9H,t,J=8 Hz,-Me×3), 1.19(6H,s,C$_{16}$-Me and C$_{17}$-Me), 1.66–1.73(9H,m,C$_{19}$-Me and oxazolidine Me×2), 1.82–1.92 (1H,m), 2.05(3H,s), 2.13(3H,s), 2.22(2H,m,C$_{14}$—H), 2.39–2.55(5H,m), 2.41(3H,s), 3.39–3.99(4H,m), 3.84(1H,d, J=7 Hz,$C_3$—H), 4.14(1H,d,J=8 Hz,$C_{20}$—H), 4.28(1H,d,J=8 Hz,$C_{20}$—H), 4.47(1H,dd,J=7 Hz,11 Hz,$C_7$—H), 4.78(1H,s), 4.93(1H,d,J=8 Hz,$C_5$—H), 4.95–5.18(2H,m), 5.45(1H,s), 5.66(1H,d,J=7 Hz,$C_2$—H), 6.22(1H,t,J=8 Hz,$C_{13}$—H), 6.34 (2H,m), 6.39(3H,s,$C_{10}$—H), 7.10–7.40(6H,m,ArH), 7.45–7.49(2H,m,ArH), 7.59–7.64(1H,m,ArH), 8.05–8.07 (2H,m,ArH).

Example 18

13-[0-3-(tert-Butoxycarbonylamino)-3-(2-furyl)-2-hydroxypropionyl]-10-0-(4-methylpiperazinocarbonyl)-10-deacetylbaccatin III (Compound 1-10)

In a similar manner to Example 4, the reaction and after-treatment were conducted using Compound (2-8) (130 mg, 0.117 mmol) obtained in Example 17, whereby the title compound (22 mg, 21%) was obtained as colorless crystals.

$^1$H—NMR(CDCl$_3$) δ: 1.14(3H,s,$C_{17}$ or $C_{16}$-Me), 1.26 (3H,s,$C_{17}$ or $C_{16}$-Me), 1.35(9H,s,t-Bu), 1.68(3H,s,$C_{19}$-Me), 1.89(1H,m), 1.92(3H,s,$C_{18}$-Me), 2.35(2H,m,$C_{14}$—H), 2.39 (3H,s), 2.40(3H,s), 2.50–2.60(6H,m), 3.15(1H,s), 3.40–3.85 (4H,m), 3.82(1H,d,J=7 Hz,$C_3$—H), 4.18(1H,d,J=9 Hz,$C_{20}$—H), 4.31(1H,d,J=9 Hz,$C_{20}$—H), 4.46(1H,dd,J=7 Hz,11 Hz,$C_7$—H), 4.72(1H,d,J=2 Hz,$C_2$,—H), 4.97(1H,d, J=8 Hz,$C_5$—H), 5.27(1H,d,J=10 Hz), 5.35(1H,d,J=10 Hz), 5.67(1H,d,J=7 Hz,$C_2$—H), 6.25(1H,t,J=8 Hz,$C_{13}$—H), 6.28 (1H,s,$C_{10}$—H), 6.32–6.33(1H,m,furyl H), 6.37–6.38(1H,m, furyl H), 7.43–7.44(1H,m,ArH), 7.48–7.53(2H,m,ArH), 7.59–7.64(1H,m,ArH), 8.11–8.13(2H,m,ArH).

SIMS m/z: 924(M+H)$^+$

Example 19

13-0-[3-Benzyloxycarbonyl-2,2-dimethyl-4-(2-furyl)-5-oxazolidinecarbonyl]-10-0-(4-morpholinopiperidinocarbonyl)-7-0-triethylsilyl-10-deacetylbaccatin III (Compound 2-9)

In a similar manner to Example 1, the reaction and after-treatment were conducted using 10-0-(4-morpholinopiperidinocarbonyl)-7-0-triethylsilyl-10-deacetylbaccatin III (100 mg, 0.117 mmol) and 3-benzyloxycarbonyl-2,2-dimethyl-4-(2-furyl)-5-oxazolidinecarboxylic acid (174 mg, 0.50 mmol), whereby the title compound (130 mg, 94%) was obtained.

$^1$H—NMR(CDCl$_3$) δ: 0.56–0.62(6H,m,Si—CH$_2$×3), 0.93 (9H,t,J=8 Hz,-Me×3), 1.18(6H,s,$C_{16}$-Me and $C_{17}$-Me), 1.59–1.73(9H,m,$C_{19}$-Me and oxazolidine Me×2), 1.82–1.92 (1H,m), 2.11(3H,s), 2.17(3H,s), 2.22(2H,m,$C_{14}$—H), 2.48–2.55(1H,m), 2.49–3.10(6H,m), 3.70–4.00(4H,m), 3.84 (1H,d,J=7 Hz,$C_3$—H), 4.13(1H,d,J=8 Hz,$C_{20}$—H), 4.28 (1H,d,J=8 Hz,$C_{20}$—H), 4.47(1H,dd,J=7 Hz,11 Hz,$C_7$—H), 4.78(1H,m), 4.93(1H,d,J=8 Hz,$C_5$—H), 4.95–5.20(2H,m), 5.43(1H,m), 5.67(1H,d,J=7 Hz,$C_2$—H), 6.20(1H,t,J=8 Hz,$C_{13}$—H), 6.34(2H,m), 6.39(3H,s,$C_{10}$—H), 7.10–7.40 (6H,m,ArH), 7.45–7.49(2H,m,ArH), 7.59–7.63(1H,m,ArH), 8.05–8.07(2H,m,ArH).

Example 20

13-0-[3-(tert-Butoxycarbonylamino)-3-(2-furyl)-2-hydroxypropionyl]-10-0-(4-morpholinopiperidinocarbonyl)-10-deacetylbaccatin III (Compound 1-11)

In a similar manner to Example 4, the reaction and after-treatment were conducted using Compound (2-9) (130 mg, 0.11 mmol) of Example 19, whereby the title compound (23 mg, 21%) was obtained as colorless crystals.

$^1$H—NMR(CDCl$_3$) δ: 1.14(3H,s,$C_{17}$ or $C_{16}$-Me), 1.26 (3H,s,$C_{17}$ or $C_{16}$-Me), 1.35(9H,s,t-Bu), 1.40–2.00(6H,m), 1.67(3H,s,$C_{19}$-Me), 1.91(3H,s,$C_{18}$-Me), 2.32–2.45(2H,m, $C_{14}$—H), 2.40(3H,s), 2.50–2.72(5H,m), 2.75–3.20(2H,m), 3.13(1H,s), 3.70–3.95(5H,m), 4.19–4.32(2H,m), 4.19(1H,d, J=9 Hz,$C_{20}$—H), 4.31(1H,d,J=9 Hz,$C_{20}$—H), 4.44(1H,dd, J=7 Hz,11 Hz,$C_7$—H), 4.72(1H,d,J=2 Hz,$C_2$,—H), 4.98(1H, d,J=8 Hz,$C_5$—H), 5.25(1H,d,J=10 Hz), 5.36(1H,d,J=10 Hz), 5.66(1H,d,J=7 Hz,$C_2$—H), 6.25(1H,t,J=8 Hz,$C_{13}$—H), 6.27 (1H,s,$C_{10}$—H), 6.31–6.33(1H,m,furyl H), 6.37–6.39(1H,m, furyl H), 7.41–7.42(1H,m,ArH), 7.50–7.53(2H,m,ArH), 7.59–7.64(1H,m,ArH), 8.11–8.12(2H,m,ArH).

SIMS m/z: 994[M+H]$^+$

Example 21

10-0-(4-Diethylaminopiperidinocarbonyl)-7-0-triethylsilyl-10-deacetylbaccatin III (Compound 2-10)

In tetrahydrofuran (5 mL) was dissolved 7-O-triethylsilyl-10-deacetylbaccatin III (100 mg, 0.15 mmol), followed by the addition of a 1.6 M n-butyl lithium hexane solution (0.13 mL, 0.206 mmol) at −40° C. in an argon gas atmosphere. The resulting mixture was stirred for 1 hour. To the reaction mixture was added a solution obtained by dissolving 4-diethylaminopiperidinocarbonyl chloride (37.1 mg, 0.17 mmol) in tetrahydrofuran (1 mL). The resulting mixture was stirred at −20° C. and then, after gradual heating, stirred overnight at a room temperature. An aqueous solution (50 mL) of ammonium chloride was added to the reaction mixture and the resulting mixture was extracted with ethyl acetate. The organic layer was washed with a saturated aqueous solution of sodium chloride, dried over anhydrous sodium sulfate and then concentrated to dryness under reduced pressure. The residue was purified by chromatography on a silica gel column [chloroform-methanol (95:5)]. The fractions providing a TLD single spot thus eluted were combined and concentrated to dryness under reduced pressure, whereby the title compound (67 mg, 54%) was obtained.

$^1$H—NMR(CDCl$_3$) δ: 0.55–0.65(6H,m,Si—CH$_2$×3), 0.93 (9H,t,J=8 Hz,-Me×3), 1.00–1.20(6H,m), 1.04(3H,s,$C_{17}$ or $C_{16}$-Me), 1.18(3H,s,$C_{17}$ or $C_{16}$-Me), 1.40–1.50(1H,m), 1.64 (1H,s), 1.68(3H,s,$C_{19}$-Me), 1.80–1.92(2H,m), 2.17–2.32 (3H,m), 2.25(3H,s), 2.28(3H,s), 2.49–2.58(1H,m), 2.60–3.00(7H,m), 3.90(1H,d,J=7 Hz,$C_3$—H), 4.15(1H,d, J=8 Hz,$C_{20}$—H), 4.20–4.50(2H,m), 4.30(1H,d,J=8 Hz,$C_{20}$—H), 4.48(1H,dd,J=7 Hz,11 Hz,$C_7$—H), 4.81(1H, m), 4.96(1H,d,J=8 Hz,$C_5$—H), 5.64(1H,d,J=7 Hz,$C_2$—H), 6.39(3H,s,$C_{10}$—H), 7.46–7.50(2H,m,ArH), 7.58–7.61(1H, m,ArH), 8.10–8.12(2H,m,ArH).

Example 22

13-0-[3-Benzyloxycarbonyl-2,2-dimethyl-4-(2-furyl)-5-oxazolidinecarbonyl]-10-0-(4-diethylaminopiperidinocarbonyl)-7-0-triethylsilyl-10-deacetylbaccatin III (Compound 2-11)

In a similar manner to Example 1, the reaction and after-treatment were conducted using Compound (2-10) (67 mg, 0.079 mmol) of Example 21 and 3-benzyloxycarbonyl-2,2-dimethyl-4-(2-furyl)-5-oxazolidinecarboxylicc acid (138 mg, 0.39 mmol), whereby the title compound (93 mg, 99%) was obtained.

$^1$H—NMR(CDCl$_3$) δ: 0.56–0.62(6H,m,Si—CH$_2$×3), 0.92 (9H,t,J=8 Hz,-Me×3), 1.17–1.23(12H,m), 1.40–2.00(5H,m), 1.67(3H,s,C$_{19}$-Me), 1.67–1.80(6H,m,oxazolidine Me×2), 1.81–1.91(1H,m), 2.11(3H,s), 2.17(3H,s), 2.22(2H,m,C$_{14}$—H), 2.48–2.56(1H,m), 2.70–3.15(6H,m), 3.84(1H,d,J=7 Hz,C$_3$—H), 4.13(1H,d,J=8 Hz,C$_{20}$—H), 4.20–4.50(2H,m), 4.28(1H,d,J=8 Hz,C$_{20}$—H), 4.47(1H,dd,J=7 Hz,11 Hz,C$_7$—H), 4.78(1H,m), 4.93(1H,d,J=8 Hz,C$_5$—H), 4.95–5.20(2H,m), 5.43(1H,m), 5.67(1H,d,J=7 Hz,C$_2$—H), 6.20(1H,t,J=8 Hz,C$_{13}$—H), 6.35(2H,m), 6.39(3H,s,C$_{10}$—H), 7.10–7.43 (6H,m,ArH), 7.45–7.49(2H,m,ArH), 7.59–7.63(1H,m,ArH), 8.05–8.07(2H,m,ArH).

Example 23

13-0-[3-(tert-Butoxycarbonylamino)-3-(2-furyl)-2-hydroxypropionyl]-10-0-(4-diethylaminopiperidinocarbonyl)-10-deacetylbaccatin III (Compound 1-12)

In a similar manner to Example 4, the reaction and after-treatment were conducted using Compound (2-11) (93 mg, 0.081 mmol) of Example 22, whereby the title compound (29 mg, 37%) was obtained as colorless crystals.

$^1$H—NMR(CDCl$_3$) 67 : 1.10–1.16(9H,m), 1.26(3H,s,C$_{17}$ or C$_{16}$-Me), 1.35(9H,s,t-Bu), 1.50–2.05(5H,m), 1.67(3H,s,C$_{19}$-Me), 1.89(1H,m), 1.91(3H,s,C$_{18}$-Me), 2.30–2.40(2H,m,C$_{14}$—H), 2.40(3H,s), 2.55(1H,m), 2.60–3.10(6H,m), 3.17 (1H,s), 3.82(1H,d,J=7 Hz,C$_3$—H), 4.18(1H,d,J=9 Hz,C$_{20}$—H), 4.18–4.34(2H,m), 4.31(1H,d,J=9 Hz,C$_{20}$—H), 4.46(1H,dd,J=7 Hz,11 Hz,C$_7$—H), 4.72(1H,d,J=2 Hz,C$_2$,—H), 4.97 (1H,d,J=8 Hz,C$_5$—H), 5.25(1H,d,J=10 Hz), 5.35(1H,d,J=10 Hz), 5.67(1H,d,J=7 Hz,C$_2$—H), 6.25(1H,t,J=8 Hz,C$_{13}$—H), 6.27(1H,s,C$_{10}$—H), 6.32–6.33(1H,m,furyl H), 6.37–6.38 (1H,m,furyl H), 7.41–7.42(1H,m,ArH), 7.48–7.53(2H,m,ArH), 7.59–7.64(1H,m,ArH), 8.11–8.12(2H,m,ArH).

SIMS m/z: 980[M+H]$^+$

Example 24

10-0-(4-di-n-Butylaminopiperidinocarbonyl)-7-0-triethylsilyl-10-deacetylbaccatin III (Compound 2-12)

In a similar manner to Example 21, the reaction and after-treatment were conducted using 7-0-triethylsilyl-10-deacetylbaccatin III (100 mg, 0.15 mmol) and 4-di-n-butylaminopiperidinocarbonyl chloride (46.5 mg, 0.17 mmol), whereby the title compound (79 mg, 59%) was obtained.

$^1$H—NMR(CDCl$_3$) 67 : 0.55–0.65(6H,m,Si—CH$_2$×3), 0.89–1.00(6H,m), 0.93(9H,t,J=8 Hz,-Me×3), 1.05(3H,s,C$_{17}$ or C$_{16}$-Me), 1.17(3H,s,C$_{17}$ or C$_{16}$-Me), 1.23–2.18(13H,m), 1.62(1H,s), 1.68(3H,s,C$_{19}$-Me), 1.80–1.92(1H,m), 2.23–2.30(2H,m), 2.23(3H,s), 2.29(3H,s), 2.40–3.10(6H,m), 2.49–2.58(1H,m), 3.90(1H,d,J=7 Hz,C$_3$—H), 4.15(1H,d,J=8 Hz,C$_{20}$—H), 4.20–4.52(2H,m), 4.31(1H,d,J=8 Hz,C$_{20}$—H), 4.48(1H,dd,J=7 Hz,11 Hz,C$_7$—H), 4.84(1H,m), 4.96(1H,d,J=8 Hz,C$_5$—H), 5.64(1H,d,J=7 Hz,C$_2$—H), 6.39(3H,s,C$_{10}$—H), 7.46–7.50(2H,m,ArH), 7.59–7.62(1H,m,ArH), 8.10–8.12(2H,m,ArH).

Example 25

13-0-[3-Benzyloxycarbonyl-2,2-dimethyl-4-(2-furyl)-5-oxazolidinecarbonyl]-10-0-(4-di-n-butylaminopiperidinocarbonyl)-7-0-triethylsilyl-10-deacetylbaccatin III (Compound 2-13)

In a similar manner to Example 1, the reaction and after-treatment were conducted using Compound (2-12) (79 mg, 0.088 mmol) of Example 24 and 3-benzyloxycarbonyl-2,2-dimethyl-4-(2-furyl)-5-oxazolidinecarboxylic acid (152 mg, 0.44 mmol), whereby the title compound (107 mg, 99%) was obtained.

$^1$H—NMR(CDCl$_3$) δ: 0.56–0.62(6H,m,Si—CH$_2$×3), 0.90–0.99(15H,m), 1.19(6H,s,C$_{16}$-Me and C$_{17}$-Me), 1.25–1.40(4H,m), 1.50–2.00(9H,m), 1.66(3H,s,C$_{19}$-Me), 1.66–1.80(6H,m,oxazolidine Me×2), 1.81–1.91(1H,m), 2.09 (3H,s), 2.17(3H,s), 2.18–2.25(2H,m,C$_{14}$—H), 2.46–2.56 (1H,m), 2.500–3.10(6H,m), 3.84(1H,d,J=7 Hz,C$_3$—H), 4.13 (1H,d,J=8 Hz,C$_{20}$—H), 4.25–4.50(2H,m), 4.28(1H,d,J=8 Hz,C$_{20}$—H), 4.47(1H,dd,J=7 Hz,11 Hz,C$_7$—H), 4.78(1H,m), 4.93(1H,d,J=8 Hz,C$_5$—H), 4.95–5.20(2H,m), 5.43(1H,m), 5.66(1H,d,J=7 Hz,C$_2$—H), 6.20(1H,t,J=8 Hz,C$_{13}$—H), 6.34(2H,m), 6.39(3H,s,C$_{10}$—H), 7.10–7.41(6H,m,ArH), 7.45–7.49(2H,m,ArH), 7.59–7.63(1H,m,ArH), 8.05–8.07 (2H,m,ArH).

Example 26

13-0-[3-(tert-Butoxycarbonylamino)-3-(2-furyl)-2-hydroxypropionyl]-10-0-(4-di-n-butylaminopiperidinocarbonyl)-10-deacetylbaccatin III (Compound 1-13)

In a similar manner to Example 4, the reaction and after-treatment were conducted using Compound (2-13) (107 mg, 0.087 mmol) of Example 25, whereby the title compound (20 mg, 23%) was obtained as colorless crystals.

$^1$—NMR(CDCl$_3$) δ: 0.88–0.98(6H,m), 1.15(3H,s,C$_{17}$ or Cl$_{16}$-Me), 1.20–2.00(13H,m), 1.26(3H,s,C$_{17}$ or C$_{16}$-Me), 1.35(9H,s,t-Bu), 1.67(3H,s,C$_{19}$-Me), 1.89(1H,m), 1.91(3H,s,C$_{18}$-Me), 2.30–2.40(2H,m,C$_{14}$—H), 2.40(3H,s), 2.45–3.05(7H,m), 3.20(1H,s), 3.82(1H,d,J=7 Hz,C$_3$—H), 4.18(1H,d,J=9 Hz,C$_{20}$,—H), 4.18–4.32(2H,m), 4.30(1H,d,J=9 Hz,C$_{20}$—H), 4.46(1H,dd,J=7 Hz,11 Hz,C$_7$—H), 4.72 (1H,d,J=2 Hz,C$_2$,—H), 4.97(1H,d,J=8 Hz,C$_5$—H), 5.27(1H,d,J=10 Hz), 5.35(1H,d,J=10 Hz), 5.67(1H,d,J=7 Hz,C$_2$—H), 6.25(1H,t,J=8 Hz,C$_{13}$—H), 6.26(1H,s,C$_{10}$—H), 6.32–6.33 (1H,m,furyl H), 6.37–6.38(1H,m,furyl H), 7.43–7.44(1H,m,ArH), 7.48–7.53(2H,m,ArH), 7.59–7.64(1H,m,ArH), 8.11–8.13(2H,m,ArH)

SIMS m/z: 1036[M+H]$^+$

Example 27

10-0-(4-Propylpiperazinocarbonyl)-7-0-triethylsilyl-10-deacetylbaccatin III (Compound 2-14)

In a similar manner to Example 21, the reaction and after-treatment were conducted using 7-0-triethylsilyl-10-deacetylbaccatin III (400 mg, 0.61 mmol) and 4-propylpiperazinocarbonyl chloride (232 mg, 1.22 mmol), whereby the title compound (344 mg, 70%) was obtained.

$^1$H—NMR(CDCl$_3$) δ: 0.56–0.63(6H,m,Si—CH$_2$×3), 0.89–0.99(3H,m), 0.93(9H,t,J=8 Hz,-Me×3), 1.05(3H,s,C$_{17}$ or C$_{16}$-Me), 1.15(3H,s,C$_{17}$ or C$_{/6}$-Me), 1.65–2.00(2H,m), 1.68(3H,s,C$_{19}$-Me), 1.84–1.90(1H,m), 2.23–2.80(6H,m), 2.23(3H,s), 2.29(3H,s), 2.49–2.57(1H,m), 3.89(1H,d,J=7 Hz,C$_3$—H), 4.15(1H,d,J=8 Hz,C$_{20}$—H), 3.50–4.10(4H,m), 4.31(1H,d,J=8 Hz,C$_{20}$—H), 4.49(1H,dd,J=7 Hz,11 Hz,C$_7$—H), 4.83–4.87(1H,m), 4.95–4.97(1H,m,C$_5$—H), 5.63(1H,d,J=7 Hz,C$_2$—H), 6.40(3H,s,C$_{10}$—H), 7.46–7.50(2H,m,ArH), 7.59–7.63(1H,m,ArH), 8.10–8.12(2H,m,ArH).

Example 28

13-0-[3-Benzyloxycarbonyl-2,2-dimethyl-4-(2-furyl)-5-oxazolidinecarbonyl]-10-0-(4-propylpiperazinocarbonyl)-7-0-triethylsilyl-10-deacetylbaccatin III (Compound 2-15)

In a similar manner to Example 1, the reaction and after-treatment were conducted using Compound (2-14)

(100 mg, 0.123 mmol) of Example 27 and 3-benzyloxycarbonyl-2,2-dimethyl-4-(2-furyl)-5-oxazolidinecarboxylic acid (170 mg, 0.54 mmol), whereby the title compound (140 mg, 99%) was obtained.

$^1$H—NMR(CDCl$_3$) 67 : 0.51–0.66(6H,m), 0.92(3H,t,J=7 Hz), 0.92(9H,t,J=8 Hz), 1.18(3H,s), 1.20(3H,s), 1.51–1.56 (2H,m), 1.67(3H,s), 1.74(6H,s), 1.84–1.93(2H,m), 2.13(3H, s), 2.17(s,3H), 2.20–2.23(1H,m), 2.32–2.36(2H,m), 2.41–2.55(5H,m), 3.39–3.92(4H,m), 3.84(1H,d,J=7 Hz), 4.13(1H,d,J=8 Hz), 4.28(1H,d,J=8 Hz), 4.47(1H,dd,J=7,11 Hz), 4.78(1H,brs), 4.91–4.93(1H,m), 5.02–5.20(2H,m), 5.43 (1H,brs), 5.67(1H,d,J=7 Hz), 6.18–6.22(1H,m), 6.33–6.39 (2H,m), 6.39(1H,s), 7.16–7.40(6H,m), 7.47(2H,t,J=8 Hz), 7.59–7.63(1H,m), 8.04–8.07(2H,m).

Example 29

13-0-[3-(tert-Butoxycarbonylamino)-3-(2-furyl)-2-hydroxypropionyl]-10-0-(4-propylpiperazinocarbonyl)-10-deacetylbaccatin III (Compound 1-14)

In a similar manner to Example 16, the reaction and after-treatment were conducted using Compound (2-15) (130 mg, 0.114 mmol) of Example 28, whereby the title compound (65 mg, 60%) was obtained as colorless crystals.

$^1$H—NMR(CDCl$_3$) δ: 0.95(3H,t,J=7 Hz), 1.14(3H,s), 1.26(3H,s), 1.35(9H,s,t-Bu), 1.68(3H,s), 1.82–1.88(3H,m), 1.92(3H,s), 2.32–2.38(2H,m), 2.40(3H,s), 2.29–2.70(6H,m), 3.12(1H,s), 3.32–3.85(4H,m), 3.73–3.76(2H,m), 3.82(1H,d, J=7 Hz), 4.18(1H,d,J=8 Hz), 4.31(1H,d,J=8 Hz), 4.42–4.48 (1H,m), 4.72(1H,d,J=2 Hz,C$_2$,—H), 4.96–4.98(1H,m), 5.23–55(1H,m), 5.33–5.36(1H,m), 5.67(1H,d,J=7 Hz), 6.23–6.27(1H,m), 6.28(1H,s), 6.32–6.33(1H,m), 6.38–6.39 (1H,m), 7.42–7.43(1H,m), 7.48–7.52(2H,m), 7.59–7.63(1H, m), 8.11–8.13(2H,m).

SI-MS m/z: 952[M+H]$^+$

Example 30

13-0-[3-Benzyloxycarbonyl-2,2-dimethyl-4-{2-(5-methylfuryl)}-5-oxazolidinecarbonyl]-10-0(4-methylpiperazinocarbonyl)-7-0-triethylsilyl-10-deacetylbaccatin III (Compound 2-16)

In a similar manner to Example 1, the reaction and after-treatment were conducted using 10-0-(4-methylpiperazinocarbonyl)-7-0-triethylsilyl-10-deacetylbaccatin III (100 mg, 0.127 mmol) and 3-benzyloxycarbonyl-2,2-dimethyl-4-(2-furyl)-5-oxazolidinecarboxylic acid (198 mg, 0.55 mmol), whereby the title compound (100 mg, 70%) was obtained.

$^1$H—NMR(CDCl$_3$) δ: 0.56–0.62(6H,m,Si—CH$_2$×3), 0.93 (9H,t,J=8 Hz,-Me×3), 1.19(6H,s,C$_{16}$-Me and C$_{17}$-Me), 1.67 (3H,m,C$_{19}$-Me), 1.67–1.75(6H,m,oxazolidine Me×2), 1.83–1.92(1H,m), 2.12(3H,s), 2.16(3H,s), 2.22(2H,m,C$_{14}$—H), 2.27(3H,s), 2.39–2.55(5H,m), 2.39(3H,s), 2.39–2.70 (4H,m), 3.40–4.00(4H,m), 3.84(1H,d,J=7 Hz,C$_3$—H), 4.14 (1H,d,J=8 Hz,C$_{20}$—H), 4.28(1H,d,J=8 Hz,C$_{20}$—H), 4.47 (1H,dd,J=7 Hz,11 Hz,C$_7$—H), 4.78(1H,s), 4.93(1H,d,J=8 Hz,C$_5$—H), 4.95–5.20(2H,m), 5.45(1H,s), 5.66(1H,d,J=7 Hz,C$_2$—H), 5.88–6.12(2H,m), 6.20(1H,t,J=8 Hz,C$_{13}$—H), 6.39(3H,s,C$_{10}$—H), 7.10–7.40(5H,m,ArH), 7.45–7.49(2H, m,ArH), 7.59–7.64(1H,m,ArH), 8.05–8.07(2H,m,ArH)

Example 31

13-0-[3-(tert-Butoxycarbonylamino)-3-{2-(5-methylfuryl)}-2-hydroxypropionyl]-10-0-(4-methylpiperazinocarbonyl)-10-deacetylbaccatin III (Compound 1-15)

In a similar manner to Example 4, the reaction and after-treatment were conducted using Compound (2-16) (100 mg, 0.088 mmol) of Example 30, whereby the title compound (20 mg, 25%) was obtained as colorless crystals.

$^1$H—NMR(CDCl$_3$) δ: 1.15(3H,s,C$_{17}$ or C$_{16}$-Me), 1.26 (3H,s,C$_{17}$ or C$_{16}$-Me), 1.35(9H,s,t-Bu), 1.68(3H,s,C$_{19}$-Me), 1.89(1H,m), 1.92(3H,s,C$_{18}$-Me), 2.29(3H,s), 2.32–2.40(2H, m,C$_{14}$—H), 2.36(3H,s), 2.42(3H,s), 2.46–2.59(5H,m), 3.17 (1H,s), 3.40–3.78(4H,m), 3.82(1H,d,J=7 Hz,C$_3$—H), 4.18 (1H,d,J=9 Hz,C$_{20}$—H), 4.31(1H,d,J=9 Hz,C$_{20}$—H), 4.46 (1H,dd,J=7 Hz,11 Hz,C$_7$—H), 4.69(1H,d,J=2 Hz,C$_2$,—H), 4.98(1H,d,J=8 Hz,C5—H), 5.22(1H,d,J=10 Hz), 5.30(1H,d, J=10 Hz), 5.67(1H,d,J=7 Hz,C$_2$—H), 5.94–5.95(1H,m,furyl H), 6.17–6.18(1H,m,furyl H), 6.23(1H,t,J=8 Hz,C$_{13}$—H), 6.28(1H,s,C$_{10}$—H), 7.48–7.53(2H,m,ArH), 7.59–7.64(1H, m,ArH), 8.11–8.12 (2H,m,ArH).

SIMS m/z: 938[M+H]$^+$

Example 32

13-0-[3-Benzyloxycarbonyl-2,2-dimethyl-4-(4-fluorophenyl)-5-oxazolidinecarbonyl]-10-0-[4-(isopropylaminocarbonylmethyl) piperazinocarbonyl]-7-0-triethylsilyl-10-deacetylbaccatin III (Compound 2-17)

In a similar manner to Example 1, the reaction and after-treatment were conducted using 10-0-[4-(isopropylaminocarbonylmethyl)piperazinocarbonyl]-7-0-triethylsilyl-10-deacetylbaccatin III (100 mg, 0.115 mmol) and 3-benzyloxycarbonyl-2,2-dimethyl-4-(4-fluorophenyl)-5-oxazolidinecarboxylic acid (172 mg, 0.460 mmol), whereby the title compound (140 mg, 99%) was obtained.

$^1$H—NMR(CDCl$_3$) δ: 0.53–0.63(6H,m), 0.92(9H,t,J=8 Hz), 1.18(6H,s), 1.19(6H,d,J=7 Hz), 1.66(3H,s), 1.75(3H,s), 1.80–1.92(1H,m), 1.81(3H,s), 1.96(3H,s), 2.09(3H,s), 2.17 (2H,d,J=8 Hz), 2.46–2.54(1H,m), 2.40–3.10(4H,m), 3.47–4.15(5H,m), 3.79(1H,d,J=7 Hz), 4.10(1H,d,J=8 Hz), 4.26(1H,d,J=8 Hz), 4.43–4.48(2H,m), 4.80–5.03(2H,m), 4.88–4.90(1H,m), 5.20(brs,1H), 5.65(1H,d,J=7 Hz), 6.21–6.25(1H,m), 6.38(1H,s), 6.85–7.36(m,9H), 7.47–7.52 (2H,m), 7.60–7.64(1H,m), 8.02–8.05(2H,m).

SI-MS m/z:

Example 33

13-0-[3-(tert-Butoxycarbonylamino)-3-(4-fluorophenyl)-2-hydroxypropionyl]-10-0-[4-(isopropylaminocarbonylmethyl) piperazinocarbonyl]-10-deacetylbaccatin III (Compound 1-16)

In a similar manner to Example 16, the reaction and after-treatment were conducted using Compound (2-17) (140 mg, 0.114 mmol) of Example 32, whereby the title compound (27 mg, 23%) was obtained as colorless crystals.

$^1$H—NMR(CDCl$_3$) δ: 1.10(3H,s), 1.19(6H,d,J=7 Hz), 1.26(3H,s), 1.33(9H,s), 1.67(3H,s), 1.88(3H,s), 1.85–1.91 (1H,m), 2.29–2.32(2H,m), 2.37(3H,s), 2.50–2.73(5H,m), 3.08(3H,brs), 3.55–3.75(m,4H), 3.79(1H,d,J=7 Hz), 4.06–4.15(1H,m), 4.17(1H,d,J=9 Hz), 4.30(1H,d,J=9 Hz), 4.41–4.46(1H,m), 4.60–4.61(1H,m), 4.95–4.97(1H,m), 5.24–5.27(1H,m), 5.46–5.48(1H,m), 5.66(1H,d,J=7 Hz), 6.24–6.28(1H,m), 6.28(1H,s), 7.06–7.11(2H,m), 7.36–7.39 (2H,m), 7.50(2H,t,J=8 Hz), 7.59–7.63(1H,m), 8.10(2H,d, J=8 Hz).

SI-MS m/z: 1037[M+H]$^+$

Example 34

13-0-[3-Benzyloxycarbonyl-2,2-dimethyl-4-(4-fluorophenyl)-5-oxazolidinecarbonyl]-10-0-(4-piperidinopiperidinocarbonyl)-7-0-triethylsilyl-10-deacetylbaccatin III (Compound 2-18)

In a similar manner to Example 1, the reaction and after-treatment were conducted using 10-0-(4- piperidinopiperidinocarbonyl)-7-O-triethylsilyl-10-deacetylbaccatin III (100 mg, 0.117 mmol) and 3-benzyloxycarbonyl-2,2-dimethyl-4-(4-fluorophenyl)-5-oxazolidinecarboxylic acid (175 mg, 0.469 mmol), whereby the title compound (140 mg, 99%) was obtained.

$^1$H—NMR(CDCl$_3$) δ: 0.55–0.62(6H,m), 0.92(9H,t,J=8 Hz), 1.19(6H,s), 1.55–1.61(10H,m), 1.65(3H,s), 1.75(3H,s), 1.88–1.91(1H,m), 1.81(3H,s), 1.95(3H,s), 2.08(3H,s), 2.17 (2H,d,J=10 Hz), 2.46–2.54(1H,m), 2.60–3.00(7H,m), 3.79 (1H,d,J=7 Hz), 4.10(1H,d,J=9 Hz), 4.20–4.46(4H,m), 4.27 (1H,d,J=9 Hz), 4.80–5.10(2H,m), 4.88–4.90(1H,m), 5.20 (1H,brs), 5.66(1H,d,J=7 Hz), 6.21–6.25(1H,m), 6.38(1H,s), 6.83(1H,brs), 7.00–7.37(9H,m), 7.47–7.51(2H,m), 7.61–7.65(1H,m), 8.03–8.05(2H,m).

SI-MS m/z: 1208[M+H]$^+$

Example 35

13-O-[3-(tert-Butoxycarbonylamino)-3-(4-fluorophenyl)-2-hydroxypropionyl]-10-O-(4-piperidinopiperidinocarbonyl)-10-deacetylbaccatin III (Compound 1-17)

In a similar manner to Example 16, the reaction and after-treatment were conducted using Compound (2-18) (140 mg, 0.116 mmol) of Example 34, whereby the title compound (43 mg, 26%) was obtained as colorless crystals.

$^1$H—NMR(CDCl$_3$) δ: 1.15(3H,s), 1.26(3H,s), 1.33(9H,s), 1.48–1.94(11H,m), 1.67(3H,s), 1.86(3H,s), 2.30–2.32(2H, m), 2.37(3H,s), 2.52–3.10(8H,m), 3.80(1H,d,J=7 Hz), 4.16 (1H,d,J=8 Hz), 4.20–4.30(2H,m), 4.31(1H,d,J=8 Hz), 4.41–4.47(1H,m), 4.60(1H,s), 4.95–4.97(1H,m), 5.21–5.26 (2H,m), 5.66(1H,d,J=7 Hz), 6.26–6.31(1H,m), 6.25(1H,s), 7.06–7.11(2H,m), 7.36–7.39(2H,m), 7.50(2H,t,J=7 Hz), 7.59–7.63(1H,m), 8.11(2H,d,J=7 Hz).

SI-MS m/z: 1020[M+H]$^+$

Example 36

13-O-[3-Benzyloxycarbonyl-2,2-dimethyl-4-(2-fluorophenyl)-5-oxazolidinecarbonyl]-10-O-(4-methylpiperazinocarbonyl)-7-O-triethylsilyl-10-deacetylbaccatin III (Compound 2-19)

In a similar manner to Example 1, the reaction and after-treatment were conducted using 10-O-(4-methylpiperazinocarbonyl)-7-O-triethylsilyl-10-deacetylbaccatin III (100 mg, 0.128 mmol) and 3-benzyloxycarbonyl-2,2-dimethyl-4-(2-fluorophenyl)-5-oxazolidinecarboxylic acid (191 mg, 0.512 mmol), whereby the title compound (127 mg, 87%) was obtained.

$^1$H—NMR(CDCl$_3$) 67 : 0.51–0.65(6H,m), 0.92(9H,t,J=8 Hz), 1.19(3H,s), 1.20(3H,s), 1.66(3H,s), 1.75(3H,s), 1.80–1.89(1H,m), 1.81(3H,s), 1.96(3H,s), 2.10(3H,s), 2.17 (2H,d,J=9 Hz), 2.45(3H,s), 2.48–2.80(5H,m), 3.50–3.97 (4H,m), 3.80(1H,d,J=7 Hz), 4.11(1H,d,J=8 Hz), 4.27(1H,d, J=8 Hz), 4.43–4.48(m,2H), 4.80–5.15(3H,m), 5.21(brs,$_1$1H), 5.65(1H,d,J=7 Hz), 6.21–6.25(1H,m), 6.38(1H,s), 6.84(1H,brs), 7.00–7.38(m,9H), 7.47–7.51(2H,m), 7.61–7.64(1H,m), 8.03–8.05(2H,m).

SI-MS m/z: 1140[M+H]$^+$

Example 37

13-O-[3-(tert-Butoxycarbonylamino)-3-(2-fluorophenyl)-2-hydroxypropionyl]-10-O-(4-methylpiperazinocarbonyl)-10-deacetylbaccatin III (Compound 1-18)

In a similar manner to Example 16, the reaction and after-treatment were conducted using Compound (2-19) (120 mg, 0.105 mmol) of Example 36, whereby the title compound (17 mg, 17%) was obtained as colorless crystals.

$^1$H—NMR(CDCl$_3$) δ:1.14(3H,s), 1.26(3H,s), 1.33(9H,s), 1.67(3H,s), 1.84–1.94(m,4H), 2 .22–2.33(2H,m), 2.36(3H, s), 2.41(3H,s), 2.47–2.63(5H,m), 3.40–3.80(4H,m), 3.80 (1H,d,J=7 Hz), 4.18(1H,d,J=8 Hz), 4.30(1H,d,J=8 Hz), 4.44 (1H,dd,J=7,11 Hz), 4.60–4.61(1H,m), 4.95–4.97(1H,m), 5.24–5.26(1H,m), 5.39–5.41(1H,m), 5.66(1H,d,J=7 Hz), 6.24–6.27(1H,m), 6.27(1H,s), 7.06–7.11(2H,m), 7.36–7.39 (2H,m), 7.50(2H,t,J=8 Hz), 7.59–7.63(1H,m), 8.10(2H,d, J=7 Hz).

SI-MS m/z: 952[M+H]$^+$

Example 38

13-O-[3-Benzyloxycarbonyl-2,2-dimethyl-4-(2-fluorophenyl)-5-oxazolidinecarbonyl]-10-O-(4-ethylpiperazinocarbonyl)-7-O-triethylsilyl-10-deacetylbaccatin III (Compound 2-20)

In a similar manner to Example 1, the reaction and after-treatment were conducted using 10-O-(4-ethylpiperazinocarbonyl)-7-O-triethylsilyl-10-deacetylbaccatin III (100 mg, 0.125 mmol) and 3-benzyloxycarbonyl-2,2-dimethyl-4-(2-fluorophenyl)-5-oxazolidinecarboxylic acid (187 mg, 0.500 mmol), whereby the title compound (143 mg, 99%) was obtained.

$^1$H—NMR(CDCl$_3$) 67 : 0.53–0.63(6H,m), 0.92(9H,t,J=8 Hz), 1.14–1.18(3H,m), 1.20(6H,s), 1.58–1.63(1H,m), 1.66 (3H,s), 1.95(3H,s), 2.11(s,3H), 2.18(1H,d,J=9 Hz), 2.35–2.65(7H,m), 3.50–4.07(4H,m), 3.81(1H,d,J=7 Hz), 4.12(1H,d,J=8 Hz), 4.25(1H,d,J=8 Hz), 4.45(1H,dd,J=7,11 Hz), 4.55(1H,d,J=5 Hz), 4.88–5.08(3H,m), 5.58(1H,d,J=6 Hz), 5.65(1H,d,J=7 Hz), 6.20–6.25(1H,m), 6.39(l1H,s), 6.85 (1H,brs), 7.00–7.40(9H,m), 7.49(2H,t,J=8 Hz), 7.63(1H,t, J=7 Hz), 8.04–8.06(2H,m).

SI-MS m/z: 1154[M+H]$^+$

Example 39

13-O-[3-(tert-Butoxycarbonylamino)-3-(2-fluorophenyl)-2-hydroxypropionyl]-10-O-(4-ethylpiperazinocarbonyl)-10-deacetylbaccatin III (Compound 1-19)

In a similar manner to Example 16, the reaction and after-treatment were conducted using Compound (2-20) (143 mg, 0.124 mmol) of Example 38, whereby the title compound (32 mg, 27%) was obtained as colorless crystals.

$^1$H—NMR(CDCl$_3$) δ: 1.13, (3H,t,J=7 Hz), 1.14(3H,s), 1.28(3H,s), 1.30(9H,s), 1.67(3H,s), 1.84–1.94(m,4H), 2.20–2.31(2H,m), 2.43(3H,s), 2.50(2H,q,J=7 Hz), 2.51–2.56 (5H,m), 3.40–3.80(m,4H), 3.80(1H,d,J=7 Hz), 4.18(1H,d, J=8 Hz), 4.31(1H,d,J=8 Hz), 4.46(1H,dd,J=7,11 Hz), 4.60–4.61(1H,m), 4.97–4.99(1H,m), 5.49–5.51(1H,m), 5.56–5.59(1H,m), 5.66(1H,d,J=7 Hz), 6.25–6.29(1H,m), 6.27(1H,s), 7.08–7.21(2H,m), 7.29–7.38(2H,m), 7.50(2H,t, J=8 Hz), 7.58–7.62(1H,m), 8.12(2H,d,J=7 Hz).

SI-MS m/z: 966[M+H]$^+$

Example 40

13-O-[3-Benzyloxycarbonyl-2,2-dimethyl-4-(2-fluorophenyl)-5-oxazolidinecarbonyl]-10-O-(4-morpholinopiperidinocarbonyl)-7-O-triethylsilyl-10-deacetylbaccatin III (Compound 2-21)

In a similar manner to Example 1, the reaction and after-treatment were conducted using 10-O-(4)

morpholinopiperidinocarbonyl)-7-0-triethylsilyl-10-deacetylbaccatin III (100 mg, 0.117 mmol) and 3-benzyloxycarbonyl-2,2-dimethyl-4-(2-fluorophenyl)-5-oxazolidinecarboxylic acid (175 mg, 0.468 mmol), whereby the title compound (140 mg, 99%) was obtained.

$^1$H—NMR(CDCl$_3$) δ: 0.54–0.60(6H,m), 0.91(9H,t,J=8 Hz), 1.19(6H,s), 1.55–1.92(5H,m), 1.66(3H,s), 1.77(3H,s), 1.82(3H,s), 1.94(3H,s), 2.10(3H,s), 2.20(2H,d,J=9 Hz), 2.45–2.52(1H,m), 2.53–3.10(4H,m), 3.76–3.81(5H,m), 4.05–4.44(4H,m), 4.12(1H,d,J=8 Hz), 4.25(1H,d,J=8 Hz), 4.45(1H,dd,J=7,11 Hz), 4.55(1H,d,J=6 Hz), 4.87–5.08(3H, m), 5.58(1H,d,J=5 Hz), 5.66(1H,d,J=7 Hz), 6.22(1H,t,J=9 Hz), 6.38(1H,s), 6.85(1H,brs), 7.00–7.31(m,9H), 7.49(2H,t, J=8 Hz), 7.63(1H,t,J=7 Hz), 8.03–8.06(2H,m).

Example 41

13-0-[3-(tert-Butoxycarbonylamino)-3-(2-fluorophenyl)-2-hydroxypropionyl]-10-0-(4-morpholinopiperidinocarbonyl)-10-deacetylbaccatin III (Compound 1-20)

In a similar manner to Example 16, the reaction and after-treatment were conducted using Compound (2-21) (140 mg, 0.116 mmol) of Example 40, whereby the title compound (29 mg, 25%) was obtained as colorless crystals.

$^1$H—NMR(CDCl$_3$) 67 : 1.15(3H,s), 1.28(3H,s), 1.33(9H, s), 1.40–1.90(4H,m), 1.67(3H,s), 1.85–1.88(1H,m), 1.92 (3H,s), 2.20–2.38(2H,m), 2.43(3H,s), 2.49–3.12(7H,m), 3.74–3.78(4H,m), 3.80(1H,d,J=7 Hz), 4.06–4.24(2H,m), 4.18(1H,d,J=8 Hz), 4.31(1H,d,J=8 Hz), 4.43–4.48(1H,m), 4.61–4.62(1H,m), 4.96–4.99(1H,m), 5.47(1H,d,J=10 Hz), 5.56–5.59(1H,m), 5.66(1H,d,J=7 Hz), 6.26–6.30(1H,m), 6.26(1H,s), 7.08–7.21(2H,m), 7.29–7.39(2H,m), 7.50(2H,t, J=8 Hz), 7.58–7.62(1H,m), 8.12(2H,d,J=8 Hz).

SI-MS m/z: 1022[M+H]$^+$

Example 42

$^1$13-0-[3-(2-Furyl)-3-n-hexanoylamino-2-hydroxypropionyl]-10-0-(4-propylpiperazinocarbonyl)-10-deacetylbaccatin III (Compound 1-21)

Compound (2-15) (215 mg, 0.188 mmol) obtained in Example 28 was dissolved in ethanol (33 mL), followed by the addition of 0.1N-hydrochloric acid (19 mL). The resulting mixture was stirred at room temperature for 17 hours. The solvent was distilled off under reduced pressure. A saturated aqueous solution of sodium bicarbonate was added to the residue and the resulting mixture was extracted with chloroform. The organic layer was dried over sodium sulfate and concentrated to dryness under reduced pressure. To the residue were added methanol (25 mL), water (2.5 mL) and 10% palladium-activated carbon (49 mg), followed by stirring at normal temperature and normal pressure for 3 hours in an H$_2$ gas atmosphere. The reaction mixture was filtered and the filtrate was concentrated to dryness under reduced pressure. A saturated aqueous solution of sodium bicarbonate was added to the residue and the resulting mixture was extracted with chloroform. The organic layer was dried over sodium sulfate and concentrated to dryness under reduced pressure, whereby colorless crystals were obtained. The resulting crystals (110 mg, 0.129 mmol) were dissolved in ethyl acetate (7 mL), followed by the addition of a saturated aqueous solution (7.1 mL) of sodium bicarbonate and purified water (7 mL). While stirring, n-hexanoyl chloride (19 mg, 0.14 mmol) was added dropwise. The resulting mixture was stirred at room temperature for 15 minutes. The reaction mixture was extracted with ethyl acetate. The organic layer was washed with a saturated solution of sodium chloride, dried over sodium sulfate and concentrated to dryness under reduced pressure. The residue was purified by chromatography on a silica gel column [CHCl$_3$-MeOH (96:4)], whereby the title compound (100 mg, 55%) was obtained as colorless crystals.

$^1$H—NMR(CDCl$_3$) δ: 0.78–0.82(3H,m,), 0.89(3H,t,7 Hz), 1.12(3H,s), 1.18(7H,m), 1.47–1.59(4H,m), 1.65(3H,s, C$_{19}$-Me), 1.80–1.89(1H,m), 1.86(3H,s,C$_{18}$-Me), 2.14–2.20 (2H,m), 2.25–2.40(5H,m), 2.36(3H,s), 2.40–2.55(4H,m), 3.15(1H,br-s), 3.35–3.73(4H,m), 3.76(1H,d,J=7 Hz,C$_3$—H), 4.17(1H,d,J=9 Hz,C$_{20}$—H), 4.26(1H,d,J=9 Hz,C$_{20}$—H), 4.42(1H,dd,J=7 Hz,11 Hz,C$_7$—H), 4.70(1H,d,J=2 Hz,C$_2$,—H), 4.94(1H,d,J=8 Hz,C$_5$—H), 5.67(2H,d,J=7 Hz), 6.15(1H, d,J=9 Hz), 6.20(1H,t,J=8 Hz,C$_{13}$—H), 6.24(1H,s,C$_{10}$—H), 6.27–6.30(1H,m), 6.34–6.37(1H,m), 7.37–7.40(1H), 7.44–7.51(2H,m), 7.55–7.61(1H,m), 8.06–8.11(2H,m).

SIMS m/z: 950(M+H)$^+$

Example 43

13-0-[3-(3,3-Dimethylacryloylamino)-3-(2-furyl)-2-hydroxypropionyl]-10-0-(4-propylpiperazinocarbonyl)-10-deacetylbaccatin III (Compound 1-22)

In a similar manner to Example 42, the reaction and after-treatment were conducted using Compound (2-15) (215 mg, 0.188 mmol) of Example 28 and 3,3-dimethylacryloyl chloride (17 mg, 0.14 mmol), whereby the title compound (90 mg, 51%) was obtained as colorless crystals.

$^1$H—NMR(CDCl$_3$) 67 : 0.92(3H,t,7 Hz), 1.14(3H,s), 1.24 (3H,s), 1.49–1.59(2H,m), 1.67(3H,s,C$_{19}$-Me), 1.79(3H,s), 1.89(3H,s,C$_{18}$-Me), 2.02(3H,s), 2.28–2.43(5H,m), 2.41(3H, s), 2.44–2.58(4H,m), 3.17(1H,br-s), 3.37–3.75(4H,m), 3.81 (1H,d,J=7 Hz,C$_3$—H), 4.18(1H,d,J=9 Hz,C$_{20}$—H), 4.30 (1H,d,J=9 Hz,C$_{20}$—H), 4.44(1H,dd,J=7 Hz,11 Hz,C$_7$—H), 4.74(1H,d,J=2 Hz,C$_2$,—H), 4.98(1H,d,J=8 Hz,C$_5$—H), 5.58 (1H,s), 5.65–5.73(2H,m), 6.05(1H,d,J=9 Hz), 6.23(1H,t,J=8 Hz,C$_{13}$—H), 6.26(1H,s,C$_{10}$—H), 6.30–6.34(1H,m), 6.35–6.39(1H,m), 7.40–7.43(1H,m), 7.49–7.52(2H,m), 7.57–7.63(1H,m), 8.10–8.13(2H,m).

SIMS m/z: 934(M+H)$^+$

Example 44

13-0-[3-(2-furyl)-2-hydroxy-3-(2-thenoylamino) propionyl]-10-O-(4-propylpiperazinocarbonyl)-10-deacetylbaccatin III (Compound 1-23)

In a similar manner to Example 42, the reaction and after-treatment were conducted using Compound (2-15) (215 mg, 0.188 mmol) of Example 28 and 2-thenoyl chloride (21 mg, 0.14 mmol), whereby the title compound (80 mg, 44%) was obtained as colorless crystals.

$^1$H—NMR(CDCl$_3$) δ: 0.92(3H,t,7 Hz), 1.14(3H,s), 1.24 (3H,s), 1.49–1.58(2H,m), 1.69(3H,s,C$_{19}$-Me), 1.83–1.93(H, m), 1.89(3H,s,C$_{18}$-Me), 2.27–2.43(5H,m), 2.41(3H,s), 2.44–2.58(4H,m), 3.15(1H,br-s), 3.37–3.76(4H,m), 3.80 (1H,d,J=7 Hz,C$_3$—H), 4.21(1H,d,J=9 Hz,C$_{20}$—H), 4.30 (1H,d,J=9 Hz,C$_{20}$—H), 4.44(1H,dd,J=7 Hz,11 Hz,C$_7$—H), 4.82(1H,d,J=2 Hz,C$_2$,—H), 4.98(1H,d,J=8 Hz,C$_5$—H), 5.67 (1H,d,J=7 Hz,C$_2$—H), 5.85(1H,m), 6.26(1H,t,J=8 Hz,C$_{13}$—H), 6.26(1H,s,C$_{10}$—H), 6.38–6.42(2H,m), 6.71(1H,d,J=9 Hz), 7.05–7.08(1H,m), 7.43–7.55(5H,m), 7.61–7.65(1H,m), 8.10–8.15(2H,m).

SIMS m/z: 962(M+H)$^+$

Example 45

13-0-[3-(2-Furoylamino)-3-(2-furyl)-2-hydroxypropionyl]-10-0-(4-propylpiperazinocarbonyl)-10-deacetylbaccatin III (Compound 1-24)

In a similar manner to Example 42, the reaction and after-treatment were conducted using Compound (2-15) (215 mg, 0.188 mmol) of Example 28 and 2-furoyl chloride (18 mg, 0.14 mmol), whereby the title compound (101 mg, 56%) was obtained as colorless crystals.

$^1$H—NMR(CDCl$_3$) 67 : 0.92(3H,t,7 Hz), 1.14(3H,s), 1.24 (3H,s), 1.49–1.58(2H,m), 1.68(3H,s,C$_{19}$-Me), 1.85–1.94 (1H,m), 1.89(3H,s,C$_{18}$-Me), 2.27–2.43(5H,m), 2.42(3H,s), 2.44–2.58(4H,m), 3.15(1H,m), 3.37–3.76(4H,m), 3.81(1H, d,J=7 Hz,C$_3$—H), 4.21(1H,d,J=9 Hz,C$_{20}$—H), 4.30(1H,d, J=9 Hz,C$_{20}$—H), 4.44(1H,m), 4.82(1H,d,J=2 Hz,C$_2$,—H), 4.98(1H,d,J=8 Hz,C$_5$—H), 5.67(1H,d,J=7 Hz,C$_2$—H), 5.83 (1H,m), 6.26(1H,t,J=8 Hz,C$_{13}$—H), 6.26(1H,s,C$_{10}$—H), 6.38–6.42(2H,m), 6.47(1H,m), 7.01–7.09(2H,m), 7.44–7.55 (2H,m), 7.60–7.65(1H,m), 8.12–8.15(2H,m).

SIMS m/z: 946(M+H)$^+$

Example 46

13-0-[3-(2-Furyl)-2-hydroxy-3-isopropyloxycarbonylaminopropionyl]-10-0-(4-propylpiperazinocarbonyl)-10-deacetylbaccatin III (Compound 1-25)

In a similar manner to Example 42, the reaction and after-treatment were conducted using Compound (2-15) (215 mg, 0.188 mmol) of Example 28 and isopropyl chloroformate (17 mg, 0.139 mmol), whereby the title compound (60 mg, 34%) was obtained as colorless crystals.

$^1$H—NMR(CDCl$_3$) δ: 0.92(3H,t,J=7 Hz), 1.11(3H,d,J=6 Hz), 1.15(3H,s), 1.17(3H,d,J=6 Hz), 1.26(3H,s), 1.49–1.58 (2H,m), 1.68(3H,s,C$_{19}$-Me), 1.87–1.96(1H,m), 1.91(3H,s, C$_{18}$-Me), 2.25–2.43(5H,m), 2.40(3H,s), 2.44–2.58(4H,m), 3.20(1H,br-s), 3.40–3.76(4H,m), 3.81(1H,d,J=7 Hz,C$_3$—H), 4.19(1H,d,J=9 Hz,C$_{20}$—H), 4.29(1H,d,J=9 Hz,C$_{20}$—H), 4.44(1H,dd,J=7 Hz,11 Hz,C$_7$—H), 4.73(1H,s), 4.75–4.83 (1H,m), 4.98(1H,d,J=8 Hz,C$_5$—H), 5.38(2H,s), 5.67(1H,d, J=7 Hz,C$_2$—H), 6.27(1H,t,J=8 Hz,C$_{13}$—H), 6.27(1H,s, C$_{10}$—H), 6.30–6.34(1H,m), 6.37–6.39(1H,m), 7.40–7.44 (1H,m), 7.49–7.53(2H,m), 7.59–7.65(1H,m), 8.10–8.15(2H, m).

SIMS m/z: 938(M+H)$^+$

Example 47

13-0-[3-(tert-Amyloxycarbonylamino)-3-(2-furyl)-2-hydroxypropionyl]-10-0-(4-propylpiperazinocarbonyl)-10-deacetylbaccatin III (Compound 1-26)

In a similar manner to Example 4, the reaction and after-treatment were conducted using Compound (2-15) (215 mg, 0.188 mmol) of Example 28 and di-t-amyl dicarbonate (35 mg, 0.141 mmol), whereby the title compound (81 mg, 45%) was obtained as colorless crystals.

$^1$H—NMR(CDCl$_3$) δ: 0.80(3H,t,J=7 Hz), 0.92(3H,t,J=7 Hz), 1.15(3H,s), 1.26(3H,s), 1.31(6H,d,J=4 Hz), 1.49–1.58 (2H,m), 1.68(3H,s,C$_{19}$-Me), 1.85–1.96(1H,m), 1.92(3H,s, C$_{19}$-Me), 2.28–2.43(5H,m), 2.40(3H,s), 2.45–2.58(4H,m), 3.19(1H,br-s), 3.40–3.76(4H,m), 3.81(1H,d,J=7 Hz,C$_3$—H), 4.19(1H,d,J=9 Hz,C$_{20}$—H), 4.29(1H,d,J=9 Hz,C$_{20}$—H)4.44 (1H,m,C$_7$—H), 4.72(1H,s), 4.98(1H,d,J=8 Hz,C$_5$—H), 5.21–5.27(1H,m), 5.32–5.38(1H,m), 5.67(1H,d,J=7 Hz,C$_2$—H), 6.25(1H,t,J=8 Hz,C$_{13}$—H), 6.27(1H,s,C$_{10}$—H), 6.30–6.34(1H,m), 6.36–6.39(1H,m), 7.40–7.44(1H,m), 7.48–7.53(2H,m), 7.59–7.65(1H,m), 8.10–8.14(2H,m).

SIMS m/z: 966(M+H)$^+$

Example 48

13-0-[3-Cyclohexylcarbonylamino-3-(2-furyl)-2-hydroxypropionyl]-10-0-(4-propylpiperazinocarbonyl)-10-deacetylbaccatin III (Compound 1-27)

In a similar manner to Example 42, the reaction and after-treatment were conducted using Compound (2-15) (215 mg, 0.188 mmol) of Example 28 and cyclohexylcarbonyl chloride (21 mg, 0.138 mmol), whereby the title compound (102 mg, 56%) was obtained as colorless crystals.

$^1$H—NMR(CDCl$_3$) δ: 0.92(3H,t,J=7 Hz), 1.15(3H,s), 1.18–1.42(2H,m), 1.26(3H,s), 1.49–1.58(2H,m), 1.60–1.95 (9H,m), 1.68(3H,s,C$_{19}$-Me), 1.85–1.96(1H,m), 1.89(3H,s, C$_{18}$-Me), 2.28–2.43(5H,m), 2.39(3H,s), 2.43–2.58(4H,m), 3.15(1H,m), 3.40–3.76(4H,m), 3.81(1H,d,J=7 Hz,C$_3$—H), 4.19(1H,d,J=9 Hz,C$_{20}$—H), 4.29(1H,d,J=9 Hz,C$_{20}$—H), 4.44(1H,m,C$_7$—H), 4.73(1H,d,J=2 Hz,C$_2$,—H), 4.98(1H,d, J=8 Hz,C$_5$—H), 5.64–5.71(2H,m), 6.12–6.17(1H,m), 6.20 (1H,t,J=8 Hz,C$_{13}$—H), 6.27(1H,s,C$_{10}$—H), 6.30–6.33(1H, m), 6.37–6.40(1H,m), 7.40–7.44(1H,m), 7.48–7.53(2H,m), 7.59–7.65(1H,m), 8.10–8.14(2H,m).

SIMS m/z: 962(M+H)$^+$

Example 49

13-0-[3-Cyclpentylcarbonylamino-3-(2-furyl)-2-hydroxypropionyl]-10-0-(4-propylpiperazinocarbonyl)-10-deacetylbaccatin III (Compound 1-28)

In a similar manner to Example 42, the reaction and after-treatment were conducted using Compound (2-15) (215 mg, 0.188 mmol) of Example 28 and cyclopentylcarbonyl chloride (18 mg, 0.138 mmol), whereby the title compound (106 mg, 60%) was obtained as colorless crystals.

$^1$H—NMR(CDCl$_3$) δ: 0.92(3H,t,J=7 Hz), 1.15(3H,s), 1.26(3H,s), 1.49–1.58(2H,m), 1.55–1.75(9H,m), 1.68(3H,s, C$_{19}$-Me), 1.86–1.96(1H,m), 1.90(3H,s,C$_{19}$-Me), 2.28–2.42 (5H,m), 2.39(3H,s), 2.43–2.58(4H,m), 3.16(1H,m), 3.40–3.76(4H,m), 3.81(1H,d,J=7 Hz,C$_3$—H), 4.19(1H,d, J=9 Hz,C$_{20}$—H), 4.29(1H,d,J=9 Hz,C$_{20}$—H), 4.44(1H,m, C$_7$—H), 4.73(1H,d,J=2 Hz,C$_2$,—H), 4.98(1H,d,J=7 Hz,C$_5$—H), 5.67–5.71(2H,m), 6.10–6.15(1H,m), 6.21(1H,t, J=8 Hz,C$_{13}$—H), 6.27(1H,s,C$_{10}$—H), 6.30–6.33(1H,m), 6.37–6.40(1H,m), 7.41–7.44(1H,m), 7.48–7.53(2H,m), 7.59–7.65(1H,m), 8.10–8.14(2H,m).

SIMS m/z : 948(M+H)$^+$

Example 50

13-0-[3-Cyclohexyloxycarbonylamino-3-(2-furyl)-2-hydroxypropionyl]-10-0-(4-propylpiperazinocarbonyl)-10-deacetylbaccatin III (Compound 1-29)

In a similar manner to Example 42, the reaction and after-treatment were conducted using Compound (2-15)

(215 mg, 0.188 mmol) of Example 28 and cyclohexyl chloroformate (23 mg, 0.14 mmol), whereby the title compound (74 mg, 40%) was obtained as colorless crystals.

$^1$H—NMR(CDCl$_3$) δ: 0.93(3H,t,J=7 Hz), 1.15(3H,s), 1.26(3H,s), 1.49–1.58(2H,m), 1.60–1.75(11H,m), 1.68(3H, s,C$_{19}$-Me), 1.85–1.96(1H,m), 1.91(3H,s,C$_{18}$-Me), 2.22–2.45 (5H,m), 2.41(3H,s), 2.46–2.59(4H,m), 3.19(1H,m), 3.40–3.76(4H,m), 3.81(1H,d,J=7 Hz,C$_3$—H), 4.18(1H,d, J=9 Hz,C$_{20}$—H) 4.30(1H,d,J=9 Hz,C$_{20}$—H), 4.46(1H,m, C$_7$—H), 4.74(1H,d,J=2 Hz,C$_2$,—H), 4.98(1H,d,J=8 Hz,C$_5$—H), 5.32–5.43(2H,m), 5.66(1H,d,J=7 Hz,C$_2$—H), 6.21(1H,t,J=8 Hz,C$_{13}$—H), 6.27(1H,s,C$_{10}$—H), 6.31–6.35 (1H,m), 6.38–6.41(1H,m), 7.41–7.45(1H,m), 7.47–7.54(2H, m), 7.59–7.65(1H,m), 8.11–8.17(2H,m).

SIMS m/z: 978(M+H)$^+$

Example 51

13-0-[3-Cyclopentyloxycarbonylamino-3-(2-furyl)-2-hydroxypropionyl]-10-0-(4-propylpiperazinocarbonyl)-10-deacetylbaccatin III (Compound 1-30)

In a similar manner to Example 42, the reaction and after-treatment were conducted using Compound (2-15) (215 mg, 0.188 mmol) of Example 28 and cyclopentyl chloroformate (21 mg, 0.14 mmol), whereby the title compound (66 mg, 36%) was obtained as colorless crystals.

$^1$H—NMR(CDCl$_3$) 67 : 0.92(3H,t,J=7 Hz), 1.15(3H,s), 1.27(3H,s), 1.49–1.58(2H,m), 1.60–1.75(9H,m), 1.68(3H,s, C$_{19}$-Me), 1.85–1.96(1H,m), 1.91(3H,s,C$_{18}$-Me), 2.25–2.42 (5H,m), 2.40(3H,s), 2.44–2.60(4H,m), 3.19(1H,m), 3.40–3.77(4H,m), 3.81(1H,d,J=7 Hz,C$_3$—H), 4.19(1H,d, J=9 Hz,C$_{20}$—H), 4.30(1H,d,J=9 Hz,C$_{20}$—H), 4.44(1H,m, C$_7$—H), 4.73(1H,d,J=2 Hz,C$_2$,—H), 4.97(1H,d,J=8 Hz,C$_5$—H), 5.30–5.43(2H,m), 5.67(1H,d,J=2 Hz,C$_2$—H), 6.27(1H,t,J=8 Hz,C$_{13}$—H), 6.27(1H,s,C$_{10}$—H), 6.30–6.34 (1H,m), 6.37–6.40(1H,m), 7.40–7.45(1H,m), 7.46–7.55(2H, m), 7.58–7.65(1H,m), 8.10–8.16(2H,m).

SIMS m/z: 964(M+H)$^+$

Example 52

13-0-[3-Cyclopropanecarbonylamino-3-(2-furyl)-2-hydroxypropionyl]-10-0-(4-methylpiperazinocarbonyl)-10-deacetylbaccatin III (Compound 1-31)

In a similar manner to Example 42, the reaction and after-treatment were conducted using Compound (2-8) (0.12 g, 0.11 mmol) of Example 17 and cyclopropanecarbonyl chloride (10 mg, 0.1 mmol), whereby the title compound (26 mg, 20%,) was obtained.

$^1$H—NMR(CDCl$_3$) δ: 0.65–0.71(m,2H), 0.75–0.84(m, 2H), 1.08(s,3H), 1.19(s,3H), 1.32(m,1H), 1.61(s.3H), 1.70 (s,1H), 1.80(m,1H,C$_6$—H), 1.83(s,3H), 2.17(m,1H,C$_{14}$—H), 2.27(m,1H,C$_{14}$—H), 2.28(s,3H), 2.32(s,3H), 2.35–2.52 (m,5H), 3.07(d,J=4 Hz,1H), 3.31–3.68(m,4H), 3.73(d,J=7 Hz,1H,C$_3$—H), 4.11(d,J=8 Hz,1H,C$_{20}$—H), 4.22(d,J=8 Hz,1H,C$_{20}$—H), 4.38(m,1H,C$_7$—H), 4.66(d,J=3 Hz,1H, C$_2$,—H), 4.89(d,J=7 Hz,1H,C$_5$—H), 5.60(d,J=7 Hz,1H, C$_2$—H), 5.62(dd,J=9,2 Hz,1H,C$_3$,—H), 6.16(t,J=10 Hz,1H, C$_{13}$—H), 6.20(s,1H,C$_{10}$—H), 6.23(d,J=9 Hz,1H,NH), 6.29 (m,1H), 6.32(m,1H), 7.36(m,1H), 7.43(t,J=8 Hz,2H), 7.54 (t,J=7 Hz,1H), 8.04(d,J=8 Hz,2H)

SI-MS m/z: 892 [M+H]$^+$

Example 53

13--0-[3-(2-Furyl)-2-hydroxy-3-trifluoroacetylaminopropionyl]-10-0-(4-methylpiperazinocarbonyl)-10-deacetylbaccatin III (Compound 1-32)

In a similar manner to Example 16, the reaction and after-treatment were conducted using Compound (2-8) (0.12 g, 0.11 mmol) of Example 17 and trifluoroacetic anhydride (21 mg, 0.1 mmol), whereby the title compound (5 mg, 5%) was obtained.

$^1$H—NMR(CDCl$_3$) δ: 1.08(s,3H), 1.19(s,3H), 1.62(s.3H), 1.68(s,1H), 1.78(m,1H,C$_6$—H), 1.81(s,3H), 2.1–2.28(m,2H, C$_{14}$—Hx2), 2.29(s,3H), 2.30(s,3H), 2.38–2.50(m,5H), 3.06 (s,$_1$1H), 3.37–3.66(m,4H), 3.73(d,J=7 Hz,1H,C$_3$—H), 4.14 (d,J=8 Hz,1H,C$_{20}$—H), 4.23(d,J=8 Hz,1H,C$_{20}$—H), 4.36(m, 1H,C$_7$—H), 4.71(d,J=2 Hz,1H,C$_2$,—H), 4.88(d,J=8 Hz,1H, C$_5$—H), 5.60(d,J=7 Hz,1H,C$_2$—H), 5.61(dd,J=9,2 Hz,1H, C$_3$,—H), 6.20(s,1H,C$_{10}$—H), 6.21(t,J=10 Hz,1H,C$_{13}$—H), 6.35–6.36(m,2H), 7.03(d,J=9 Hz,1H,NH), 7.39(m,1H), 7.43 (t,J=8 Hz,2H), 7.54(t,J=7 Hz,1H), 8.03(d,J=8 Hz,2H)

SI-MS m/z: 919[M+H]$^+$

Example 54

13-0-(3-Benzyloxycarbonyl-2,2-dimethyl-4-ethyl-5-oxazolidinecarbonyl)-10-0-(4-methylpiperazinocarbonyl)-7-0-triethylsilyl-10-deacetylbaccatin III (Compound 2-22)

In a similar manner to Example 1, the reaction and after-treatment were conducted using 10-0-(4-methylpiperazinocarbonyl)-7-0-triethylsilyl-10-deacetylbaccatin III (100 mg, 0.13 mmol) and 3-benzyloxycarbonyl-2,2-dimethyl-4-ethyl-5-oxazolidinecarboxylic acid (200 mg, 0.65 mmol), whereby the title compound (140 mg, 100%) was obtained.

$^1$H—NMR(CDCl$_3$) δ: 0.56(m,6H), 0.91(t,J=8 Hz,9H), 0.92(t,J=8 Hz,3H), 1.14(s,3H), 1.18(s,3H), 1.54(s,3H), 1.60 (s,3H), 1.65(s,3H), 1.70–1.95(m,3H), 2.06(s,3H), 2.18–2.90 (m,7H), 2.33(s,3H), 2.50(s,3H), 3.20–3.90(m,4H), 3.82(d, J=7 Hz,1H,C$_3$—H), 4.11(d,J=9 Hz,1H,C$_{20}$—H), 4.26–4.33 (m,2H), 4.32(d,J=9 Hz,1H,C$_{20}$—H), 4.46(m,1H,C$_7$—H), 4.92(d,J=10 Hz,1H,C$_5$—H), 5.11(brs,1H), 5.17(d,J=12 Hz,1H), 5.65(d,J=7 Hz,1H,C$_2$—H), 6.16(t,J=9 Hz,1H,C$_{13}$—H), 6.38(s,1H,C$_{10}$—H), 7.30–7.40(m,5H), 7.46(t,J=8 Hz,2H), 7.60(t,J=7 Hz,1H), 8.05(d,J=8 Hz,2H)

Example 55

13-0-[3-(tert-Butoxycarbonylamino)-2-hydroxyvaleryl]-10-0-(4-methylpiperazinocarbonyl)-10-deacetylbaccatin III (Compound 1-33)

In a similar manner to Example 16, the reaction and after-treatment were conducted using Compound (2-22) (0.14 g, 0.13 mmol) of Example 54 and di-tert-butyl dicarbonate (32 mg, 0.15 mmol), whereby the title compound (20 mg, 18%) was obtained.

$^1$H—NMR(CDCl$_3$) δ: 0.94(t,J=7 Hz,3H), 1.19(s,3H), 1.24(s,3H), 1.26(s,9H), 1.61(s.3H), 1.65(m,2H), 1.81(m,1H, C$_6$—H), 1.85(s,3H), 2.20–2.98(m,7H), 2.33(s,3H), 2.36(s, 3H), 3.14(s,1H), 3.23–3.92(m,4H), 3.73(d,J=7 Hz,1H,C$_3$—H), 3.98(m,1H,C$_3$—H), 4.11(d,J=9 Hz,1H,C$_{20}$—H), 4.21 (d,J=3 Hz,1H,C$_{20}$—H), 4.25(d,J=9 Hz,1H,C$_{20}$—H), 4.36(m, 1H,C$_7$—H), 4.58(d,J=10 Hz,1H,NH), 4.91(d,J=10 Hz,1H, C$_5$—H), 5.60(d,J=7 Hz,1H,C$_2$—H), 6.14(t,J=9 Hz,1H, C$_{13}$—H), 6.22(s,1H,C$_{10}$—H), 7.43(t,J=7 Hz,2H), 7.55(t,J=7 Hz,1H), 8.05(d,J=7 Hz,2H)

SI-MS m/z: 886 [M+H]$^+$

Example 56

13-0-[3-Benzyloxycarbonyl-4-(tert-butyl)-2,2-dimethyl-5-oxazolidinecarbonyl)-10-0-(4-methylpiperazinocarbonyl)-7-0-triethylsilyl-10-deacetylbaccatin III (Compound 2-23)

In a similar manner to Example 1, the reaction and after-treatment were conducted using 10-0-(4- methylpiperazinocarbonyl)-7-O-triethylsilyl-10-deacetylbaccatin III (100 mg, 0.13 mmol) and 3-benzyloxycarbonyl-4-(tert-butyl)-2,2-dimethyl-5-oxazolidinecarboxylic acid (80 mg, 0.24 mmol), whereby the title compound (0.14 mg, 98%) was obtained.

$^1$H—NMR(CDCl$_3$) δ: 0.57(m,6H), 0.91(t,J=8 Hz,9H), 0.93(s,9H), 1.16(s,3H), 1.17(s,3H), 1.53(s,3H), 1.64(s,3H), 1.66(s,3H), 1.86(m,1H,C$_6$—H), 2.11(s,3H), 2.17-2.90(m, 7H), 2.34(s,3H), 2.42(s,3H), 3.35-4.05(m,4H), 3.85(d,J=7 Hz,1H,C$_3$—H), 4.16(d,J=8 Hz,1H,C$_{20}$—H), 4.30(d,J=8 Hz,1H,C$_{20}$—H), 4.40(d,J=2 Hz,1H), 4.45(dd,J=9 Hz,6 Hz,1H,C$_7$—H), 4.55(brs,1H), 4.93(d,J=8 Hz,1H,C$_5$—H), 5.10(brs,1H), 5.15(d,J=12 Hz,1H), 5.66(d,J=7 Hz,1H,C$_2$—H), 6.14(t,J=9 Hz,1H,C$_{13}$—H), 6.38(s,1H,C$_{10}$—H), 7.27-7.38(m,5H), 7.46(t,J=8 Hz,2H), 7.59(t,J=7 Hz,1H), 8.07(d,J=8 Hz,2H)

Example 57

13-O-[3-(tert-Butoxycarbonylamino)-4,4-dimethyl-2-hydroxyvaleryl]-10-O-(4-methylpiperazinocarbonyl)-10-deacetylbaccatin III (Compound 1-34)

In a similar manner to Example 16, the reaction and after-treatment were conducted using Compound (2-23) (0.08, 0.08 mmol) of Example 56 and di-tert-butyl dicarbonate (15 mg, 0.07 mmol), whereby the title compound (9 mg, 14%) was obtained.

$^1$H—NMR(CDCl$_3$) δ: 1.03(s,9H), 1.09(s,3H), 1.24(s,3H), 1.28(s,9H), 1.65(s,3H), 1.86(m,1H,C$_6$—H), 1.90(s,3H), 2.20-3.02(m,7H), 2.37(s,3H), 2.40(s,3H), 3.05(s,1H), 3.20-3.97(m,4H), 3.76(d,J=7 Hz,1H,C$_3$—H), 3.77(m,1H, C$_3$,—H), 4.16(d,J=8 Hz,1H,C$_{20}$—H), 4.30(d,J=8 Hz,1H, C$_{20}$—H), 4.41(m,1H,C$_7$—H), 4.55(d,J=2 Hz,1H,C$_2$,—H), 4.87(d,J=11 Hz,1H,NH), 4.96(d,J=8 Hz,1H,C$_5$—H), 5.65(d, J=7 Hz,1H,C$_2$—H), 6.17(t,J=9 Hz,1H,C$_{13}$—H), 6.28(s,1H, C$_{10}$—H), 7.48(t,J=7 Hz,2H), 7.60(t,J=7 Hz,1H), 8.11(d,J=7 Hz,2H)

SI-MS m/z: 914 [M+H]$^+$

Example 58

13-O-(3-Benzyloxycarbonyl-4-cyclopropyl-2,2-dimethyl-5-oxazolidinecarbonyl)-10-O-(4-methylpiperazinocarbonyl)-7-O-triethylsilyl-10-deacetylbaccatin III (Compound 2-24)

In a similar manner to Example 1, the reaction and after-treatment were conducted using 10-O-(4-methylpiperazinocarbonyl)-7-O-triethylsilyl-10-deacetylbaccatin III (503 mg, 0.64 mmol) and 3-benzyloxycarbonyl-4-cyclopropyl-2,2-dimethyl-5-oxazolidinecarboxylic acid (306 mg, 0.96 mmol), whereby the title compound (quant.) was obtained.

$^1$H—NMR(CDCl$_3$) δ: 0.21(m,1H), 0.45(m,1H), 0.52-0.81(m,8H), 0.90(t,J=8 Hz,9H), 1.06(m,1H), 1.17(s, 3H), 1.18(s,3H), 1.63(s,3H), 1.65(s,3H), 1.66(s,3H), 1.86 (m,1H,C$_6$—H), 2.12(s,3H), 2.22(m,2H), 2.26-2.55(m,5H), 2.30(s,3H), 2.34(s,3H), 3.23-3.80(m,4H), 3.85(d,J=7 Hz,1H,C$_3$—H), 3.90(m,1H), 4.13(d,J=8 Hz,1H,C$_{20}$—H), 4.29(d,J=8 Hz,1H,C$_{20}$—H), 4.44(d,J=2 Hz,1H), 4.47(m,1H, C$_7$—H), 4.93(d,J=8 Hz,1H,C$_5$—H), 5.09(d,J=12 Hz,1H), 5.16(d,J=12 Hz,1H), 5.66(d,J=7 Hz,1H,C$_2$—H), 6.13(t,J=9 Hz,1H,C$_{13}$—H), 6.37(s,1H,C$_{10}$—H), 7.30-7.40(m,5H), 7.45(t,J=8 Hz,2H), 7.59(t,J=7 Hz,1H), 8.06(d, J=7 Hz,2H)

Example 59

13-O-[3-(tert-Butoxycarbonylamino)-3-cyclopropyl-2-hydroxypropionyl]-10-O- (4-methylpiperazinocarbonyl)-10-deacetylbaccatin III (Compound 1-35)

In a similar manner to Example 16, the reaction and after-treatment were conducted using Compound (2-24) (0.15 g, 0.14 mmol) of Example 58 and di-tert-butyl dicarbonate (32 mg, 0.15 mmol), whereby the title compound (22 mg, 17%) was obtained.

$^1$H—NMR(CDCl$_3$) δ: 0.25(m,1H), 0.46(m,1H), 0.56-0.68(m,2H), 1.12(s,3H), 1.21(m,$_1$H), 1.23(s,3H), 1.30 (s.9H), 1.58(s,3H), 1.65(s,1H), 1.86(m,1H,C$_6$—H), 1.90(s, 3H), 2.00-2.10(m,2H), 2.31(m,1H,C$_6$—H), 2.33(s,3H), 2.34 (s,3H), 2.36-2.58(m,4H), 3.12(s,1H), 3.28(dt,J=9,2 Hz,1H), 3.36-3.76(m,4H), 3.77(d,J=7 Hz,1H,C$_3$—H), 4.15(d,J=8 Hz,1H,C$_{20}$—H), 4.29(d,J=8 Hz,1H,C$_{20}$—H), 4.37(d,J=2 Hz,1H), 4.43(m,1H,C$_7$—H), 4.86(d,J=8 Hz,1H,NH), 4.96(d, J=7 Hz,1H,C$_5$—H), 5.64(d,J=7 Hz,1H,C$_2$—H), 6.16(t,J=9 Hz,1H,C$_{13}$—H), 6.25(s,1H,C$_{10}$—H), 7.48(t,J=8 Hz,2H), 7.59(t,J=7 Hz,1H), 8.09 (d, J=7 Hz, 2H)

SI-MS m/z: 898[M+H]$^+$

Example 60

13-O-(3-Butylylamino-3-cyclopropyl-2-hydroxypropionyl)-10-O-(4-methylpiperazinocarbonyl)-10-deacetylbaccatin III (Compound 1-36)

In a similar manner to Example 42, the reaction and after-treatment were conducted using Compound (2-24) (0.15 g, 0.14 mmol) of Example 58 and butyl chloride (13 mg, 0.12 mmol), whereby the title compound (19 mg, 15%) was obtained.

$^1$H—NMR(CDCl$_3$) δ: 0.31(m,1H), 0.43(m,1H), 0.56-0.73(m,2H), 0.89(t,J=7 Hz,3H), 1.14(s,3H), 1.25(s, 3H), 1.28(m,1H), 1.57(m,2H), 1.68(s,3H), 1.82(m,1H,C$_6$—H), 1.91(s,3H), 2.12(m,2H), 2.26-2.38(m,3H), 2.36(s,3H), 2.37(s,3H), 2.42-2.58(m,4H), 3.14(s,1H), 3.40-3.79(m,4H), 3.61(dt,J=9.1 Hz,1H), 3.78(d,J=7 Hz,1H,C$_3$—H), 4.19(d, J=8 Hz,1H,C$_{20}$—H), 4.31(d,J=8 Hz,1H,C$_{20}$—H) 4.43(d,J=1 Hz, 1H) , 4.45 (m,1H,C$_7$—H), 4.98(d, J=9 Hz, 1H,C$_5$—H) 5.68(d,J=7 Hz,1H,C$_2$—H), 5.84(br,1H,NH), 6.16(t,J=9 Hz,1H,C$_{13}$—H), 6.27(s,1H,C$_{10}$—H), 7.50(t,J=8 Hz,2H), 7.59(t,J=7 Hz,1H), 8.11(d,J=8 Hz,2H)

SI-MS m/z: 867[M+H]$^+$

Example 61

13-O-(Cyclopropyl-3-n-hexanoylamino-2-hydroxypropionyl)-10-O-(4-methylpiperazinocarbonyl)-10-deacetylbaccatin III (Compound 1-37)

In a similar manner to Example 42, the reaction and after-treatment were conducted using Compound (2-24) (0.15 g, 0.14 mmol) of Example 58 and n-hexanoyl chloride (16 mg, 0.12 mmol), whereby the title compound (11 mg, 9%) was obtained.

$^1$H—NMR(CDCl$_3$) δ: 0.31(m,1H), 0.43(m,1H), 0.56-0.73(m,2H), 0.84(t,J=7 Hz,3H), 1.14(s,3H), 1.22-1.34 (m,5H), 1.26(s,3H), 1.55(m,2H), 1.67(s,3H), 1.84(m,1H, C$_6$—H), 1.91(s,3H), 2.12(m,2H), 2.26-2.39(m,3H), 2.34(s, 3H), 2.38(s,3H), 2.41-2.58(m,4H), 3.12(s,1H), 3.36-3.79 (m,4H), 3.61(dt,J=10,2 Hz,1H), 3.78(d,J=7 Hz,1H,C$_3$—H), 4.19(d,J=8 Hz,1H,C$_{20}$—H), 4.31(d,J=8 Hz,1H,C$_{20}$—H), 4.43(d,J=22 Hz,1H) 4.45(m,1H,C$_7$—H), 4.98(d,J=7 Hz,1H, C$_5$—H) 5.68(d,J=7 Hz,1H,C$_2$—H), 5.77(d,J=9 Hz,1H,NH), 6.17(t,J=9 Hz,1H,C$_{13}$—H), 6.26(s,1H,C$_{10}$—H), 7.50(t,J=8 Hz,2H), 7.61(t,J=7 Hz,1H), 8.11(d,J=7 Hz,2H)

SI-MS m/z: 896[M+H]$^+$

Example 62

13-O-(3-Benzyloxycarbonyl-4-cyclopropyl-2,2-dimethyl-5--oxazolidinecarbonyl)-10-O-(4-propylpiperazinocarbonyl)-7-O-triethylsilyl-10-deacetylbaccatin III (Compound 2-25)

In a similar manner to Example 1, the reaction and after-treatment were conducted using Compound (2-14)

(820 mg, 1.00 mmol) of Example 27 and 3-benzyloxycarbonyl-4-cyclopropyl-2,2-dimethyl-5-oxazolidinecarboxylid acid (500 mg, 1.56 mmol), whereby the title compound (quant.) was obtained.

$^1$H—NMR(CDCl$_3$) δ: 0.21(m,1H), 0.46(m,1H), 0.50–0.58(m,8H), 0.90(t,J=8 Hz,3H), 0.95(t,J=8 Hz,9H), 1.11(s,3H), 1.21(m,1H), 1.22(s,3H), 1.52(m,2H), 1.64(s, 3H), 1.65(s,3H), 1.66(s,3H), 1.75–2.00(m,3H), 1.94(s,3H), 2.23(m,2H), 2.33(m,1H), 2.34(s,3H), 2.40–2.61(m,4H), 3.34–3.73(m,4H), 3.81(d,J=7 Hz,1H,C$_3$—H), 3.89(m,1H), 4.13(d,J=8 Hz,1H,C$_{20}$—H), 4.30(d,J=8 Hz,1H,C$_{20}$—H), 4.45(d,J=3 Hz,1H), 4.50(m,1H,C$_7$—H), 4.97(d,J=8 Hz,1H, C$_5$—H), 5.09(d,J=12 Hz,1H), 5.16(d,J=12 Hz,1H), 5.64(d, J=7 Hz,1H,C$_2$—H), 6.17(t,J=8 Hz,1H,C$_{13}$—H), 6.25(s,1H, C$_{10}$—H), 7.27–7.38(m,5H), 7.47(t,J=8 Hz,2H), 7.60(t,J=7 Hz,1H), 8.06(d,J=7 Hz,2H)

Example 63

13-0-[3-(tert-Butoxycarbonylamino)-3-cyclopropyl-2-hydroxypropionyl]-10-0-(4-propylpiperazinocarbonyl)-10-deacetylbaccatin III (Compound 1-38)

In a similar manner to Example 16, the reaction and after-treatment were conducted using Compound (2-25) (0.20 g, 0.20 mmol) of Example 62 and di-tert-butyl dicarbonate (85 mg, 0.40 mmol), whereby the title compound (33 mg, 18%) was obtained.

$^1$H—NMR(CDCl$_3$) δ: 0.26(m,1H), 0.45(m,1H), 0.60–0.64(m,2H), 0.90(t,J=7 Hz,3H), 1.12(s,3H), 1.20(m, 1H), 1.23(s,3H), 1.30(s,9H), 1.52(m,2H), 1.65(s,3H), 1.66 (s,1H), 1.86(m,1H,C$_6$—H), 1.90(s,3H), 2.25–2.38(m,5H), 2.34(s,3H), 2.41–2.58(m,4H), 3.15(s,1H), 3.29(dt,J=10,2 Hz,1H), 3.36–3.74(m,4H), 3.77(d,J=7 Hz,1H,C$_3$—H), 4.15 (d,J=8 Hz,1H,C$_{20}$—H), 4.29(d,J=8 Hz,1H,C$_{20}$—H), 4.37(d, J=2 Hz,1H), 4.43(m,1H,C$_7$—H), 4.86(d,J=9 Hz,1H,NH), 4.96(d,J=8 Hz,1H,C$_5$—H), 5.64(d,J=7 Hz,1H,C$_2$—H), 6.16 (t,J=9 Hz,1H,C$_{13}$—H), 6.25(s,1H,C$_{10}$—H), 7.47(t,J=8 Hz,2H), 7.59(t,J=7 Hz,1H), 8.09(d,J=7 Hz,2H)

SI-MS m/z: 926[M+H]$^+$

Example 64

13-0-(3-Cyclopropyl-2-hydroxy-3-(2-thenoylamino) propionyl]-10-0-(4-propylpiperazinocarbonyl)-10-deacetylbaccatin III (Compound 1-39)

In a similar manner to Example 42, the reaction and after-treatment were conducted using Compound (2-25) (0.20 g, 0.20 mmol) of Example 62 and 2-thenoyl chloride (48 mg, 0.33 mmol), whereby the title compound (70 mg, 33%) was obtained.

$^1$H—NMR(CDCl$_3$) 67 : 0.38(m,1H), 0.52(m,1H), 0.60–0.75(m,2H), 0.90(t,J=7 Hz,3H), 1.11(s,3H), 1.20(s, 3H), 1.35(m,1H), 1.50(m,2H), 1.66(s,3H), 1.71(s,1H), 1.88 (s,3H), 90(m,1H,C$_6$—H), 2.20–2.35(m,3H), 2.40(s,3H), 2.41–2.58(m,6H), 3.13(s,1H), 3.34–3.74(m,5H), 3.77(d,J=7 Hz,1H,C$_3$—H), 3.83(dt,J=9,1 Hz,1H), 4.19(d,J=8 Hz,1H, C$_{20}$—H), 4.28(d,J=8 Hz,1H,C$_{20}$—H), 4.43(m,1H,C$_7$—H), 4.51(d,J=1 Hz,1H), 4.96(d,J=8 Hz,1H,C$_5$—H), 5.64(d,J=7 Hz,1H,C$_2$—H), 6.23(t,-J=10 Hz,1H,C$_{13}$—H), 6.26(s,1H, C$_{10}$—H), 6.33(d,J=9 Hz,1H,NH), 7.03(dd,J=4,5 Hz,1H), 7.24–7.47(m,2H), 7.50(t,J=8 Hz,2H), 7.60(t,J=7 Hz,1H), 8.11(d,J=7 Hz,2H)

SI-MS m/z: 936 [M+H]$^+$

Example 65

13-0- [3- (3, 3-Dimethylacryloylamino) -3-cyclopropyl-2-hydroxypropionyl]-10-0- (4-propylpiperazinocarbonyl) -10-deacetylbaccatin III (Compound 1-40)

In a similar manner to Example 42, the reaction and after-treatment were conducted using Compound (2-25) (0.20 g, 0.20 mmol) of Example 62 and 3,3-dimethylacryloyl chloride (18 mg, 0.15 mmol), whereby the title compound (20 mg, 11%) was obtained.

$^1$H—NMR(CDCl$_3$) 67 : 0.24 (m,1H) , 0.37 (m,1H), 0.51–0.65(m,2H), 0.85(t,J=7 Hz,3H), 1.07(s,3H), 1.18(s, 3H), 1.21(m,1H), 1.46(m,2H), 1.60(s,3H), 1.73(d,J=1 Hz,3H), 1.80(m,1H,C$_6$—H), 1.84(s,3H), 1.92(d,J=1 Hz,3H), 2.20–2.34(m,5H), 2.33(s,3H), 2.35–2.50(m,4H), 3.09(s,1H), 3.31–3.70(m,4H), 3.55(dt,J=10,2 Hz,1H), 3.72(d,J=7 Hz,1H,C$_3$—H), 4.11(d,J=8 Hz,1H,C$_{20}$—H), 4.37 (d,J=8 Hz,1H,C$_{20}$—H), 4.37(d,J=2 Hz,1H), 4.48(m,1H,C$_7$—H), 4.92(d,J=8 Hz,1H,C$_5$—H), 5.46(s,1H), 5.60(d,J=7 Hz,1H, C$_2$—H), 5.64(d,J=8 Hz,1H,NH), 6.11(t,J=9 Hz,1H,C$_{13}$—H), 6.20(s,1H,C$_{10}$—H), 7.42(t,J=8 Hz,2H), 7.54(t,J=7 Hz,1H), 8.03(d,J=7 Hz,2H)

SI-MS m/z: 908[M+H]+

Example 66

13-0- [3-Benzyloxycarbonyl-2,2-dimethyl-4- (4-fluorophenyl) -5-oxazolidinecarbonyl) -10-0- (4-propylpiperazinocarbonyl) -7-0-triethylsilyl-10-deacetylbaccatin III (Compound 2-26)

In a similar manner to Example 1, the reaction and after-treatment were conducted using Compound (2-14) (2.1 g, 2.59 mmol) of Example 27 and 3-benzyloxycarbonyl-2, 2-dimethyl-4-(4-fluorophenyl)-5-oxazolidinecarboxylic acid (1.16 g, 3.11 mmol), whereby the title compound (3.02 g, 99%) was obtained.

$^1$H—NMR(CDCl$_3$) δ: 0.53–0.65(6H,m,SiCH$_2$), 0.92(3H, t,J=7 Hz,CH$_2$CH$_2$CH$_3$), 0.92(9H,t,J=8 Hz,SiCH$_2$CH$_3$), 1.19 (2×3H,s,C$_{16,17}$), 1.48–1.57(2H,m,CH$_2$CH$_2$CH$_3$), 1.66(3H,s, C$_{19}$), 1.75(3H,s,isopropylidene), 1.81(3H,s,isopropylidene), 1.82–1.90(1H,m,C$_6$), 1.97(3H,s), 2.12(s,3H), 2.16(2H,d,J= 9.0 Hz,C$_{14}$), 2.31–2.35(2H,m,CH$_2$CH$_2$CH$_3$), 2.36–2.55(4H, m,piperazine), 2.45–2.53(1H,m,C$_6$), 3.35–3.90(4H,m, piperazine), 3.81(1H,d,J=6.8 Hz,C$_3$), 4.11(1H,d,J=8.4 Hz,C$_{20}$), 4.26(1H,d,J=8.4 Hz,C$_{20}$), 4.43–4.47 (1H,m,C$_7$), 4.47(1H,d,J=6.1 Hz,C$_2$,), 4.80–5.10(2H,m,PhCH$_2$), 4.89–4.91(1H,m,C$_5$), 5.21(1H,brs,C$_3$,), 5.66(1H,d,J=7.1 Hz,C$_2$), 6.21–6.25(1H,m,C$_{13}$), 6.38(1H,s,C$_{10}$), 6.80–7.40 (9H,m,aromatic), 7.49(2H,t,J=7.7 Hz,Bz), 7.60–7.64(1H,m, Bz), 8.03–8.05(2H,m,Bz).

Example 67

13-0-[3-(tert-Butoxycarbonylamino)-3-(4-fluorophenyl)-2-hydroxypropionyl]-10-0-(4-propylpiperazinocarbonyl)-10-deacetylbaccatin III (Compound 1-41)

In a similar manner to Example 16, the reaction and after-treatment were conducted using Compound (2-26) 0.16 g, 0.13 mmol) of Example 66 and di-tert-butyl dicarbonate (32 mg, 0.15 mmol), whereby the title compound (88 mg, 75%) was obtained.

$^1$H—NMR(CDCl$_3$) δ: 0.96(t,J=7 Hz,3H), 1.13(s,3H), 1.24(s,3H), 1.31(s,9H), 1.51(m,2H), 1.65(s,3H), 1.68(s,1H), 1.85(s,3H), 1.86(m,1H,C$_6$—H), 2.26–2.38(m,4H), 2.34(s, 3H), 2.45–2.57(m,5H), 3.14(s,1H), 3.30–3.76(m,4H), 10 3.78(d,J=7 Hz,1H,C$_3$—H), 4.15(d,J=8 Hz,1H,C$_{20}$—H), 4.28 (d,J=8 Hz,1H,C$_{20}$—H), 4.42(m,1H,C$_7$—H), 4.58(s,1H, C$_2$,—H), 4.94(d,J=8 Hz,1H,C$_5$—H), 5.18(brs,1H,NH), 5.32 (d, 1H,J=9 Hz,C$_3$,—H), 5.64(d,J=7 Hz,1H,C$_2$—H), 6.24(m, 1H,C$_{13}$—H), 6.24(s,1H,C$_{10}$—H), 7.07(t,J=9 Hz,2H), 7.36 (m,2H), 7.48(t,J=8 Hz,2H), 7.59(t,J=7 Hz,1H), 8.09(d,J=7 Hz,2H)

Example 68

13-0-[3-(4-Fluorophenyl)-3-(n-hexanoylamino)-2-hydroxypropionyl]-10-0-(4-propylpiperazinocarbonyl)-10-deacetylbaccatin III (Compound 1–42)

In a similar manner to Example 42, the reaction and after-treatment were conducted using Compound (2–26) (361 mg, 0.309 mmol) of Example 66 and n-hexanoyl chloride (46 mg, 0.342 mmol), whereby the title compound (201 mg, 75%) was obtained as colorless crystals.

$^1$H—NMR(CDCl$_3$) δ: 0.83(3H,t,J=7.0 Hz,hexanoyl-CH$_3$), 0.92(3H,t,J=7.3 Hz,NCH$_2$CH$_2$CH$_3$), 1.15(3H,s,C$_{16}$ or C$_{17}$), 1.21–1.26(4H,m,hexanoyl-CH$_2$×2), 1.26(3H,s,C$_{16}$ or C$_{17}$), 1.48–1.57(4H,m,hexanoyl-CH$_2$ and NCH$_2$CH$_2$CH$_3$), 1.68(3H,s,C$_{19}$), 1.85–1.94(1H,m,C$_6$), 1.86(3H,s,C$_{18}$), 2.16–2.20(2H,m,C$_{14}$), 2.30–2.37(4H,m,hexanoyl-CH$_2$ and CH$_2$CH$_2$CH$_3$), 2.33(3H,s), 2.45–2.56(4H,m,piperazine), 2.50–2.60(1H,m,C$_6$), 3.17(1H,d,J=3.4 Hz,C$_7$—OH), 3.40–3.75(4H,m,piperazine), 3.78(1H,d,J=6.8 Hz,C$_3$), 4.19 (1H,d,J=8.4 Hz,C$_{20}$), 4.30(1H,d,J=8.4 Hz,C$_2$), 4.40–4.45 (1H,m,11 Hz,C$_7$), 4.65(1H,d,J=2.4 Hz,C$_{2'}$), 4.94–4.96(1H, m,C$_5$), 5.56–5.59(1H,m,C$_3'$), 5.67(1H,d,J=7.1 Hz,C$_2$), 6.22–6.25(1H,m,C$_{13}$), 6.22–6.26(1H,brs,NH), 6.26(1H,s,C$_{10}$), 7.06–7.11(2H,m,4FC$_6$H$_4$), 7.38–7.42(2H,m,4FC$_6$H$_4$), 7.49–7.52(2H,m,Bz), 7.59–7.63(1H,m,Bz), 8.10–8.12(2H, m,Bz).

SIMS m/z: 977(M)$^+$

Example 69

13-0-[3-(4-Fluorophenyl)-2-hydroxy-3-(2-thenoylamino)-propionyl]-10-0-(4-propylpiperazinocarbonyl)-10-deacetylbaccatin III (Compound 1–43)

In a similar manner to Example 42, the reaction and after-treatment were conducted using Compound (2–26) (361 mg, 0.309 mmol) of Example 66 and 2-thenoyl chloride (50 mg, 0.342 mmol), whereby the title compound (65 mg, 21%) was obtained as colorless crystals.

$^1$H—NMR(CDCl$_3$) δ: 0.92(3H,t,J=7.3 Hz,CH$_2$CH$_2$CH$_3$), 1.13(3H,s,C$_{16}$ or C$_{17}$), 1.22(3H,s,C$_{16}$ or C$_{17}$), 1.48–1.57(2H, m,CH$_2$CH$_2$CH$_3$), 1.68(3H,s,C$_{19}$), 1.83(3H,s,C$_{18}$), 1.87–1.93 (1H,m,C$_6$), 2.24–2.37(4H,m,C$_{14}$ and CH$_2$CH$_2$CH$_3$), 2.36 (3H,s), 2.40–2.55(5H,m,piperazine and C$_6$), 3.20(1H,brs, C$_7$—OH), 3.41–3.71(4H,m,piperazine), 3.78(1H,d,J=7.1 Hz,C$_3$), 4.20(1H,d,J=8.4 Hz,C$_{20}$), 4.29(1H,d,J=8.4 Hz,C$_{20}$), 4.39–4.44(1H,m,C$_7$), 4.75(1H,d,J=2.4 Hz,C$_{2'}$), 4.94–4.96 (1H,m,C$_5$), 5.66(1H,d,J=7.1 Hz,C$_2$), 5.73–5.75(1H,m,C$_3'$), 6.23–6.27(1H,m,C$_{13}$), 6.24(1H,s,C$_{10}$), 6.93–7.11(4H,m, 4FC$_6$H$_4$,thenoyl and NH), 6.38–6.39(1H,m), 7.46–7.53(6H, m,Bz,4FC$_6$H$_4$ and thenoyl), 7.60–7.64(1H,m,Bz), 8.12(2H, d, J=7.3 Hz,Bz).

SIMS m/z: 989(M)$^+$

Example 70

13-0-[3-(3,3-Dimethylacryloylamino)-3-(4-fluorophenyl)-2-hydroxypropionyl]-10-0-(4-propylpiperazinocarbonyl)-10-deacetylbaccatin III (Compound 1-44)

In a similar manner to Example 42, the reaction and after-treatment were conducted using Compound (2–26) (361 mg, 0.309 mmol) of Example 66 and 3,3-dimethylacryloyl chloride (41 mg, 0.342 mmol), whereby the title compound (100 mg, 36%) was obtained as colorless crystals.

$^1$H—NMR(CDCl$_3$) δ: 0.93(3H,t,J=7.3 Hz CH$_2$CH$_2$CH$_3$), 1.14(3H,s,C$_{16}$ or C$_{17}$), 1.25(3H,s,C$_{16}$ or C$_{17}$), 1.52–1.62(2H, m,CH$_2$CH$_2$CH$_3$), 1.68(3H,s,C$_{19}$), 1.81(3H,s), 1.82–1.92 (1H,m,C$_6$), 1.86(3H,s,C$_{18}$), 2.01(3H,s), 2.26–2.41(4H,m, C$_{14}$ and CH$_2$CH$_2$CH$_3$), 2.37(3H,s), 2.49–2.60(5H,m, piperazine and C$_6$), 3.13(1H,brs,C$_7$—OH), 3.40–3.73(4H, m,piperazine), 3.79(1H,d,J=6.8 Hz,C$_3$), 4.18(1H,d,J=8.3 Hz,C$_{20}$), 4.30(1H,d,J=8.3 Hz,C$_{20}$), 4.41–4.45(1H,m,C$_7$), 4.66(1H,d,J=2.4 Hz,C$_{2'}$), 4.95–4.97(1H,m,C$_5$), 5.58(1H,s, acryloyl), 5.58–5.62(1H,m,C$_3'$), 5.67(1H,d,J=7.1 Hz,C$_2$), 6.12(1H,d,J=9.0 Hz,NH), 6.22–6.26(1H,m,C$_{13}$), 6.26(1H,s, C$_{10}$), 7.05–7.10(2H,m,4FC$_6$H$_4$), 7.39–7.42(2H,m,4FC$_6$H$_4$), 7.48–7.52(2H,m,Bz), 7.59–7.63(1H,m,Bz), 8.10–8.12(2H, m,Bz).

SIMS m/z: 961(M)$^+$

Example 71

13-0-[3-Benzyloxycarbonyl-2,2-dimethyl-4-(2-methylpropyl)-5-oxazolidinecarbonyl)-10-0-(4-propylpiperazinocarbonyl)-7-0-triethylsilyl-10-deacetylbaccatin III (Compound 2-27)

In a similar manner to Example 1, the reaction and after-treatment were conducted using Compound (2-14) (2.1 g, 2.59 mmol) of Example 27 and 3-benzyloxycarbonyl-2,2-dimethyl-4-(2-methylpropyl)-5-oxazolidinecarboxylic acid (1.04 g, 3.11 mol), whereby the title compound (1.86 g, 64%) was obtained.

$^1$H—NMR(CDCl$_3$) δ: 0.51–0.66(6H,m,SiCH$_2$), 0.90–0.94(6H,m,iBu-CH$_3$), 0.92(3H,t,J=7.4 Hz,CH$_2$CH$_2$CH$_3$) 0.92(9H,t,J=7.9 Hz,SiCH$_2$CH$_3$), 1.19(3H, s,C$_{16}$ or C$_{17}$), 1.21(3H,s,C$_{16}$ or C$_{17}$), 1.48–1.57(2H,m, CH$_2$CH$_2$CH$_3$), 1.60–1.67(3H,m,iBu-CH,CH$_2$), 1.61(3H,s, isopropylidene), 1.65(3H,s,isopropylidene), 1.68(3H,s,C$_{19}$), 1.85–1.92(1H,m,C$_6$), 2.15(s,3H), 2.24(2H,d,J=9.0 Hz,C$_{14}$), 2.31–2.34(2H,m,CH$_2$CH$_2$CH$_3$), 2.36(3H,s), 2.36–2.55(4H, m,piperazine), 2.45–2.56(1H,m,C$_6$), 3.38–3.85(4H,m, piperazine), 3.87(1H,d,J=6.8 Hz,C$_3$), 4.15(1H,d,J=8.3 Hz,C$_{20}$), 4.31(1H,d,J=8.3 Hz,C$_{20}$), 4.32(1H,brs,C$_2$, or C$_3$,), 4.49(1H,dd,J=6.6,10.5 Hz,C$_7$), 4.52(1H,brs,C$_2$, or C$_3$,), 4.95–4.97(1H,m,C$_5$), 5.07–5.21(2H,m,PhCH$_2$), 5.68(1H,d, J=7.1 Hz,C$_2$), 6.15–6.20(1H,m,C$_{13}$), 6.40(1H,s,C$_{10}$), 7.31–7.37(5H,m,Z), 7.46–7.50(2H,m,Bz), 7.59–7.63(1H,m, Bz), 8.08–8.10(2H,m,Bz).

Example 72

13-0-[3-(n-Hexanoylamino)-2-hydroxy-5-methylhexanoyl]-10-0-(4-propylpiperazinocarbonyl)-10-deacetylbaccatin III (Compound 1-45)

In a similar manner to Example 42, the reaction and after-treatment were conducted using Compound (2-27) (334 mg, 0.296 mmol) of Example 71 and n-hexanoyl chloride (48 mg, 0.355 mmol), whereby the title compound (182 mg, 66%) was obtained as colorless crystals.

$^1$H—NMR(CDCl$_3$) δ: 0.84(3H,t,J=6.9 Hz,hexanoyl-CH$_3$), 0.92(3H,t,J=7.3 Hz,NCH$_2$CH$_2$CH$_3$), 0.98(3H,d,J=6.6 Hz,iBu-CH$_3$), 0.99(3H,d,J=6.6 Hz,iBu-CH$_3$), 1.14(3H,s,C$_{16}$ or C$_{17}$), 1.24(3H,s,C$_{16}$ or C$_{17}$), 1.25–1.37(2H,m,hexanoyl-CH$_2$), 1.48–1.94(10H,m,hexanoyl-CH$_2$×2,NCH$_2$CH$_2$CH$_3$, C$_6$, iBu-CH$_2$ and iBu-CH), 1.68(3H,s,C$_{19}$), 1.90(3H,s,C$_{18}$), 2.08–2.13(2H,m,C$_{14}$), 2.33–2.41(4H,m,hexanoyl-CH$_2$ and CH$_2$CH$_2$CH$_3$), 2.37(3H,s), 2.47–2.52(4H,m,piperazine), 2.50–2.57(1H,m,C$_6$), 3.17(1H,brs,C$_7$—OH), 3.43–3.73(4H, m,piperazine), 3.79(1H,d,J=7.1 Hz,C$_3$), 4.20(1H,d,J=1.7

Hz,$C_2$,), 4.23(1H,d,J=8.4 Hz,$C_2$), 4.29(1H,d,J=8.4 Hz,$C_{20}$), 4.44–4.49(2H,m,$C_7$,NH), 4.97–4.99(1H,m,$C_5$), 5.53–5.57 (1H,m,$C_3$,), 5.67(1H,d,J=7.1 Hz,$C_2$), 6.13–6.17(1H,m,$C_{13}$), 6.25(1H,s,$C_{10}$), 7.44–7.48(2H,m,Bz), 7.57–7.61(1H,m,Bz), 8.10–8.12(2H,m,Bz).

SIMS m/z: 940(M+H)$^+$

Example 73

13-0-[2-Hydroxy-5-methyl-3-(2-thenoylamino) hexanoyl]-10-0-(4-propylpiperazinocarbonyl)-10-deacetylbaccatin III (Compound 1-46)

In a similar manner to Example 42, the reaction and after-treatment were conducted using Compound (2-27) (334 mg, 0.296 mmol) of Example 71 and 2-thenoyl chloride (52 mg, 0.355 mmol), whereby the title compound (124 mg, 44%) was obtained as colorless crystals.

$^1$H—NMR(CDCl$_3$) δ: 0.92(3H,t,J=7.3 Hz,CH$_2$CH$_2$CH$_3$), 1.00–1.02(6H,m,iBu-CH$_3$×2), 1.13(3H,s,$C_{16}$ or $C_{17}$), 1.22 (3H,s,$C_{16}$ or $C_{17}$), 1.42–1.92(6H,m,CH$_2$CH$_2$CH$_3$,$C_6$,iBu-CH$_2$ and iBu-CH), 1.68(3H,s,$C_{19}$), 1.89(3H,s,$C_{18}$), 1.87–1.93(1H,m,$C_6$), 2.29–2.39(4H,m,$C_{,14}$ and CH$_2$CH$_2$CH$_3$), 2.42(3H,s), 2.46–2.58(5H,m,piperazine and $C_6$), 3.16(1H,brs,$C_7$—OH), 3.41–3.73(4H,m,piperazine), 3.80(1H,d,J=7.1 Hz,$C_3$), 4.24(1H,d,J=8.4 Hz,$C_{20}$), 4.30(1H, d,J=8.4 Hz,$C_{20}$), 4.32(1H,d,J=1.9 Hz,$C_2$,), 4.42–4.47(1H,m, $C_7$), 4.63–4.69(1H,m,$C_3$,), 4.97–5.00(1H,m,$C_5$), 5.67(1H,d, J=7.1 Hz,$C_2$), 6.18–6.23(2H,m,$C_{13}$ and NH), 6.25(1H,s, $C_{10}$), 7.46–7.53(3H,m,Bz and thenoyl), 7.59–7.61(1H,m, Bz), 8.13–8.15(2H,m,Bz).

SIMS m/z 951(M)$^+$

Example 74

13-0-[3-(3,3-Dimethylacryloylamino)-2-hydroxy-5-methylhexanoyl]-10-0-(4-propylpiperazinocarbonyl)-10-deacetylbaccatin III (Compound 1-47)

In a similar manner to Example 42, the reaction and after-treatment were conducted using Compound (2-27) (334 mg, 0.296 mmol) of Example 71 and 3,3-dimethylacryloyl chloride (42 mg, 0.355 mmol), whereby the title compound (91 mg, 33%) was obtained as colorless crystals.

$^1$H—NMR(CDCl$_3$) δ: 0.89(3H,t,J=7.4 Hz CH$_2$CH$_2$CH$_3$), 0.96(3H,d,J=6.8 Hz,iBu-CH$_3$), 0.96(3H,d,J=6.8 Hz,iBu-CH$_3$), 1.11(3H,s,$C_{16}$ or $C_{17}$), 1.21(3H,s,$C_{16}$ or $C_{17}$), 1.31–1.90 (6H,m, CH$_2$CH$_2$CH$_3$, $C_6$,iBu-CH$_2$ and iBu-CH), 1.66(3H,s,$C_{19}$), 1.76(3H,s), 1.87(3H,s,$C_{18}$), 1.94(3H,s), 2.31–2.40(4H,m,$C_{14}$ and CH$_2$CH$_2$CH$_3$), 2.37(3H,s), 2.47–2.59(5H,m,piperazine and $C_6$), 3.15(1H,brs,$C_7$—OH), 3.40–3.70(4H,m,piperazine), 3.77(1H,d,J=6.8 Hz,$C_3$), 4.19 (1H,d,J=8.2 Hz,$C_{20}$), 4.20(1H,d,J=2.0H z,$C_2$,), 4.27(1H,d, J=8.2 Hz,$C_{20}$), 4.40–4.45(2H,m,$C_7$ and $C_3$,), 4.95–4.97(1H, m,$C_5$), 5.41–5.44(1H,m), 5.48(1H,s,acryloyl), 5.64(1H,d,J= 7.1 Hz,$C_2$), 6.13–6.17(1H,m,$C_{13}$), 6.23(1H,s,$C_{10}$), 7.42–7.46(2H,m,Bz), 7.55–7.59(1H,m,Bz), 8.08–8.10(2H, m,Bz).

SIMS m/z: 924(M+H)$^+$

Example 75

13-0-[3-(tert-Butoxycarbonylamino)-2-hydroxy-5-methylhexanoyl]-10-0-(4-propylpiperazinocarbonyl)-10-deacetylbaccatin III (Compound 1-48)

In a similar manner to Example 16, the reaction and after-treatment were conducted using Compound (2-27) (334 mg, 0.296 mmol) of Example 71 and di-tert-butyl dicarbonate (50 mg, 0.229 mmol), whereby the title compound (15 mg, 32%) was obtained as colorless crystals.

$^1$H—NMR(CDCl$_3$) δ: 0.93(3H,t,J=7.4 Hz CH$_2$CH$_2$CH$_3$), 0.97–0.99(6H,m,iBu-CH$_3$×2), 1.14(3H,s,$C_{16}$ or $C_{17}$), 1.24 (3H,s,$C_{16}$ or $C_{17}$), 1.31(9H,s,tBu), 1.49–1.95(6H,m, CH$_2$CH$_2$CH$_3$,$C_6$,iBu-CH$_2$ and iBu-CH), 1.68(3H,s,$C_{19}$), 1.92(3H,s,$C_{18}$), 2.31–2.40(4H,m,$C_{14}$ and CH$_2$CH$_2$CH$_3$), 2.38(3H,s), 2.47–2.59(5H,m,piperazine and $C_6$), 3.15(1H, brs,$C_7$—OH), 3.40–3.72(4H,m,piperazine), 3.80(1H,d,J= 6.8 Hz,$C_3$), 4.10–4.18(2H,m,$C_{27}$ and NH), 4.20(1H,d,J=8.7 Hz,$C_{20}$), 4.30(1H,d,J=8.7 Hz,$C_{20}$), 4.43–4.48(1H,m,$C_7$), 4.60(1H,d,J=9.5 Hz,$C_3$,), 4.96–4.99(1H,m,$C_5$), 5.66(1H,d, J=7.1 Hz,$C_2$), 6.17–6.21(1H,m,$C_{13}$), 6.27(1H,s,$C_{10}$), 7.46–7.49(2H,m,Bz), 7.59–7.62(1H,m,Bz), 8.11–8.13(2H, m,Bz).

SIMS m/z: 941(M)$^+$

Example 76

13-0-[3-Benzyloxycarbonyl-4-cyclopropylmethyl-2,2-dimethyl-5-oxazolidinecarbonyl]-10-0-(4-propylpiperazinocarbonyl)-7-0-triethylsilyl-10-deacetylbaccatin III (Compound 2-28)

In a similar manner to Example 1, the reaction and after-treatment were conducted using Compound (2-14) (300 mg, 0.369 mmol) of Example 27 and 3-benzyloxycarbonyl-4-cyclopropylmethyl-2,2-dimethyl-5-oxazolidinecarboxylic acid (135 mg, 0.405 mmol), whereby the title compound (330 mg, 79%) was obtained as a colorless solid.

$^1$H—NMR(CDCl$_3$) δ: −0.01–0.20(2H,m,cPr—CH$_2$), 0.40–0.50(2H,m,cPr—CH$_2$), 0.54–0.66(7H,m,SiCH$_2$ and cPr—CH), 0.92(3H,t,J=7.3 Hz,CH$_2$CH$_2$CH$_3$), 0.92(9H,t,J= 7.9 Hz,SiCH$_2$CH$_3$), 1.20(3H,s,$C_{16}$ or $C_{17}$), 1.21(3H,s,$C_{16}$ or $C_{17}$), 1.48–1.57(2H,m,CH$_2$CH$_2$CH$_3$), 1.60–1.67(2H,m, CH$_2$), 1.61(6H,s,isopropylidene), 1.68(3H,s,$C_{19}$), 1.85–1.92 (1H,m,$C_6$), 2.16(s,3H), 2.24–2.27(2H,m,$C_{14}$), 2.31–2.34 (2H,m,CH$_2$CH$_2$CH$_3$), 2.35(3H,s), 2.36–2.55(4H,m, piperazine), 2.47–2.56(1H,m,$C_6$), 3.38–3.88(4H,m, piperazine), 3.87(1H,d,J=6.8 Hz,$C_3$), 4.15(1H,d,J=8.4 Hz,$C_{20}$), 4.49(1H,d,J=8.4 Hz,$C_{20}$), 4.49(1H,dd,J=6.6,10.5 Hz,$C_7$), 4.54(1H,br,$C_2$, and $C_3$,), 4.95–4.97(1H,m,$C_5$), 5.05–5.19(2H,m,PhCH$_2$), 5.69(1H,d,J=7.1 Hz,$C_2$), 6.16–6.20(1H,m,$C_{13}$), 6.40(1H,s,$C_{10}$), 7.31–7.40(5H,m,Z), 7.46–7.50(2H,m,Bz), 7.59–7.63(1H,m,Bz), 8.07–8.9(2H,m, Bz).

Example 77

13-0-[4-Cyclopropyl-3-(n-hexanoylamino)-2-hydroxybutylyl]-10-0-(4-propylpiperazinocarbonyl)-10-deacetylbaccatin III (Compound 1-49)

In a similar manner to Example 42, the reaction and after-treatment were conducted using Compound (2-28) (56 mg, 0.0494 mmol) of Example 76 and n-hexanoyl chloride (8 mg, 0.0593 mmol), whereby the title compound (17 mg, 37%) was obtained as colorless crystals.

$^1$H—NMR(CDCl$_3$) 67 : 0.13–0.21(2H,m,cPr—CH$_2$), 0.50–0.59(2H,m,cPr—CH$_2$), 0.66–0.75(1H,m,cPr—CH), 0.83(3H,t,J=7.0 Hz,hexanoyl-CH$_3$), 0.94(3H,t,J=7.3 Hz,NCH$_2$CH$_2$CH$_3$), 1.14(3H,s,$C_{16}$ or $C_{71}$), 1.20–1.26(4H, m,hexanoyl-CH$_2$×2), 1.26(3H,s, $C_{16}$ or $C_{17}$), 1.48–1.65(6H, m,hexanoyl-CH$_2$,NCH$_2$CH$_2$CH$_3$ and CH$_2$), 1.68(3H,s,$C_{19}$), 1.85–1.93(1H,m,$C_6$), 1.91(3H,s,$C_{18}$), 2.04–2.58(11H,m, $C_{14}$,hexanoyl-CH$_2$,CH$_2$CH$_2$CH$_3$,piperazine and $C_6$), 2.42

(3H,s), 3.15(1H,brs,C₇—OH), 3.40–3.73(4H,m,piperazine), 3.79(1H,d,J=7.1 Hz,C₃), 4.21(1H,d,J=8.4 Hz,C₂₀), 4.31(1H, d,J=8.4 Hz,C₂₀), 4.41–4.46(2H,m,C₇ and C₃,), 4.47(1H,d, J=1.7 Hz,C₂,), 4.96–4.99(1H,m,C₅), 5.67–5.69(2H,m,C₂ and NH), 6.16–6.20(1H,m,C₁₃), 6.27(1H,s,C₁₀), 7.48–7.54 (2H,m,Bz), 7.59–7.63(1H,m,Bz), 8.11–8.14(2H,m,Bz).

SIMS m/z: 938(M+H)⁺

Example 78

13-0-(4-Cyclopropyl-2-hydroxy-3-(2-thenoylamino) butyryl]-10-0-(4-propylpiperazinocarbonyl)-10-deacetylbaccatin III (Compound 1-50)

In a similar manner to Example 42, the reaction and after-treatment were conducted using Compound (2-28) (56 mg, 0.0494 mmol) of Example 76 and 2-thenoyl chloride (9 mg, 0.0593 mmol), whereby the title compound (21 mg, 45%) was obtained as colorless crystals.

¹H—NMR(CDCl₃) δ: 0.15–0.23(2H,m,cPr—CH₂), 0.51–0.60(2H,m,cPr—CH₂), 0.75–0.80(1H,m,cPr—CH), 0.93(3H,t,J=7.4 Hz,CH₂CH₂CH₃), 1.13(3H,s,C₁₆ or C₁₇), 1.22(3H,s,C₁₆ or C₁₇), 1.54–1.93(5H,m,CH₂CH₂CH₃,C₆ and iBu-CH₂), 1.68(3H,s,C₁₉), 1.89(3H,s,C₁₈), 2.25–2.31 (2H,m,C₁₄), 2.38–2.44(2H,m,CH₂CH₂CH₃), 2.43(3H,s), 2.50–2.59(5H,m,piperazine and C₆), 3.14(1H,brs,C₇—OH), 3.40–3.80(4H,m,piperazine), 3.80(1H,d,J=7.1 Hz,C₃), 4.22 (1H,d,J=8.3 Hz,C₂₀), 4.31(1H,d,J=8.3H z,C₂₀), 4.40–4.47 (1H,m,C₇), 4.56(1H,d,J=2.0 Hz,C₂,), 4.62–4.68(1H,m,C₃,), 4.97–4.99(1H,m,C₅), 5.67(1H,d,J=7.1 Hz,C₂), 6.21–6.25 (1H,m,C₁₃), 6.25(1H,s,C₁₀), 6.30(1H,d,J=9.3 Hz,NH), 7.02–7.04(1H,m,thenoyl), 7.42–7.45(2H,m,thenoyl), 7.51–7.54(2H,m,Bz), 7.60–7.64(1H,m,Bz), 8.14–8.16(2H, m,Bz).

SIMS m/z: 949(M)⁺

Example 79

13-0-[4-Cyclopropyl-3-(3,3-dimethylacryloylamino)-2-hydroxybutyryl]-10-0-(4-propylpiperazinocarbonyl)-10-deacetylbaccatin III (Compound 1-51)

In a similar manner to Example 42, the reaction and after-treatment were conducted using Compound (2-28) (56 mg, 0.0494 mmol) of Example 76 and 3,3-dimethylacryloyl chloride (7 mg, 0.0593 mmol), whereby the title compound (17 mg, 37%) was obtained as colorless crystals.

¹H—NMR(CDCl₃) δ: 0.15–0.19(2H,m,cPr—CH₂), 0.53–0.55(2H,m,cPr—CH₂), 0.70–0.78(1H,m,cPr—CH), 0.95(3H,t,J=7.3 Hz CH₂CH₂CH₃), 1.14(3H,s,C₁₆ or C₁₇), 1.25(3H,s,C₁₆ or C₁₇), 1.50–1.90(5H,m,CH₂CH₂CH₃,C₆ and CH₂), 1.68(3H,s,C₁₉), 1.79(3H,s), 1.91(3H,s,C₁₈), 1.98 (3H,s), 2.29–2.41(4H,m,C₁₄ and CH₂CH₂CH₃), 2.45(3H,s), 2.47–2.58(5H,m,piperazine and C₆), 3.11(1H,brs,C₇—OH), 3.47–3.80(4H,m,piperazine), 3.80(1H,d,J=6.8 Hz,C₃), 4.19 (1H,d,J=8.5 Hz,C₂₀), 4.32(1H,d,J=8.5 Hz,C₂₀), 4.41–4.47 (2H,m,C₇ and C₃,), 4.50(1H,d,J=2.0 Hz,C₂,), 4.98–4.99(1H, m,C₅), 5.50(1H,s,acryloyl), 5.56–5.58(1H,m,NH), 5.68(1H, d,J=7.1 Hz,C₂), 6.18–6.23(1H,m,C₁₃), 6.28(1H,s,C₁₀), 7.48–7.52(2H,m,Bz), 7.59–7.63(1H,m,Bz), 8.11–8.13(2H, m,Bz).

SIMS m/z: 922(M+H)⁺

Example 80

13-0-[4-Cyclopropyl-3-(tert-butoxycarbonylamino)-2-hydroxybutyryl]-10-0-(4-propylpiperazinocarbonyl)-10-deacetylbaccatin III (Compound 1-52)

In a similar manner to Example 16, the reaction and after-treatment were conducted using Compound (2-28) (56 mg, 0.0494 mmol) of Example 76 and di-tert-butyl dicarbonate (13 mg, 0.0593 mmol), whereby the title compound (23 mg, 48%) was obtained as colorless crystals.

¹H—NMR(CDCl₃) δ: 0.15–0.20(2H,m,cPr—CH₂), 0.51–0.55(2H,m,cPr—CH₂), 0.67–0.75(1H,m,cPr—CH), 0.94(3H,t,J=7.3 Hz CH₂CH₂CH₃), 1.14(3H,s, C₁₆ or C₁₇), 1.26(3H,s,C₁₆ or C₁₇), 1.30(9H,s,tBu), 1.51–1.92(5H, m,CH₂CH₂CH₃,C₆ and CH₂), 1.67(3H,s,C₁₉), 1.92(3H,s, C₁₈), 2.31–2.70(9H,m,C₁₄,CH₂CH₂CH₃,piperazine and C₆), 2.42(3H,s), 3.15(1H,brs,C₇—OH), 3.40–3.80(4H,m, piperazine), 3.81(1H,d,J=7.1 Hz,C₃), 4.18(1H,d,J=8.4 Hz,C₂₀), 4.32(1H,d,J=8.4 Hz,C₂₀), 4.43–4.48(2H,m,C₇ and C₃,), 4.46(1H,d,J=2.0 Hz,C₂,), 4.72(1H,d,J=9.5 Hz,NH), 4.97–4.99(1H,m,C₅), 5.67(1H,d,J=7.1 Hz,C₂), 6.20–6.24 (1H,m,C₁₃), 6.28(1H,s,C₁₀), 7.49–7.52(2H,m,Bz), 7.60–7.63(1H,m,Bz), 8.12–8.14(2H,m,Bz).

SIMS m/z: 939(M)⁺

The compounds prepared in the above-described Examples 1 to 80 are shown in Tables 1 to 13.

TABLE 1

[Structure of baccatin III core with substituents A¹—OCO, OTES, ZO, HO, OAc, OBz]

| Compound No. | A¹ | Z |
|---|---|---|
| (2-1) | [piperidinyl-piperidinyl group] | [OMe-phenyl-oxazolidine with Boc, furyl, CO] |
| (2-2) | Me—N(piperazine)N— | [dimethyl-oxazolidine with CbzN, furyl, CO] |

TABLE 1-continued
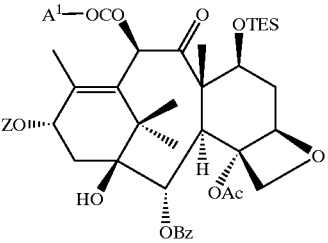
| Compound No. | A¹ | Z |
|---|---|---|
| (2-3) | 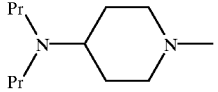 | 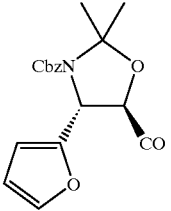 |
| (2-4) | 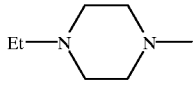 | 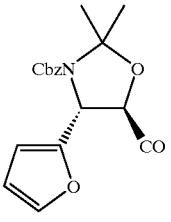 |
TABLE 1-continued
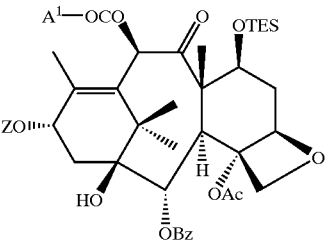
| Compound No. | A¹ | Z |
|---|---|---|
Cbz = 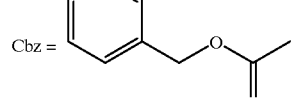
Boc = 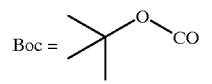
Alloc = 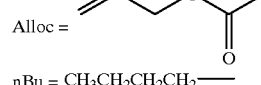
nBu = $CH_3CH_2CH_2CH_2$—
Pr = $CH_3CH_2CH_2$—
TABLE 2
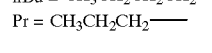
| Compound No. | A¹ | Z |
|---|---|---|
| (2-5) | 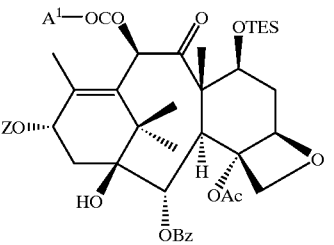 | 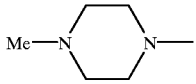 |

TABLE 2-continued
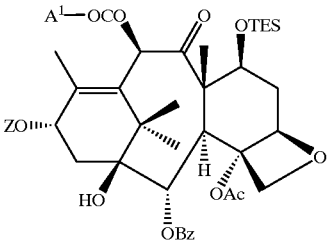
| Compound No. | A¹ | Z |
|---|---|---|
| (2-6) | 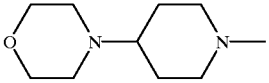 | 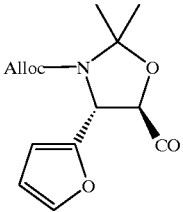 |
| (2-7) | 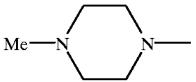 | 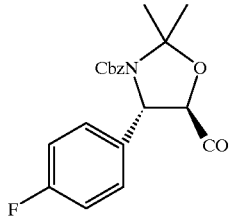 |
| (2-8) | 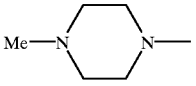 | 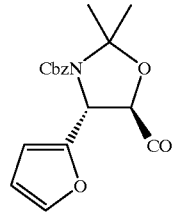 |
Cbz = 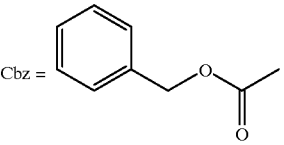
Boc = 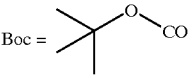
Alloc = 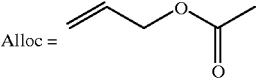
nBu = CH₃CH₂CH₂CH₂——
Pr = CH₃CH₂CH₂——

TABLE 3
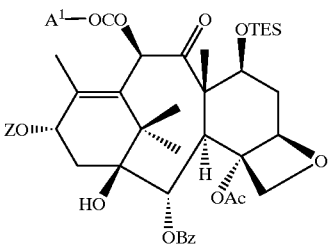
| Compound No. | A¹ | Z |
|---|---|---|
| (2-9) | 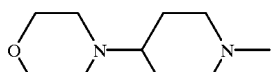 | 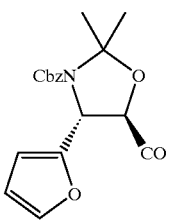 |
| (2-10) | 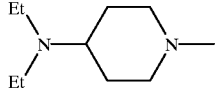 | H |
| (2-11) | 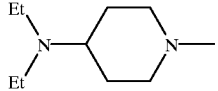 | 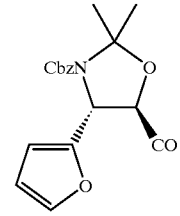 |
| (2-12) | 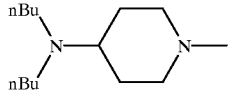 | H |
TABLE 3-continued
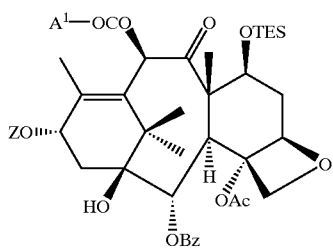
| Compound No. | A¹ | Z |
|---|---|---|
| (2-13) | 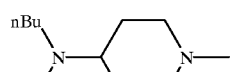 | 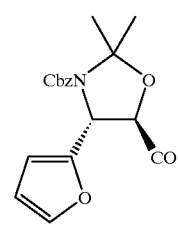 |
| (2-14) | 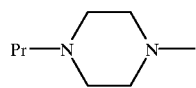 | H |
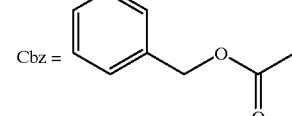
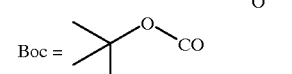
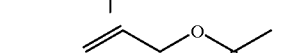

TABLE 4

| Compound No. | A¹ | Z |
|---|---|---|
| (2-15) | Pr-N(piperazine)N-Me | CbzN-oxazolidine(furan-2-yl)-CO |
| (2-16) | Me-N(piperazine)N-Me | CbzN-oxazolidine(5-methylfuran-2-yl)-CO |
| (2-17) | iPr-NH-C(O)-CH₂-N(piperazine)N-Me | CbzN-oxazolidine(4-fluorophenyl)-CO |
| (2-18) | piperidinyl-N(piperidine)N-Me | CbzN-oxazolidine(4-fluorophenyl)-CO |

TABLE 4-continued
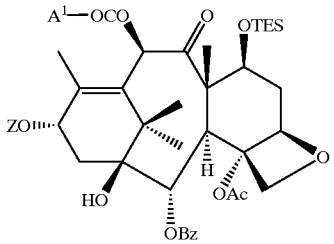
| Compound No. | A[1] | Z |
|---|---|---|
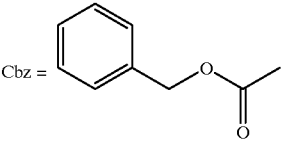
Cbz =
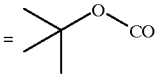
Boc =
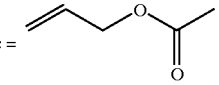
Alloc =
nBu = $CH_3CH_2CH_2CH_2-$
Pr = $CH_3CH_2CH_2-$
TABLE 5
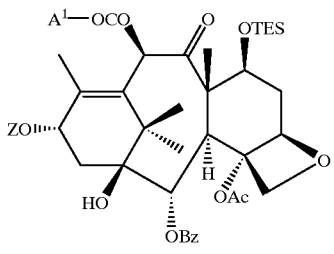
| Compound No. | A[1] | Z |
|---|---|---|
| (2-19) | 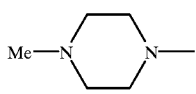 | 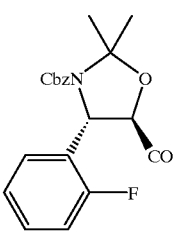 |
| (2-20) | 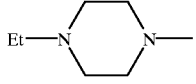 | 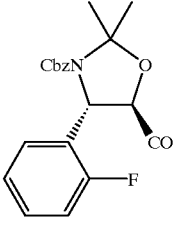 |
TABLE 5-continued
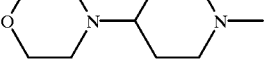
| Compound No. | A[1] | Z |
|---|---|---|
| (2-21) | 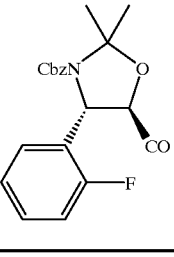 | |

TABLE 5-continued

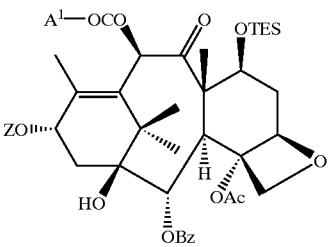

| Compound No. | A¹ | Z |
|---|---|---|

Cbz = [benzyloxycarbonyl structure]

Boc = [tert-butoxycarbonyl structure]

Alloc = [allyloxycarbonyl structure]

nBu = $CH_3CH_2CH_2CH_2$—
Pr = $CH_3CH_2CH_2$—

TABLE 6

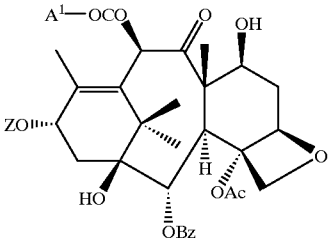

| Compound No. | A¹ | Z |
|---|---|---|
| (2-22) | Me–N(piperazine)N– | oxazolidine with CbzN, Et, CO |
| (2-23) | Me–N(piperazine)N– | oxazolidine with CbzN, tBu, CO |

TABLE 6-continued

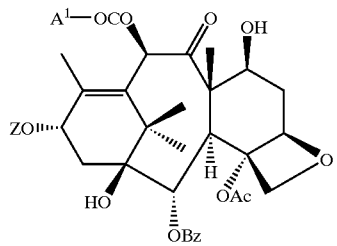

| Compound No. | A¹ | Z |
|---|---|---|
| (2-24) | Me–N(piperazine)N– | oxazolidine with CbzN, cyclopropyl, CO |
| (2-25) | nPr–N(piperazine)N– | oxazolidine with CbzN, cyclopropyl, CO |
| (2-26) | nPr–N(piperazine)N– | oxazolidine with CbzN, 4-fluorophenyl, CO |
| (2-27) | nPr–N(piperazine)N– | oxazolidine with CbzN, isobutyl, CO |
| (2-28) | nPr–N(piperazine)N– | oxazolidine with CbzN, cyclopropylmethyl, CO |

TABLE 6-continued

[Structure: taxane core with A¹—OCO, OH, ZO, HO, OAc, OBz, H substituents]

| Compound No. | A¹ | Z |
|---|---|---|

Cbz = [benzyl ester group: PhCH₂-O-C(=O)-]

tBu = CH₃C(CH₃)(CH₃)— nPr = CH₃CH₂CH₂—

TABLE 7

[Structure: taxane core with side chain X—NH, A², OH, C(=O)O—, and A¹—OCO, OH, HO, OAc, OBz, H substituents]

| Compound No. | A² | X | A¹ |
|---|---|---|---|
| (1-1) | 3-methylfuran-yl | Boc | 1-methyl-4-(piperidin-1-yl)piperidine |
| (1-2) | 3-methylfuran-yl | Boc | Me—N(piperazine)N—Me |
| (1-3) | furan-2-yl | Boc | 4-(dipropylamino)-1-methylpiperidine (Pr,Pr-N-piperidine-N—) |
| (1-4) | furan-2-yl | Boc | Et—N(piperazine)N—Me |

TABLE 7-continued
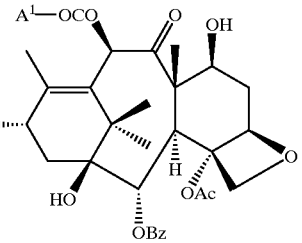
| Compound No. | A² | X | A¹ |
|---|---|---|---|
| (1-5) | 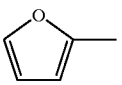 | Bz | 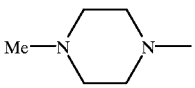 |
| (1-6) | 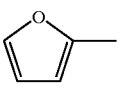 | CH₃(CH₂)₄CO | 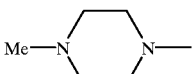 |
| (1-7) | 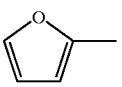 | 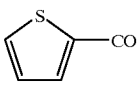 | 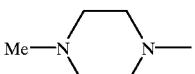 |
| (1-8) | 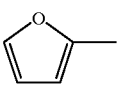 | 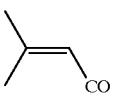 | 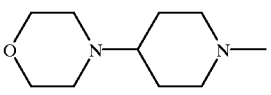 |
| (1-9) |  | Boc | 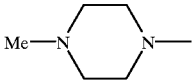 |
Bz = 
Boc = 
nBu = CH₃CH₂CH₂CH₂—
Pr = CH₃CH₂CH₂—
TABLE 8
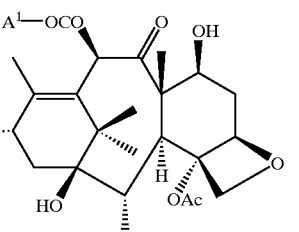
| Compound No. | A² | X | A¹ |
|---|---|---|---|
| (1-10) | 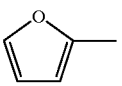 | Boc | 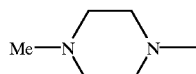 |

TABLE 8-continued
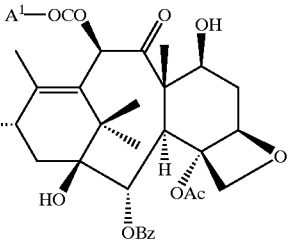
| Compound No. | A² | X | A¹ |
|---|---|---|---|
| (1-11) | 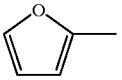 | Boc | 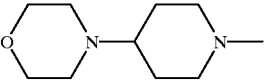 |
| (1-12) | 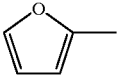 | Boc | 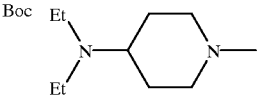 |
| (1-13) | 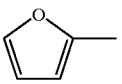 | Boc | 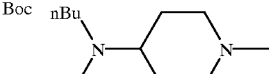 |
| (1-14) | 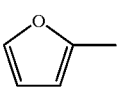 | Boc | 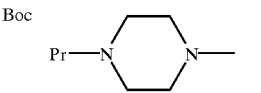 |
| (1-15) | 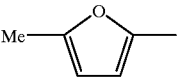 | Boc |  |
| (1-16) |  | Boc | 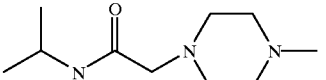 |
| (1-17) |  | Boc | 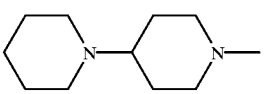 |
Bz = —CO
Boc = 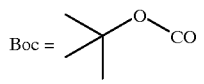
nBu = $CH_3CH_2CH_2CH_2$—
Pr = $CH_3CH_2CH_2$—

TABLE 9

[Structure diagram of taxane core with substituents X-NH, A², OH, A¹-OCO, and other groups including OH, OAc, OBz, HO]

| Compound No. | A² | X | A¹ |
|---|---|---|---|
| (1-18) | 2-fluorophenyl | Boc | Me-N(piperazine)N-Me |
| (1-19) | 2-fluorophenyl | Boc | Et-N(piperazine)N-Me |

TABLE 9-continued

[Same taxane core structure]

| Compound No. | A² | X | A¹ |
|---|---|---|---|
| (1-20) | 2-fluorophenyl | Boc | morpholino-piperidine-N-Me |

Bz = C₆H₅—CO (benzoyl)

Boc = (CH₃)₃C—O—CO nBu = CH₃CH₂CH₂CH₂—
Pr = CH₃CH₂CH₂—

TABLE 10

[Structure diagram of taxane core with substituents X-NH, A², OH, A¹-OCO]

| Compound No. | A² | X | A¹ |
|---|---|---|---|
| (1-21) | 2-furyl | n-pentyl-CO | nPr-N(piperazine)N-Me |
| (1-22) | 2-furyl | (CH₃)₂C=CH-CO | nPr-N(piperazine)N-Me |
| (1-23) | 2-furyl | 2-thienyl-CO | nPr-N(piperazine)N-Me |
| (1-24) | 2-furyl | 2-furyl-CO | nPr-N(piperazine)N-Me |

TABLE 10-continued

| Compound No. | A² | X | A¹ |
|---|---|---|---|
| (1-25) | 2-furyl | iPr-OCO | nPr-piperazinyl |
| (1-26) | 2-furyl | tAm-OCO | nPr-piperazinyl |
| (1-27) | 2-furyl | cyclohexyl-CO | nPr-piperazinyl |
| (1-28) | 2-furyl | cyclopentyl-CO | nPr-piperazinyl |
| (1-29) | 2-furyl | cyclohexyl-OCO | nPr-piperazinyl |
| (1-30) | 2-furyl | cyclopentyl-OCO | nPr-piperazinyl |

Bz = Ph-CO

Boc = tBu-O-CO nBu = CH₃CH₂CH₂CH₂— nPr = CH₃CH₂CH₂—

TABLE 11

[Structure of taxane core with X-NH, A², OH, A¹-OCO, OH, OAc, OBz, HO substituents]

| Compound No. | A² | X | A¹ |
|---|---|---|---|
| (1-31) | 2-furyl | cyclopropyl-CO | 4-methylpiperazin-1-yl |
| (1-32) | 2-furyl | CF₃—CO | 4-methylpiperazin-1-yl |
| (1-33) | Et— | Boc | 4-methylpiperazin-1-yl |
| (1-34) | tBu— | Boc | 4-methylpiperazin-1-yl |
| (1-35) | cyclopropyl | Boc | 4-methylpiperazin-1-yl |
| (1-36) | cyclopropyl | CH₃CH₂CH₂-CO | 4-methylpiperazin-1-yl |
| (1-37) | cyclopropyl | CH₃(CH₂)₄-CO | 4-methylpiperazin-1-yl |
| (1-38) | cyclopropyl | Boc | 4-n-propylpiperazin-1-yl |
| (1-39) | cyclopropyl | 2-thienyl-CO | 4-n-propylpiperazin-1-yl |

TABLE 11-continued

[Structure: taxane core with substituents X-NH, A², OH on side chain; A¹-OCO, and various ring substituents including OH, OAc, OBz, HO]

| Compound No. | A² | X | A¹ |
|---|---|---|---|
| (1-40) | cyclopropyl | (CH₃)₂C=CH–CO | nPr–N(piperazine)N– |

Bz = C₆H₅–CO

Boc = (CH₃)₃C–O–CO nBu = CH₃CH₂CH₂CH₂—
nPr = CH₃CH₂CH₂—

TABLE 12

[Structure: taxane core with substituents X-NH, A², OH on side chain; A¹-OCO, and various ring substituents including OH, OAc, OBz, HO]

| Compound No. | A² | X | A¹ |
|---|---|---|---|
| (1-41) | 4-F-C₆H₄– | Boc | nPr–N(piperazine)N– |
| (1-42) | 4-F-C₆H₄– | CH₃(CH₂)₄–CO | nPr–N(piperazine)N– |
| (1-43) | 4-F-C₆H₄– | 2-thienyl-CO | nPr–N(piperazine)N– |
| (1-44) | 4-F-C₆H₄– | (CH₃)₂C=CH–CO | nPr–N(piperazine)N– |

TABLE 12-continued

[Structure of taxane derivative with substituents X-NH, A², OH, A¹-OCO, and core taxane skeleton with OH, OBz, OAc groups]

| Compound No. | A² | X | A¹ |
|---|---|---|---|
| (1-45) | isobutyl | CH₃(CH₂)₄CO | nPr—N(piperazine)N— |
| (1-46) | isobutyl | 2-thienyl-CO | nPr—N(piperazine)N— |
| (1-47) | isobutyl | (CH₃)₂C=CH—CO | nPr—N(piperazine)N— |
| (1-48) | isobutyl | Boc | nPr—N(piperazine)N— |

Bz = C₆H₅—CO

Boc = (CH₃)₃C—O—CO nBu = CH₃CH₂CH₂CH₂—
nPr = CH₃CH₂CH₂—

TABLE 13

[Structure of taxane derivative with substituents X-NH, A², OH, A¹-OCO, and core taxane skeleton with OH, OBz, OAc groups]

| Compound No. | A² | X | A¹ |
|---|---|---|---|
| (1-49) | cyclopropylmethyl | CH₃(CH₂)₄CO | nPr—N(piperazine)N— |
| (1-50) | cyclopropylmethyl | 2-thienyl-CO | nPr—N(piperazine)N— |

TABLE 13-continued

| Compound No. | A² | X | A¹ |
|---|---|---|---|
| (1-51) | cyclopropylmethyl | (CH₃)₂C=CH-CO | nPr—N(piperazine)N— |
| (1-52) | cyclopropylmethyl | Boc | nPr—N(piperazine)N— |

Bz = C₆H₅—CO
Boc = (CH₃)₃C—O—CO
nBu = CH₃CH₂CH₂CH₂—
nPr = CH₃CH₂CH₂—

Test 1
Solubilities of Novel Water-soluble Taxane Derivatives
I) Preparation of a calibration curve Compound (1-4) was weighed in an amount of 2.3 mg, to which 2.3 mL of acetonitrile was added so that the compound was dissolved to provide a standard solution. Using a 10 μL portion of the standard solution, the test was conducted by HPLC (operation conditions 1). The peak area of Compound (1-4), which had been obtained from the chromatogram of the standard solution, was measured by automated integration. The peak area obtained as an average of three measurements was plotted against the amount (10 μg) of Compound (1-4) per 10 μL, whereby a calibration curve was prepared.

Calibration curve of Compound (1-4): $Y = 1.518 \times 10^{-5} X$ [X: peak area, Y: amount (μg) of Compound (1-4)] [HPLC operation conditions 1] Column: Inertsil ODS-2 (5-250), 40 deg. Mobile phase: 0.01M $KH_2PO_4$—$CH_3CN$ (3:2). Flow rate: 1.0 mL/min. Detection: Ultraviolet absorption photometer (225 nm), 0.2 AUFS.

II) Solubility test of Compound (1-4):

Compound (1-4) was weighed in an amount of 3.7 mg and then suspended in 2.0 mL of purified water. To the resulting suspension, 41.3 μL (1.05 eq.) of 0.1N hydrochloric acid was added. By ultrasonication, the resulting mixture was formed into a uniform suspension, which was then shaken at room temperature for 2 hours. The thus-obtained mixture was filtered through a membrane filter (0.22 μm), and the filtrate was provided as a test solution. Using a 5 μL portion of the test solution, the test was conducted by HPLC (operation conditions 1). From the area obtained as an average of three measurements, the solubility of the compound (1-4) was determined.

Area (X) of Compound (1-4) obtained as an average of three measurements: 518226

Amount (Y) of Compound (1-4) dissolved: 7.87 μg/5 μL (1.574 mg/mL).

For reference, the dissolved amount of Taxol was 0.4 μg/mL.

Test 2
Growth Inhibitory Activity of Taxane Derivatives (1)
Materials and procedures
Cells As KB cells derived from a human mouth cancer, those purchased from Dainippon Pharmaceutical Co., Ltd. and stored in a lyophilized from at the Research Institute of that company was used. In Dulbecco's modified Eargle's medium containing 10% fetal bovine serum (product of NISSUI PHARMACEUTICAL CO., LTD.), the KB cells were cultured and maintained under the conditions of 5%, $CO_2$-ari and 37° C.

Drugs

Each compound was used by dissolving it in DMSO at a concentration of 10 mg/mL.

Drug Treatment
(1) KB

On Day-1, cells which were in a logarithmic growth phase were inoculated at 2,000 cells/100 μl/well on 96-well microtiter plates (Falcon #3072) by using a phenol-red-free culture medium with 10% fetal bovine serum contained therein (Dulbecco's modified Eargle's medium (Sigma)), and were cultured overnight. On Day 0, the compounds each of which had been diluted to 0.03 to 10,000 ng/mL with the same culture medium were added in 100 μl aliquots to the individual wells, and the cells were cultured for 3 days. Three wells were used per each drug concentration. Each plate was provided with three blank wells containing only the culture medium and also with eight wells as a drug-untreated control.

XTT Assay

Upon use, XTT (Sigma) was dissolved at a concentration of 1 mg/mL in each culture medium which was free of serum. Phenodin methosulfate (Sigma) dissolved at a concentration of 5 mM in PBS was added to the resulting solution at a volume ratio of 1/200. To each well, the solution so prepared was added in an amount of 50 µl per well. Subsequent to culture for 4 hours, OD was measured at 450 nm by ELISA.

Calculation of 50% Growth Inhibitory Concentration ($GI_{50}$)

$GI_{50}$ was calculated by interpolation from a concentration-growth inhibition rate (GIR) curve. GIR was determined in accordance with the following formula:

$$GIR = 100 - \frac{OD_{Treated\,(Day\,3)} - OD_{Control\,(Day\,0)}}{OD_{Control\,(Day\,3)} - OD_{Control\,(Day\,0)}} \times 100$$

References Cited:
Scudiero. DA, et al (1988) Cancer Rds. 48: p4827–4833.
Report from Carcinostatic Screening Special Committee, "Cancer and Chemotherapy, 21, 1306–1307(1994)"
Test results are shown in Table 14.

|  | KB | |
| --- | --- | --- |
| Compound No. | $GI_{50}$ (ng/ML) | Activity ratio |
| Compound 1-1 | 0.48 | 2.70 |
| Compound 1-2 | 0.28 | 4.64 |
| Compound 1-3 | 0.43 | 3.02 |
| Compound 1-4 | 0.23 | 5.65 |
| Taxol | 1.3 | 1.00 |

Capability of Exploitation in Industry

The taxane derivatives according to the present invention have very high solubility in water, so that they can be formulated into liquid preparations such as injections without using any special solvent. In addition, they are also excellent in antitumor activities.

What is claimed is:

1. A taxane derivative represented by the following formula (1):

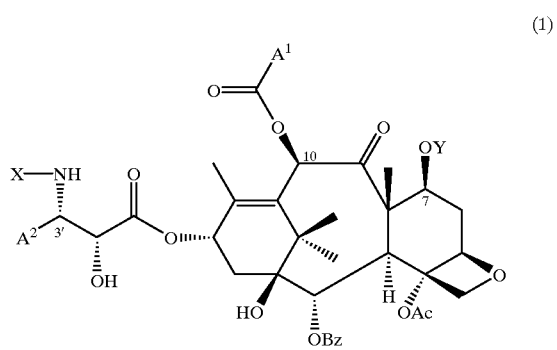

or a salt thereof.

2. A taxane derivative represented by the following formula (2):

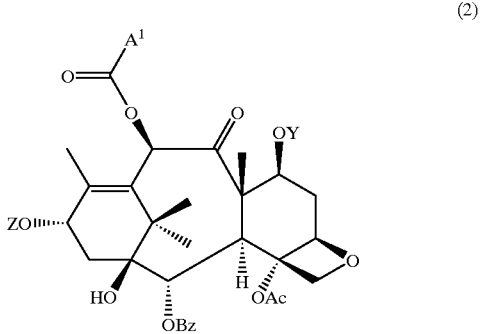

or a salt thereof.

3. A drug comprising as an active ingredient the taxane derivative or the salt thereof as claimed in claim 1.

4. An antitumor agent comprising as an active ingredient the taxane derivative or the salt thereof as claimed in claim 1.

5. A drug composition comprising the taxane derivative or the salt thereof as claimed in claim 1 and a pharmaceutically acceptable carrier.

6. A method for treating tumors, which comprises administering an effective amount of the taxane derivative or the salt thereof as claimed in claim 1.

* * * * *

UNITED STATES PATENT AND TRADEMARK OFFICE
CERTIFICATE OF CORRECTION

PATENT NO. : 6,268,381 B1
DATED : July 31, 2001
INVENTOR(S) : Hideaki Shimizu et al.

It is certified that error appears in the above-identified patent and that said Letters Patent is hereby corrected as shown below:

Column 70,
Line 16, "or a salt thereof." should read -- wherein $A^1$ represents a group 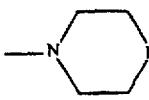 (in which $R^1$ represents a hydrogen atom, a substituted or unsubstituted alkyl group) or a group

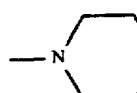 (in which $R^2$ represents an amino group, a mono- or di-alkylamino group, a piperidino group, a pyrrolidino group or a morpholino group), X represents a hydrogen atom, an alkoxycarbonyl group, an alkanoyl group which may be substituted with a fluorine atom, an alkenoyl group, a thienylcarbonyl group, a furoyl group or a benzoyl group, Y represents a hydrogen atom or a trialkylsilyl group, $A^2$ represents a furyl group, an alkylfuryl group, an alkyl group or a fluorophenyl group, Ac represents an acetyl group, and Bz represents a benzoyl group or a salt thereof. --

Line 35, "or a salt thereof." should read -- wherein $A^1$ represents a group  (in which $R^1$ represents a hydrogen atom, a substituted or unsubstituted alkyl group) or a group

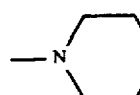 (in which $R^2$ represents an amino group, or mono- or di-alkylamino group, a piperidino group, a pyrrolidino group or a morpholino group), Y represents a hydrogen atom or a trialkylsilyl group, Z represents a hydrogen atom or the following group:

UNITED STATES PATENT AND TRADEMARK OFFICE
CERTIFICATE OF CORRECTION

PATENT NO. : 6,268,381 B1
DATED : July 31, 2001
INVENTOR(S) : Hideaki Shimizu et al.

It is certified that error appears in the above-identified patent and that said Letters Patent is hereby corrected as shown below:

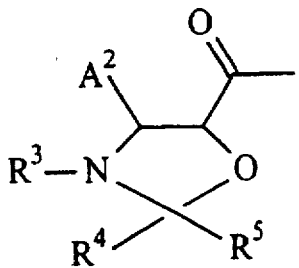

(in which $R^3$ represents a hydrogen atom, an alkoxycarbonyl group, an allyloxycarbonyl group or a benzyloxycarbonyl group, $R^4$ and $R^5$ each represents a hydrogen atom, an alkyl group or an alkoxyphenyl group with the proviso that $R^4$ and $R^5$ do not represent a hydrogen atom at the same time and that when either one of $R^4$ or $R^5$ represents an alkoxyphenyl group, the other one represents a hydrogen atom, $A^2$ represents a furyl group, an alkyfuryl group, an alkyl group or a fluorophenyl group), Ac represents an acetyl group, and Bz represents a benzoyl group or a salt thereof. --

Signed and Sealed this

Sixteenth Day of April, 2002

Attest:

*Attesting Officer*

JAMES E. ROGAN
*Director of the United States Patent and Trademark Office*